(12) United States Patent
Glover et al.

(10) Patent No.: US 7,378,489 B1
(45) Date of Patent: May 27, 2008

(54) ANGIOTENSIN DERIVATIVES

(75) Inventors: James Francis Glover, Congleton (GB); Arthur Rushton, Wilmslow (GB); Phillip John Morgan, Congleton (GB); Stephen Clinton Young, Stockport (GB)

(73) Assignee: Protherics Medicines Development Limited, Cheshire (GB)

( * ) Notice: Subject to any disclaimer, the term of this patent is extended or adjusted under 35 U.S.C. 154(b) by 0 days.

(21) Appl. No.: 09/470,997

(22) Filed: Dec. 23, 1999

(51) Int. Cl.
*C07K 7/14* (2006.01)
(52) U.S. Cl. ...................................... 530/316; 530/345
(58) Field of Classification Search ................ 530/403
See application file for complete search history.

(56) References Cited

U.S. PATENT DOCUMENTS

| 4,384,995 A | 5/1983 | Stevens |
| 5,229,490 A | 7/1993 | Tam |

FOREIGN PATENT DOCUMENTS

| WO | WO 93 08842 A | 5/1993 |
| WO | WO 97 16201 A | 5/1997 |

OTHER PUBLICATIONS

J.M. Peters et al.; "Comparison of four bifunctional reagents for coupling peptides to proteins"; J. Immunological Methods, 1989, vol. 120, pp. 133-143.
K.Y. Kumagaye et al.; "Suppression of a side reaction associated with Nim-benzyloxymethyl group during synthesis of peptides containing cysteinyl residue at the N-terminus"; Peptide Research, 1991, vol. 4, No. 2, pp. 84-87.
Kawabe H et al.; "Characterization of receptors for angiotensin-induced drinking and blood pressure responses in conscius rats using angiotensin analogsextended at the n-terminal"; NEUROENDOCRINOLOGY, 1986, vol. 42, pp. 289-295.
F.S. Tjoeng et al.; "Multiple peptide synthesis using a single support (MPS3)"; International Jounal of Peptide and Protein Research, 1990, vol. 35, pp. 141-146.

*Primary Examiner*—Christine J Saoud
(74) *Attorney, Agent, or Firm*—Bacon & Thomas PLLC

(57) ABSTRACT

An angiotensin derivative comprising at least one angiotensin peptide moiety coupled to a peptide carrier-binding moiety which can be used for therapy and prophylaxis of conditions associated with the renin activated angiotensin system.

2 Claims, 8 Drawing Sheets

ANGIOTENSIN DERIVATIVES

The present invention relates to analogues or derivatives of the mammalian peptide hormones angiotensin I and angiotensin II, and to immuno-therapeutic uses of these in particular for the therapy and prophylaxis of conditions associated with the renin activated angiotensin system.

Angiotensin peptides are involved in controlling arterial pressure in mammals. They are produced in several forms in the body as a result of a biochemical cascade known as the renin-angiotensin system (RAS), initiated by renin produced as a result of a fall in arterial pressure. In the RAS, represented schematically below, renin is released by the kidneys from stored pro-renin following a fall in arterial blood pressure, and acts enzymatically upon angiotensinogen to produce angiotensin I which is a decapeptide having the sequence Asp-Arg-Val-Tyr-Ile-His-Pro-Phe-His-Leu (SEQ ID NO: 1). Two amino acids from the C-terminus of angiotensin I are rapidly cleaved, by angiotensin converting enzyme (ACE), present in the endothelium of the lungs, generally within 1-2 seconds, to produce the octapeptide angiotensin II, having the sequence Asp-Arg-Val-Tyr-Ile-His-Pro-Phe (SEQ ID NO: 2).

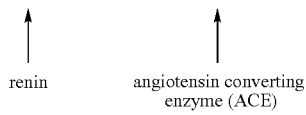

Angiotensinogen ------ > angiotensin I ------ > angiotensin II renin      angiotensin converting enzyme (ACE)

Angiotensin I is very short lived within the body and has mild vasoconstrictor activity. Alone therefore it has insignificant effect on the circulatory system. Angiotensin II, however, is a vasoactive peptide which has a profound effect on the circulatory system, as well as on the endocrine system. Elevated levels of RAS-activated angiotensin II cause vasoconstriction and renal retention of salt and water, both of which contribute to increased arterial pressure (hypertension) which can lead to cardiovascular damage. Angiotensin II has been implicated in a number of other disease states, including congestive heart failure. Hypertension is a major risk factor for heart attacks and strokes and congestive heart failure is the disease with the highest mortality within a few years of onset. There is a need for effective therapies for combating these and other diseases associated with the renin-angiotensin system.

Current treatment for these diseases includes intervention in the RAS system using small organic molecules. One approach attempts to inhibit ACE with inhibitors such as lisinopril, captopril and enalapril, agents which are now established in management of hypertension. These drugs have not however been entirely successful. It seems that inhibition of ACE is only partial. Furthermore, because ACE lacks substrate specificity, biotransformation of other metabolically active peptides, including brakykinin may also be inhibited, which is undesirable. In addition, these drugs need to be taken on a regular basis, often for long periods, such as for the majority of adult life. A major drawback, however, of these drugs is their undesirable side effects, including dry cough and a first dose hypotensive effect with dizziness and possible fainting. Since anti-hypertensive therapies invariably need to be taken long term, e.g. for up to 30 years and sometimes even longer, these adverse side effects can result in loss of patient compliance, particularly in the absence of short term clinical benefit in a mainly asymptomatic condition, severely limiting the usefulness of this therapeutic approach.

A more recent therapeutic approach involves drugs which are angiotensin receptor antagonists which are intended to block the activity of angiotensin II. Examples include losartan and valsartan. The agents which have been developed to date appear to be specific for only the $AT_1$ angiotensin receptor; they therefore block the dominant vasoconstrictor effects of angiotensin II, and are better tolerated but do not affect other actions of the angiotensin hormones. Experience with $AT_1$ receptor antagonists indicates that whilst they may be of comparable effectiveness to ACE inhibitors poor patient compliance remains a problem. There is accordingly a need for improved therapies of diseases associated with the RAS.

A potential approach in treating or preventing diseases or disorders associated with the activity of a hormone is to neutralise the effects of the hormone within the patient by immunotherapy i.e. by immunising the patient against the hormone such that the activity of the hormone is neutralised by specific anti-hormone antibodies. Such antibodies may be exogenously administered in passive immunisation or they may be generated in situ by active immunisation using an immunogen based on the hormone.

We have now developed new derivatives of angiotensin which are potent immunogens and which can be used in an immunotherapeutic approach to combat conditions associated with elevated levels of angiotensin II produced by the RAS.

In particular, derivatives of angiotensin have been developed in which one or more angiotensin peptides are coupled to a binder moiety, e.g. a peptide sequence, which facilitates attachment of the angiotensin peptide to an immunological carrier such as a protein or polypeptide to form an immunogenic conjugate capable in an immunised host of inducing antibodies which bind to angiotensin and neutralise its effects. These induced antibodies include those which may also bind to the precursor form, angiotensinogen and in this way, cleavage by renin to angiotensin I is prevented, thereby providing an additional blockade of the system. This may be particularly relevant to reducing the effects of modulation of the negative feedback effects of Angiotensin II on renin production and release of Angiotensin I.

In one aspect, the present invention thus provides an angiotensin derivative comprising at least one angiotensin peptide moiety coupled to a peptide carrier-binding moiety.

These angiotensin derivatives may be used to immunise a patient against the hormone angiotensin II and/or its polypeptide precursor angiotensin I and/or angiotensinogen such that the activity of the hormone is neutralised by specific anti-hormone or antipolypeptide antibodies.

The angiotensin peptide moiety may be any moiety, without necessarily having the biological activity of a native angiotensin (i.e. native hormone activity at the receptors, including both angiotensins I and II), in the body which is capable of acting as an immunomimic of native angiotensin peptides i.e. which immunologically mimics angiotensin so as to generate antibodies which bind to native angiotensin peptides. Thus, such a moiety may conveniently comprise an angiotensin peptide, preferably angiotensin I (a decapeptide of formula Asp-Arg-Val-Tyr-Ile-His-Pro-Phe-His-Leu (SEQ ID NO: 1)) or angiotensin II (an octapeptide of formula Asp-Arg-Val-Tyr-Ile-His-Pro-Phe (SEQ ID NO: 2)), or a functionally equivalent variant thereof. Such variants may include modifications of the angiotensin I or II sequence by single or multiple amino acid substitution, addition or deletion and also sequences where the amino acid residues are chemically modified, but which nonetheless retain angiotensin immunogenic activity. Such functionally (i.e. immunologically) equivalent variants may occur as natural biological variations, or they may be prepared using known and standard techniques for example by chemical synthesis or modification, mutagenesis, e.g. site-directed or random mutagenesis etc. The important feature as regards the modification is that the angiotensin peptide retains the ability to act as immunomimic of native angiotensin. Thus for example, an amino acid may be replaced by another which preserves the physiochemical character of the angiotensin peptide or its epitope(s) e.g. in terms of charge density, hydrophilicity/hydrophobicity, size and configuration and hence preserve the immunological structure. "Addition" variants may include N- or C-terminal fusions as well as intrasequence insertion of single or multiple amino acids. Deletions may be intrasequence or may be truncation from the N- or C-termini. The term "angiotensin peptide" as used herein includes all native angiotensin peptides and their functionally equivalent variants.

The carrier-binding moiety serves as a means by which the angiotensin peptide moiety may be attached to an immunological carrier, which will generally be a protein or polypeptide, and thus preferably contains an amino acid residue having a reactive side chain, via which the angiotensin derivative may readily be coupled to the carrier using standard coupling techniques. Advantageously such a side chain may contain a free hydroxyl, carboxyl or thiol group. Such an amino acid may thus conveniently be a cysteine, tyrosine, aspartic acid or glutamic acid residue or a derivative thereof such as N-acetyl cysteine.

Angiotensin analogues of the invention have been shown to have improved coupling to an immunological carrier for inducing antibodies which can be used immunotherapeutically and these analogues have advantages in this regard over the native peptide.

The carrier-binding moiety may take the form of a peptide extension at the N- or C-terminal of an angiotensin peptide, or a peptide pendant from or disposed within a chain segment between two or more angiotensin moieties.

Viewed from a further aspect, the present invention can be seen to provide an angiotensin derivative of Formula I

  (I)

Group L may be any organic linker structure, preferably however, it is a peptide chain, which may be linear or branched or a single amino acid residue, containing residues of natural or synthetic amino acids or pseudo-amino acids. However it may also represent a carboxyl- or amine-terminating dendritic or cascade polymer, for example a branched polyamine.

When t=0, it will be seen that the compounds of Formula (I) include derivatives wherein a carrier binding moiety (i.e. X-Y or X-L-Y) is attached at the N- or C-terminus of an angiotensin peptide, as a simple N- or C-terminal extension, or wherein multiple angiotensin peptide moieties are linked to a carrier-binding moiety terminating in a group Y, for example as a dendritic array or where the angiotensin moieties are attached at multiple sites on the carrier-binding moiety.

When t=1, it will be seen that the derivatives may take the form of a "dimer"-type structure wherein the carrier-binding group Y of the carrier-binding moiety is disposed within a chain segment of the derivative i.e. effectively between two or more angiotensin peptide moieties.

If t=1, and L is an amino acid residue or a peptide chain, L may be or include a "chain-inverting" amino acid or pseudo amino acid (i.e. a compound capable of linking two peptide moieties, e.g. a diamine or dicarboxylic acid), this being a compound capable of inverting or reversing the N- to C-terminal direction of the peptide chain. Such a compound will thus generally include two amino or two carboxylic acid groups, e.g. glutamic acid or a α,ω-alkylene diamine or α,ω-alkylene dicarboxylic acid. When t=1, it is furthermore preferred that the total number of groups ((A)-$X_n$)—does not exceed 8.

Preferred compounds of Formula (I) include those wherein n and r are each 0-10, preferably 1-6, and those wherein m and s are each $\leq 8$, preferably 1, 2 or 4.

Group X preferably represents an amino acid having no side chain or a hydrocarbyl side chain (preferably an alkyl, $C_{3-7}$ cycloalkyl or cycloalkenyl, $C_{3-7}$ cycloalkyl- or cycloalkenyl-alkyl, alkaryl, aralkyl or alkarylalkyl moiety in which each alkyl moiety may be saturated or unsaturated and contains up to 6 carbons and each aryl moiety is preferably a phenyl ring), particularly preferably an aliphatic side chain. Glycine, alanine, α-alanine, valine, leucine and isoleucine are preferred and glycine is especially preferred.

Group Y is preferably cysteine, tyrosine, glutamic acid or aspartic acid or a derivative thereof such as N-acetyl-cysteine.

Group L preferably contains at least one residue of an amino acid or pseudo amino acid containing at least glutamic acid or aspartic acid, particularly where t=0. Conveniently, such a preferred group L is a linear or branched peptide chain, eg. containing 2 to 15 amino acid residues. Branching may, of course, occur by peptide bond formation at an amine or carboxyl group of an amino acid residue side chain, eg. at a side chain amine group of lysine or arginine or at a side chain carboxyl group of aspartic or glutamic acid. A group L comprising one or more, eg. 1 to 3, lysine residues is especially preferred. Branching may occur by peptide bond formation at both the α-amino and ε-amino groups of lysine.

Preferred compounds of Formula (I) thus include compounds of Formulae (II) to (IV):

  (II)

  (III)

  (IV)

  (V)

wherein A, X, L, n and r are as hereinbefore defined and $m \leq 2$.

Where the compounds of Formula (IV) contain more than one (A) group, these are preferably attached at the same terminus i.e. preferably all are N-terminally or all are C-terminally attached.

In compounds of Formulae (II) and (III) where X is C-terminally attached to a group A being an angiotensin peptide, Y is preferably cysteine. Where X is attached to the N-terminus of A, Y is preferably N-acetyl-cysteine.

In Formulae (II) to (V) $X_n$ or $X_r$ are each preferably chains of 1 to 6 glycine residues.

In compounds of formula (IV), m is preferably 2 or 4.

In Formulae (III) to (IV), L is preferably lysine,

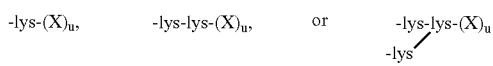, 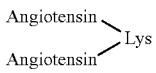 or 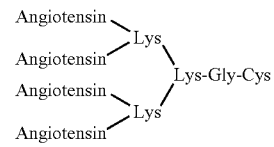

wherein u is 0 to 10, preferably 0 to 6, and X is an amino acid as defined above.

Thus, preferred compounds of Formula (IV) are those of Formulae (VI) and (VII):

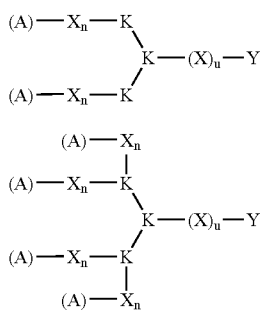

where A, X, Y, n and u are as hereinbefore defined, and K is lysine.

In the "dimer-type" derivatives of Formula (V) the angiotensin peptide moiety may preferably be a "reversed" or "inverted" sequence variant of an angiotensin peptide ie. an angiotensin peptide in which the order of the constituent amino acids is reversed.

Representative angiotensin derivatives according to the invention include:

A-(Gly)$_{1-6}$-cys (SEQ ID NOs: 9, 10 and 32-41);
N-Acetylcys-(Gly)$_{1-6}$-A (SEQ ID NOs: 11, 12 and 42-51);

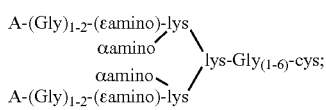

(The A-(Gly)$_{1-2}$-moiety may be bonded to either the α-amino or the ε-amino group)

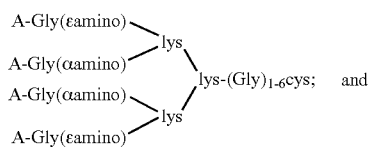

A'-(Gly)$_{1-6}$-cys-(Gly)$_{1-6}$-A (SEQ ID NOs: 13-20 and 52-331);
N-acetyl-Cys-Ala-Angiotensin
(SEQ ID NOs: 21 and 22)
N-acetyl-Cys-(Ala)$_4$-Angiotensin
(SEQ ID NOs: 23 and 24)
N-acetyl-Cys(Gly)$_6$-Angiotensin
(SEQ ID NOs: 25 and 26)
N-acetyl-Cys-Gly-Ala-Gly-Ala-Angiotensin
(SEQ ID NOs: 27 and 28)

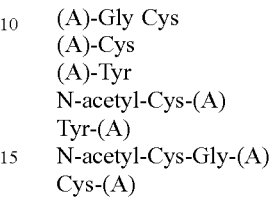

(A)-Gly Cys
(A)-Cys
(A)-Tyr
N-acetyl-Cys-(A)
Tyr-(A)
N-acetyl-Cys-Gly-(A)
Cys-(A)

wherein A is angiotensin I or angiotensin II and A' is angiotensin I or angiotensin II or an inverted or reverse angiotensin I or angiotensin II sequence.

Although Glycine is preferred, aliphatic side chain amino acids may be used in place of one or more of the Gly residues in the above formula.

Although the peptide analogues of the invention when examined by computer-aided energy minimisation modelling are generally considered too small to be optimally immunogenic alone, it has been found that when coupled via the carrier-binding moiety to a carrier, these peptide analogues elicit a strong protective immune response. They are thus eminently suitable for use in immunotherapy against RAS-associated conditions. Without wishing to be bound by theory, it is believed that coupling of the peptides to a carrier by means of the carrier-binding moiety results in the analogues having substantially the same conformation as that of the native angiotensin peptides.

The new derivatives according to the invention may be generated using a number of standard techniques including, for peptides, the Merrifield solid phase method in which amino acids are added stepwise to a growing polypeptide linked to a solid matrix as described in R. B. Merrifield, Fed. Proc. Amer. Soc. Biol. (1962). 21, 412 and R. B. Merrifield, Jour. Amer. Chem. Soc. (1963), 85, 2149 and conventional FMOC chemistry. If desired, reactive side chain groups of the amino acids in the growing chain may be protected during the chain synthesis. Branched structures may be prepared by similar techniques.

Where the new derivatives are linear peptides these may also be prepared by recombinant DNA expression using techniques known in the art e.g. as described, for example, by Sambrook et al., in Molecular Cloning: A Laboratory Manual, Second Edition, 1989.

Thus the present invention also provides a nucleic acid molecule coding for the angiotensin peptide derivatives of the invention, and nucleic acid molecules with sequences complementary thereto.

According to a further aspect of the invention, we provide an expression vector comprising the said nucleic acid molecule of the invention. Such a vector may be suitable for expression in microorganisms which may be prokaryotic or eukaryotic e.g. E coli or yeast, or in plant or animal e.g. mammalian cells.

Such an expression vector, capable in situ of synthesising an angiotensin derivative according to the invention may also be used therapeutically and may be introduced to the subject in a variety of ways. Examples of these include topical application of the 'naked' nucleic acid vector in an appropriate vehicle for example in solution in a pharmaceutically acceptable excipient such as phosphate buffered saline (PBS), or administration of the vector by physical methods such as particle bombardment, also known as 'gene gun' technology, according to methods known in the art e.g. as described in U.S. Pat. No. 5,371,015 in which inert particles, such as gold beads coated with the vector are accelerated at speeds sufficient to enable them to penetrate the skin surface, by means of discharge under high pressure from a projecting device.

Nucleic acid sequences encoding angiotensin derivatives of the invention may also be used immuno-therapeutically in the form of delivery vectors. These include viral delivery vectors, such as adenovirus or retrovirus delivery vectors known in the art into which the nucleic acid sequence is incorporated and which can be used for immunisation in ways known in the art.

Other non-viral delivery vectors which may be used to deliver the nucleic acid vectors of the invention include lipid delivery vectors, including liposome delivery vehicles, known in the art.

According to a yet further aspect, the present invention provides a host organism transformed with a vector according to the invention.

The angiotensin derivatives of the invention, as is the case for other small molecules, may be of insufficient size to stimulate antibody formation alone and may thus need to be conjugated to a macromolecular carrier in order to stimulate antibody production and a protective immune response.

Thus according to a further aspect, the present invention provides an angiotensin derivative as defined above conjugated to a carrier, preferably a polypeptide carrier.

Coupling of the derivative of the invention to the carrier may be by methods known in the art for example by treatment with heterobifunctional linking agents. Where coupling is via a terminal cysteine (or N-acetyl cysteine), the linking agent may be m-Maleimidobenzoyl-N-hydroxysulphosuccinamide ester; in which case maleimide modifies one or more lysine side chains in the peptide carrier, and a thioether bond forms at the terminal cysteine residue. Other coupling reagents known in the art, eg carbodiimide coupling, may also be used.

Any carrier known in the art for such purposes may be used, including the purified protein derivative of tuberculin, tetanus toxoid, diphtheria toxoid, keyhole limpet hemocyanin or derivatives thereof.

Where the angiotensin derivative is a linear peptide and the carrier is a protein or polypeptide, the entire peptide conjugate may also be made by recombinant DNA methods wherein a nucleic acid molecule encoding the conjugated molecule is expressed in an appropriate host cell.

The new angiotensin derivatives of the invention may be used in an immunotherapeutic approach to combating diseases associated with normal or elevated levels of RAS activity and/or angiotensin peptides, and represents an advantageous method compared to currently available methods. Patient compliance should be increased in that less frequent dosing than is the case with current therapies is involved, and undesirable side effects are avoided.

Thus according to a further aspect, the present invention provides a pharmaceutical composition comprising an angiotensin derivative according to the invention, or a conjugated angiotensin derivative according to the invention, together with one or more pharmaceutically acceptable carriers or excipients.

Viewed from a further aspect, the invention provides an angiotensin derivative according to the invention for use in therapy.

Viewed from a yet further aspect, the invention provides the use of an angiotensin derivative according to the invention in the manufacture of a medicament for use in combating diseases associated with the renin-angiotensin system. Such diseases include congestive heart failure and hypertension such as systemic hypertension and other diseases in which the renin-angiotensin system contributes to the pathophysiology thereof, as well as diseases where the renin-angiotensin system has elevated levels of activity.

Viewed from a still yet further aspect, the invention provides a method of combating conditions associated with the renin-angiotensin system comprising administering an angiotensin derivative according to the invention.

The method may be used to modulate blood pressure.

The angiotensin derivative according to the invention optionally conjugated to a carrier or recombinant nucleic acid encoding for the derivative may be administered by all conventional methods including parenterally (e.g. intraperitoneally, subcutaneously, intramuscularly, intradermally for example in the form of inert particles such as gold pellets or beads to which the derivative is adsorbed which may be accelerated at speeds sufficient to enable them to penetrate the skin of a subject, or intravenously), topically (e.g. as a cream to the skin), intra-articulately, mucosally (e.g. orally, nasally, vaginally, rectally and via the intra-ocular route) or by intrapulmonary delivery for example by means of devices designed to deliver the agents directly into the lungs and bronchial system such as inhaling devices and nebulisers, and formulated according to conventional methods of pharmacy optionally with one or more pharmaceutically acceptable carriers or excipients, such as for example those described in Remingtons Pharmaceutical Sciences, ed. Gennaro, Mack Publishing Company, Pennsylvania, USA (1990).

Such compositions are conveniently formulated in unit dosage form e.g. for mucosal, parenteral or oral administration.

Actual treatment regimes or prophylactic regimes, formulations and dosages will depend to a large extent upon the individual patient and may be devised by the medical practitioner based on the individual circumstances.

The type of formulation will be appropriate to the route of administration. For example, parenteral administration by subcutaneous or intramuscular injection may be with a sterile aqueous suspension of the conjugated analogue in PBS, saline or water for injection, optionally together with one or more immunological adjuvants e.g. aluminium hydroxide, saponin, quill A, muramyl dipeptide, mineral or vegetable oils, vesicle-based adjuvants, non-ionic block copolymers, or DEAE dextran. Additional components such as preservatives may be used.

The dosage for injection may be in the range 1-100 µg peptide equivalent and the frequency of administration may be upwards of from once every three or six months, to once every year or once every five years.

For oral administration, the conjugated derivatives may be formulated as tablets, liquid, capsules etc. Dosages range from 1 to 1000 µg peptide equivalent with dosing occurring at intervals dependent on bioavailability of product.

According to a still yet further aspect, the present invention provides a method for achieving maximal blockade of angiotensin hormones comparable to or exceeding that achieved by existing therapies based on ACE inhibitors and/or angiotensin II receptor antagonists, said method comprising administering an angiotensin derivative according to the invention.

The invention will now be described in further detail in the following non-limiting Examples, with reference to the drawings in which.

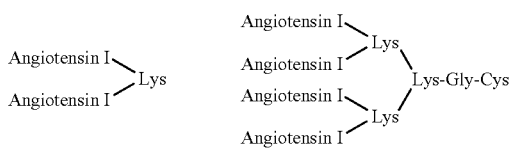

EXAMPLE 1

Peptide Generation

Figure 1:
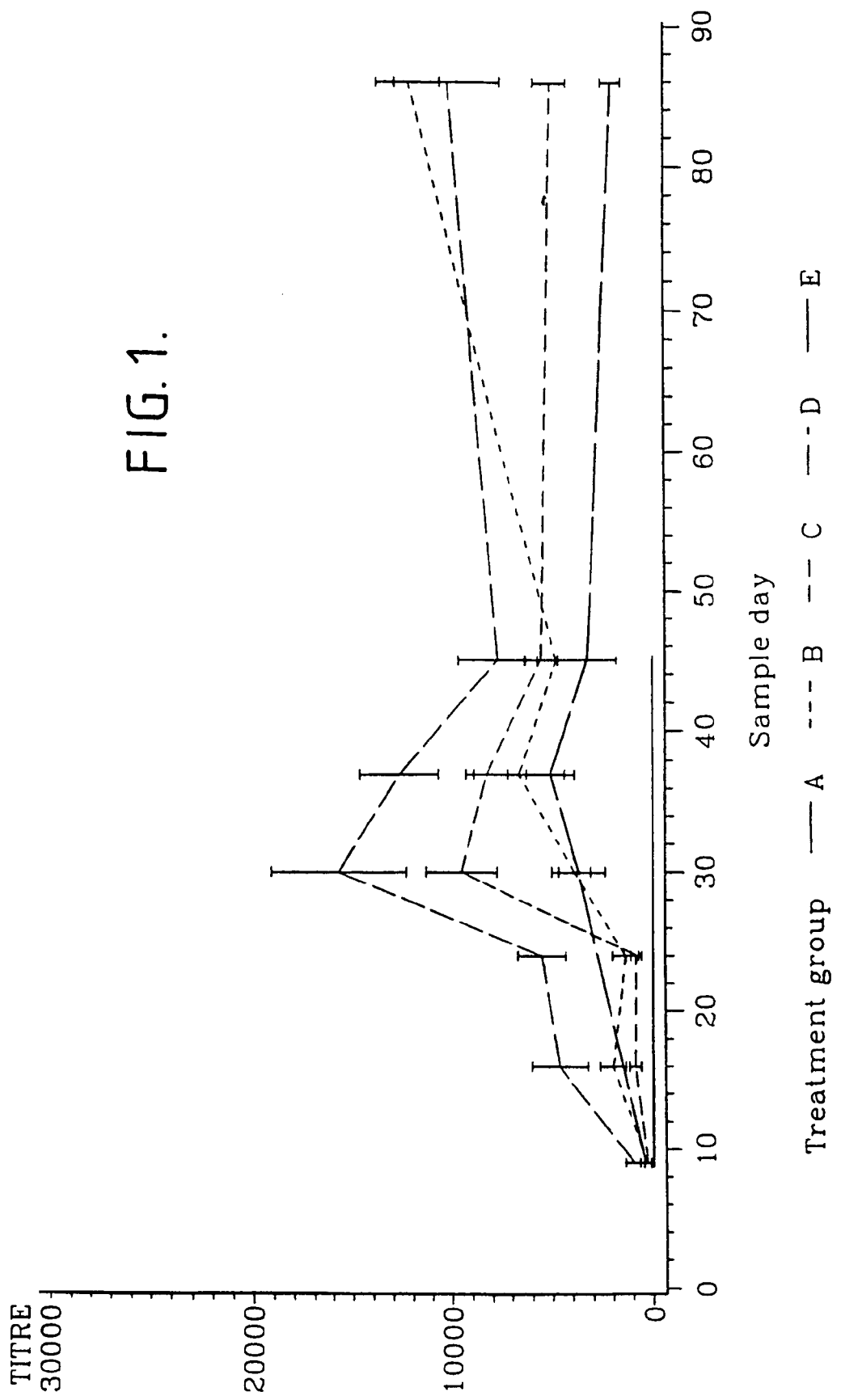
FIG. 1 is a graph showing antibody titres+/−sem, n=6 (dilution corresponding to 0.1 increase in OD) against time (sample day);
A=Control
B=Derivative 3 of Example 2
C=Derivative 1 of Example 2
D=Derivative 4 of Example 2
E=Derivative 2 of Example 2.

Peptides were synthesised by the Fmoc strategy of solid phase peptide synthesis on a Protein Technologies, Symphony Peptide Synthesiser. The resin used was Tentagel S—NH2 with a Rink Amide linker. The side chain protecting groups of the Fmoc amino acids used were Trt for Cys His, Asn and Gln, tBu for Tyr Thr, Asp, Glu and Ser; Boc for Lys and the indole N of Trp, Pmc for Arg. Activation of the carboxyl groups was achieved using, TBTU/HOBt/DIPEA, all couplings were carried out in DMF. Deprotection of the Fmoc groups was achieved with 20% Piperidine in DMF. Cleavage of the peptides from the resin was carried out with 5% Anisole/5% Thioanisole/5% EDT/3% Water/2% TES in TFA for 1 hour. The peptides were purified by RP-HPLC using a 40 mm×210 mm Deltapak C18 radial compression column on a Waters Deltaprep 4000 and characterised by MALDI-TOF on a Kratos Maldi 3 and by AAA.

For dendrimers Fmoc Lys(Fmoc)-OH is attached by the methods above and gives both α and ε amino groups free for peptide elongation. Quantities of Fmoc amino acids used have to be increased accordingly.

Rink Amide Linker=p-[(R,S-[1-(9H-Fluoren-9-yl)-methoxyformamido]-2,4-dimethoxybenzyl]-phenoxyacetic acid Fmoc=9-Fluorenylmethoxycarbonyl Trt=Trityl, Triphenylmethyl tBu=tertiary butyl Boc=tertiary butyloxycarbonyl Pmc=2,2,5,7,8-Pentamethylchroman-6-sulphonyl TBTU=2-(1H-Benzotriazole-1-yl)-1,1,3,3-tetramethyluronium tetrafluoroborate HOBt=N-Hydroxybenzotriazole DIPEA=Diisopropylethylamine DMF=N,N Dimethylformamide EDT=Ethanedithiol TES=Triethylsilane TFA=Trifluoroacetic acid RP-HPLC=Reverse phase high performance liquid chromatography MALDI-TOF=Matrix assisted laser desorption ionisation—time of flight AAA=Amino acid analysis Fmoc-Lys(Fmoc)-OH=α,ε di-9-fluorenylmethoxycarbonyl lysine The following peptides were synthesized in this manner:

| (1) Angiotensin I-gly-cys | Asp-Arg-Val-Tyr-Ile-His-Pro-Phe-His-Leu-Gly-Cys (SEQ ID NO: 3) |
|---|---|
| (2) Angiotensin II-gly-cys | Asp-Arg-Val-Tyr-Ile-His-Pro-Phe-Gly-Cys (SEQ ID NO: 4) |
| (3) N-acetyl-Cys-Gly-Angiotensin I | N-acetyl-Cys-Gly-Asp-Arg-Val-Tyr-Ile-His-Pro-Phe-His-Leu (SEQ ID NO: 29) |
| (4) N-acetyl-Cys-Gly-Angiotensin II | N-acetyl-Cys-Gly-Asp-Arg-Val-Tyr-Ile-His-Pro-Phe (SEQ ID NO: 30) |

EXAMPLE 2

Conjugation Procedure

To tetanus toxoid solution in phosphate buffered saline (PBS), a 60 molar excess of S-MBS, m-Maleimidobenzoyl-N-hydroxysulphosuccinimide ester is added and stirred for 2 hours at 40° C. in a sealed vial.

Excess S-MBS crosslinker is removed by chromatography (gel exclusion, PD-10, G-25 sephadex column) in PBS. The activated tetanus toxoid peak is collected, assayed for free maleimido groups and used as below.

The resulting carrier protein solution is purged with $N_2$, and a 12 molar excess of angiotensin derivative peptide added. The resulting solution is stirred for 4 hours at 20° C. in a sealed container.

The conjugate is purified from free peptide by gel exclusion chromatography as above. A final assay for loss of free maleimido groups is performed on a sample of the mixture to prove that all available sites are conjugated.

The final conjugate is diluted to a working concentration and formulated as desired.

The structure of S-MBS crosslinked conjugate with a linear C-terminal extended angiotensin peptide derivative (eg. derivatives (1) and (2) of Example 1) is shown below:

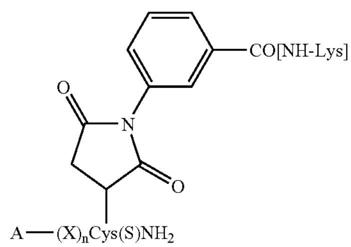

Following this procedure, angiotensin derivatives (1) to (4) of Example 1 were conjugated individually to aliquots of tetanus toxoid.

EXAMPLE 3

Immunisation Studies

The four angiotensin derivatives of Example 1, conjugated individually to aliquots of tetanus toxoid as described in Example 2, were formulated by adsorption to 0.4% (w/v) aluminium hydroxide gel (Alhydrogel, Superfos s/a, Denmark) in a normal saline (0.9% (w/v)) vehicle.

All conjugates were used as 10 μg/ml peptide equivalent solution.

Male Sprague-Dawley rats were used in 5 treatment groups, with 6 rats per group.

The treatment groups received:

| | |
|---|---|
| Vehicle, sterile saline | 0.5 ml/rat |
| N-acetyl-cys-gly-Angiotensin I derivative immunotherapeutic | 5 μg peptide equivalent/ rat in 0.5 ml vehicle |
| Angiotensin I-gly-cys derivative immunotherapeutic | 5 μg peptide equivalent/ rat in 0.5 ml vehicle |
| N-acetyl-cys-gly-Angiotensin II derivative immunotherapeutic | 5 μg peptide equivalent/ rat in 0.5 ml vehicle |
| Angiotensin II-gly-cys derivative immunotherapeutic | 5 μg peptide equivalent/ rat |

The route used was subcutaneous and each rat received 3 separate doses of the specified test article during the course of the study.

The bodyweight of each rat is recorded once a week throughout the experimental procedure.

Experimental Procedure

In this initial investigation the core temperature of each rat was recorded, as part of the general physiological monitoring of the animals.

On day 1 and subsequently on days 22 and 43, the rats received a single subcutaneous dose of the vehicle, or the test articles. Twenty four hours following each administration (days 2, 23 and 44) and on further days specified in table 1 a venous blood sample (0.5 ml) was subsequently taken while the rat was restrained.

Each sample of venous blood was collected in a glass tube, cooled on ice and allowed to clot, then centrifuged to yield serum within 45 minutes of sampling. Serum samples were frozen at approximately −20° C. as soon as possible.

TABLE 1

Time Schedule of Study Procedures

| Week | Day | Treatment | Blood Sample |
|---|---|---|---|
| 1 | 1 | Test articles, vehicle | |
| | 2 | No dosing | + |
| 2 | 9 | No dosing | + |
| | 16 | No dosing | + |
| 3 | 22 | Test articles, vehicle | |
| | 23 | No dosing | + |
| 4 | 30 | No dosing | + |
| 5 | 37 | No dosing | + |
| 6 | 43 | Test articles, vehicle | |
| | 44 | No dosing | + |
| 7 | 51 | No dosing | + |
| 8 | 58 | No dosing | + |
| 9 | 65 | No dosing | + |
| 10 | 72 | No dosing | + |
| 11 | 79 | No dosing | + |
| 12 | 86 | No dosing | + |

Each serum sample was assayed for the generation by the treatment of an antibody response by titration of anti-angiotensin peptide-antibodies-present in the sera by Enzyme Linked ImmunoSorbant Assay (ELISA).

This assay was performed as follows:

Coat the 96 well uniwell microtitre plates with 50 μl detection substrate e.g. Angiotensin II-Gly-Cys-BSA (10 μg peptide equivalent/well) for 1 hour at room temperature. At the same time place 50 μl PBS into separate wells to act as a substrate blank.

Wash the plates 3 times with 200 μl Phosphate Buffered Saline (PBS)/0.1% Tween 20.

Add 200 μl/well of 3% (w/v) milk powder (Marvel) in PBS and leave for 1 hour at room temperature to block non-specific antibody binding.

Wash the plates 3 times with 200 μl PBS/0.1% Tween 20.

Dilute the serum samples to a suitable dilution with PBS. Typical dilutions would be as follows:

i) 1/100–5 μl rats sera+495 μl PBS ii) 1/1000–20 μl (i)+180 μl PBS iii) 1/2000–10 μl (i)+190 μl PBS iv) 1/5000–4 μl (i)+196 μl PBS Load the appropriate diluted sera (50 μl) to appropriate wells and incubate at 20° C. for 1 hour to permit substrate: antibody binding.

Wash the plates 3 times with 200 μl PBS/0.1% Tween 20.

Dilute rabbit anti-rat IgG peroxidase conjugate 1:5000 in PBS i.e. 1 μl IgG peroxidase+5 mls PBS. This binds to the rat serum antibody and allows antibody detection.

Add 50 μl of the diluted IgG peroxidase to the appropriate wells and leave for 45 minutes at room temperature.

Wash the plates 3 times with 200 μl PBS.

250 μl aliquot of the perodidase substrate 3,3$^1$, 5,5$^1$,-tetra methyl benzidine (TMB) to 25 mls 0.1M sodium acetate buffer pH5.5 with 4 μl 30% hydrogen peroxide.

Add 100 μl of the prepared TMB substrate to the appropriate wells, including the blank wells. A colour producing reaction occurs where antibody/substrate binding has occurred. Leave for 15 minutes at room temperature, then terminate the reaction with 50 μl 10% sulphuric acid added to each well.

The plate was read for absorbance of light at 405 nm generated by the reaction of the peroxidase enzyme on the TMB substrate and is proportional to the amount of primary (anti-angiotensin) antibody bond. Results for the 4 sample conjugate formulations of derivatives (1) to (4) of Example 1 are shown in FIG. 1.

FIG. 1 shows a time course of mean antibody titre (+/−Sem, n=6) on the y axis at different sample times, measured in days on the x axis. The titre is the SAS estimated dilution of serum required for a 0.1 OD change from baseline levels in the ELISA assay.

The changes in antibody levels against angiotensin peptides can be seen over time, and are summarised below:

| Immunogen | Peak titre | Day | Terminal titre (Day 86) |
|---|---|---|---|
| (B) N-acetyl-cys-gly-Angiotensin I | 12,218 ± 3576 | 86 | As peak |
| (C) Angiotensin I-gly-cys | 9,535 ± 4423 | 30 | 5068 ± 2038 |
| (D) N-acetyl-cys-gly-Angiotensin II | 15,726 ± 8271 | 30 | 10,239 ± 6544 |
| (E) Angiotensin II-gly-cys | 5090 ± 2965 | 37 | 2011 ± 1250 |

(A) is the control

In parallel with the antibody titre data, all animals were examined for gross physiological changes in body temperature, weight and general appearance, as an overall assessment of toxic or harmful effects.

No adverse effects were recorded on any of the 4 angiotensin immunoconjugate treatment groups, showing that the treatments are effective in generating anti-angiotensin antibodies, without harmful physiological effects in the animals.

EXAMPLE 4

Effects of Active Immunisation Against Angiotensin Peptides on the Pressor Effects of Exogenous Angiotensin I (AI) in Conscious Rats In this experiment to demonstrate the potential of active immunisation with angiotensin analogues, certain analogues of angiotensin I (AI) and angiotensin II (AII) were conjugated to carrier proteins which are good immunogens. These immunoconjugates were adjuvanted and shown in immunised rats to generate a strong anti-angiotensin immune response.

The immunised rats were examined with regard to inhibition of the pressor response to exogenous AI.

Materials and Methods

Angiotensin Immunotherapeutic Vaccine Preparation

The angiotensin analogues used in this study were:

AI analogue is: N-acetyl-cysteine-glycine-angiotensin I

AII analogue is: N-acetyl-cysteine-glycine-angiotensin II

The analogues of AI and AII were prepared using a Symphony peptide synthesiser (Anachem).

The conjugation carrier proteins, tetanus toxoid (TT) (Chiron Behring, GmbH), keyhole limpet hemocyanin (KLH) (Biosyn, GmbH) and non toxic recombinant diphtheria toxin (DT) (Chiron Behring, GmbH), were activated using a suitable bivalent linker. The 'activated' carrier protein was separated from the excess cross-linker reagent by size exclusion chromatography.

The following conjugates were made

| Sample Group | Conjugate |
|---|---|
| A | Saline control |
| B | AII analogue, TT carrier protein |
| C | AI analogue, TT carrier protein |
| D | AII analogue, DT carrier protein |
| E | AII analogue, KLH carrier protein |
| F | AII analogue, TT carrier protein |
| G | equal mix of AI and AII analogues TT carrier protein |
| H | AII analogue, TT carrier protein |
| J | AI analogue, TT carrier protein |
| K | AII analogue, TT carrier protein |
| L | AI analogue, TT carrier protein |

Key:
AI/AII Peptide analogues of angiotensin hormones
TT Tetanus toxoid
DT non-toxic recombinant Diphtheria toxin
KLH Keyhole Limpet Haemocyanin An excess of the AI and/or AII analogues was mixed with the activated carrier proteins and allowed to react, after which AI/AII-carrier protein conjugates were separated from the remaining free analogue by size exclusion chromatography.

The conjugates were sterilised by filtration through a 0.2 μm filter (Millipore) and formulated with adjuvant and saline vehicle to yield the appropriate vaccine for administration.

Alhydrogel® (Superfos S.A.) was the chosen aluminium hydroxide gel adjuvant for this study and 0.9% saline (Flowfusor®, Fresenius) the vaccine vehicle.

Table 2 shows the conjugate formulations administered to each of the treatment groups. The conjugates were formulated with aluminium hydroxide adjuvant, other than the conjugate of Group F which was formulated with DEAE (diethylaminoethyl)-dextran adjuvant.

Immunisation and AI Challenge

Male, Sprague Dawley rats (initially 200-250 g: Harlan Olac: n=6 for all groups) were injected (0.5 ml, sc.) with saline or immunotherapeutic vaccines on the days specified in Table 2.

On day 61, under sodium methohexitone anaesthesia (40-60 mg kg$^{-1}$ i.p., supplemented as required), catheters were implanted in the distal abdominal aorta (via the ventral caudal artery) and right jugular vein. The following day, conscious rats were given increasing i.v. bolus (0.1 ml) doses of AI (3-60 pmol rat$^{-1}$), while mean systemic arterial blood pressure and heart rate were recorded. At the end of the experiment animals were given i.v. sodium pentobarbitone (100 mg) and a blood sample was taken by cardiac puncture for the measurement of anti-angiotensin antibodies by ELISA.

TABLE 2

Treatment regime, formulations, doses, injection frequency and experimental regimes for study

| | | | Injections | | | | | Catheters | Challenge (AI) |
|---|---|---|---|---|---|---|---|---|---|
| | | | Days | | | | | | |
| Group | Formulation | Vol/Dose | 0 | 14 | 21 | 28 | 42 | 61 | 62 |
| A | Saline Control | 0.2 ml | X | | X | | X | X | X |
| B | AII analogue, TT carrier protein, AlOH adjuvant | 5 µg | X | | X | | X | X | X |
| C | AI analogue, TT carrier protein, AlOH adjuvant | 5 µg | X | | X | | X | X | X |
| D | AII analogue, DT carrier protein, AlOH adjuvant | 5 µg | X | | X | | X | X | X |
| E | AII analogue, KLH carrier protein, AlOH adjuvant | 5 µg | X | | X | | X | X | X |
| F | AII analogue, TT carrier protein, DEAE adjuvant | 5 µg | X | | X | | X | X | X |
| G | equal mix of AI and AII analogues TT carrier protein, AlOH adjuvant | 2 × 2.5 µg | X | | X | | X | X | X |
| H | AII analogue, TT carrier protein, AlOH adjuvant | 25 µg | X | | X | | X | X | X |
| J | AI analogue, TT carrier protein, AlOH adjuvant | 25 µg | X | | X | | X | X | X |
| K | AII analogue, TT carrier protein, AlOH adjuvant | 5 µg | X | X | | X | | X | X |
| L | AI analogue, TT carrier protein, AlOH adjuvant | 5 µg | X | X | | X | | X | X |

Key:
AI/AII Peptide analogues of angiotensin hormones
TT Tetanus toxoid
DT non-toxic recombinant Diphtheria toxin
KLH Keyhole Limpet Haemocyanin
DEAE Diethylaminoethyl cellulose
AlOH Aluminium hydroxide gel Angiotensin Analogue Antibody ELISA ELISA plate wells (Anachem) were coated with 10 µg peptide equivalents of either AI or AII conjugated to bovine serum albumin (BSA) as a carrier.

The coated wells were washed with PBS (0.2% w/v)/Tween (Sigma) and blocked with 3% Marvel before diluted sera from the vaccinated rats were incubated in their respective wells. The sera had been diluted in PBS (Sigma) over a range from 2,500-20,000 fold.

Immobilised antibodies were detected in the wells using a rabbit anti-rat IgG/horseradish peroxidase conjugate and revealed using 3,3'-5,5'-tetra-methyl benzidine with $H_2O_2$ (Sigma). The reaction was terminated after 15 min at 22° C. by the addition of 10% (v/v) $H_2SO_4$ (Sigma).

Colour generated was determined by absorbance at 450 nm using a Packard plate reader. The resultant absorbance readings were analysed by a statistical package (SAS Institute 1997) to determine titre.

Statistical Analysis of Blood Pressure Changes on AI Challenge

The maximum change in mean blood pressure and heart rate over their immediate pre-challenge values were calculated for each animal and each challenge dose. Differences between treated groups and unimmunised controls were assessed by ANOVA using Dunnett's test.

Dose Response Analysis

The main effect of immunisation was to cause a parallel shift in the blood pressure dose response of animals to AI challenge. To estimate the size of this shift, a logistic model was derived and fitted to the dose response:

$$\Delta BP = \frac{\Delta BP_{max}}{1 + (d/ED50)^{-\alpha}} + \varepsilon \quad \varepsilon \sim N(0, \sigma^2)$$

where d is the dose of AI, $BP_{max}$ is the maximal change in blood pressure, $\alpha$ a shape parameter and $ED_{50}$ is the dose of AI giving a half maximal response. Separate $ED_{50}$ estimates were obtained for each animal. Significant differences between treatment groups and unimmunised controls were assessed by ANOVA of log-transformed $ED_{50}$ values using Dunnett's multiple comparison test.

Results

Table 3 summarises some of the results, showing that active immunisation caused significant shifts in the pressor dose-response to AI and marked increases in antibody titres.

Clear effects on blood pressure are demonstrated with these treatments and the maximum dose shift (8.9× the control) are seen with a conjugate containing the AI analogue and tetanus toxoid on an aluminium hydroxide adjuvant.

Table 3 also demonstrates the relationship between anti-angiotensin antibody titre and response. In general, it can be seen that there is broad agreement between treatment induced titre and mean treatment induced dose shift, but no obvious dose response between groups C and J is apparent.

Figure 2:
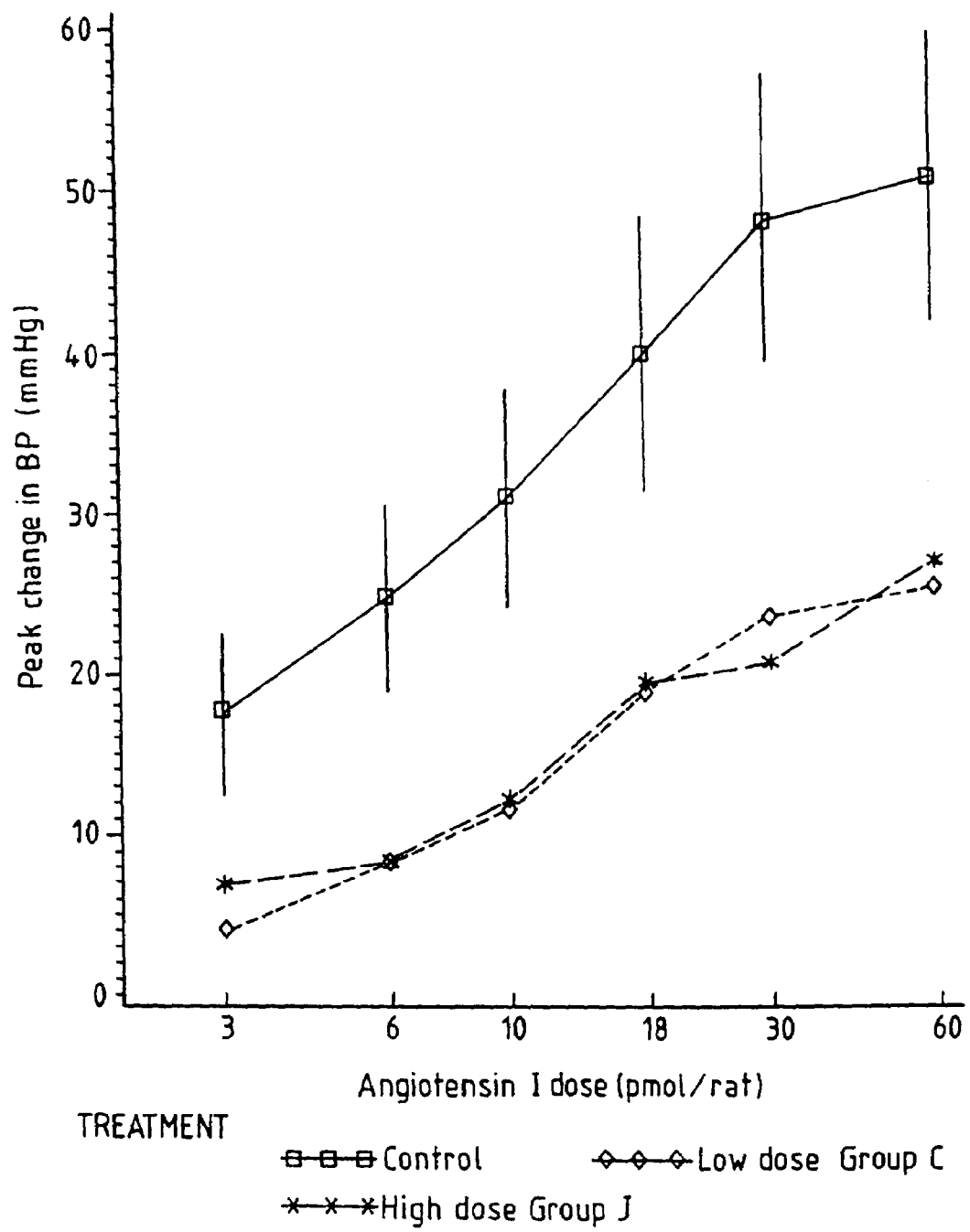
FIG. 2 is a graph showing peak change in blood pressure following administration of AI in control rats and in rats immunised with a conjugate of an analogue of AI in groups C and J of Example 4.
Figure 3:
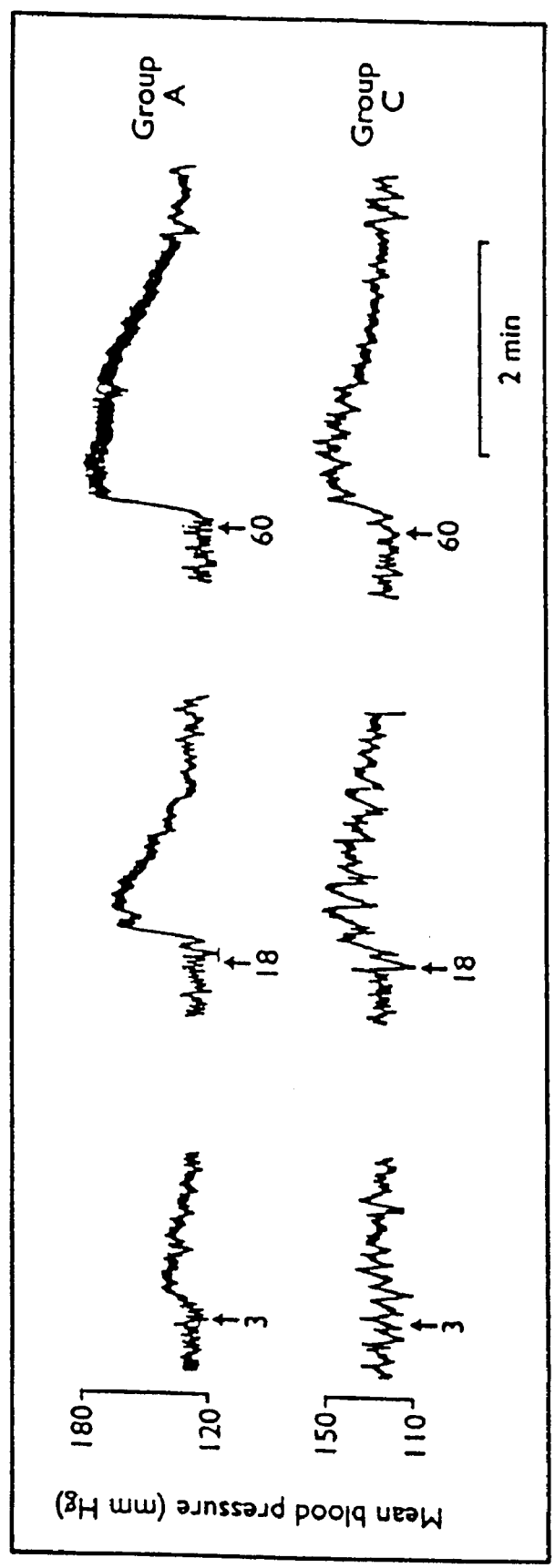
FIG. 3 shows recordings of mean blood pressure changes in response to AI in animals of groups A and C of Example 4.

FIGS. 2 and 3 illustrate the results for control rats (Group A) and rats immunised with a conjugate of the AI analogue and tetanus toxoid, presented on an AlOH gel adjuvant at a peptide equivalent dose of 5 µg (low; Group C) and 25 µg (high; Group J).

FIG. 2 is a graph showing pressor effects of AI in control rats (Group A) and rats immunised with AI analogue at a dose of 5 µg (low, Group C) or 25 µg (High, Group J). The y axis shows peak change in BP (mm Hg) and the x axis shows the angiotensin I dose (pmol/rat) in control, high dose group J (25 µg) and low dose group C (5 µg) animals. Errors bars shows 95% confidence interval on mean, based on pooled within group standard deviation (n=6), shown for control group only.

FIG. 3 shows recordings of mean blood pressure changes in response to AI (3, 18 and 60 pmol bolus dose) in representative animals from group A (control) and Group C (5 µg dose).

Conclusion

Treatment with a conjugate containing an Al analogue and tetanus toxoid on an aluminium hydroxide adjuvant gives a highly significant reduction in the pressor response to exogenous Al.

TABLE 3

| Treatment | Median $ED_{50}$ | Mean treatment-induced dose shift | Anti-angiotensin antibody titre, ± s.e. mean (n = 6) |
|---|---|---|---|
| A | 8.9  | —     | 0 0          |
| B | 39.6 | 4.5*  | 15300 ± 2100 |
| C | 79.1 | 8.9***| 32100 ± 7800 |
| D | 19.6 | 2.2   | 9200 ± 2200  |
| E | 17.6 | 2.0   | 4700 ± 600   |
| F | 15.2 | 1.7   | 5500 ± 700   |
| G | 24.5 | 2.8   | 8300 ± 2000  |
| H | 38.2 | 4.3*  | 12100 ± 2500 |
| J | 74.7 | 8.4***| 20100 ± 2300 |
| K | 13.9 | 1.6   | 5000 ± 900   |
| L | 43.0 | 4.8*  | 26100 ± 9400 |

Median AI bolus (pmol.rat$^{-1}$) to achieve half-maximal increase in mean blood pressure ($ED_{50}$) and corresponding anti-angiotensin antibody titres in control (group A) and immunised (groups B-L) rats. Significance probabilities adjusted for multiple comparisons by Dunnett's method (*=P<0.05, =P<0.01, *=P<0.001).

EXAMPLE 5

Characterisation of Antibodies Produced in Example 3

Antibodies produced in Example 3 were enriched by affinity chromatography as follows:

Materials 1 mL HiTrap protein G affinity column (Pharmacia Biotech: 17-0404-03)

Wash buffer (WB)=PBS pH 7.2

Elution buffer (EB)=0.1M glycine (HCL) pH 2.7

Neutralizing buffer (NB)=1M Tris (HCL) pH 9

Storage buffer (SB)=20% ethanol (v/v)

1. Rat sera from terminal bleeds following inoculation with each of TT-NAc-CG-angiotensin I (5 mL), angiotensin I-GC-TT (7 mL), TT-NAc-CG-angiotensin II (6 mL) or angiotensin II-GC-TT (5 mL), were clarified by centrifugation, filtered through a 1 µm PTFE disc filter then dialyzed against PBS pH 7.2. Each was then separately enriched as follows.
2. The HiTrap column was washed and equilibrated with 5 mL of WB.
3. Prepared sera (Point 1) was passed once through the HiTrap column, the waste was collected and stored at −20° C.
4. The HiTrap column was washed with 5 mL of WB to remove any remaining waste sera.
5. Immobilized antibodies were eluted using 10 mL of EB. The eluent was collected in 1 ml fractions each being immediately neutralized with 0.1 mL of
6. At the end of the run the HiTrap column was washed with SB and stored at 4° C.

ELISA assays were carried out as described in Example 3 using plates coated as follows:

1) for angiotensin I and II

Materials:

Nunc Maxisorp ELISA plates (Life Technologies: 430341A).

Human Angiotensin I (Bachem: H-1680)

Human Angiotensin II (Bachem: H-1705)

0.1M carbonate buffer, pH 9.8 (0.316 g $Na_2CO_3$ & 0.584 g $NaHCO_3$ per 0.1.)

Other materials used were as in the ELISA method detailed in Example 3 above.

1. 100 µL of either angiotensin I or angiotensin II, depending on the specific binding event to be measured @ 0.2 mg/ml of 0.1M carbonate buffer, pH 9.8) was added to a suitable number of ELISA plate wells, and incubated for 1 hour at 22° C.
2. The ELISA plate was washed with PBS/Tween, blocked with Marvel then washed with PBS/Tween again as by the ELISA method described in Example 3 above.
3. The enriched antibodies from sera raised to Tetanus toxoid (TT) conjugates TT-NAc-CG-Ang I, Ang I-GC-TT, TT-NAc-CG-Ang II and Ang II-GC-TT, were incubated (1 hour, 22° C.) in the coated wells at 2.5 µg/ml of PBS pH 7.2.

The ELISA was then completed as by the method described in Example 3 but absorbance was read at 450 nm.

2) For angiotensinogen:

The ELISA for detection of native angiotensinogen (Sigma: A-2562) was performed by the method of Example 3.

The enriched antibodies from sera raised to Tetanus Toxoid (TT) conjugates TT-NAc-CG-Ang I, Ang I-GC-TT, TT-NAc-CG-Ang II and Ang II-GC-TT were incubated (1 hour 22° C.) at 0.5 µg/ml of PBS pH 7.2.

Figure 4:
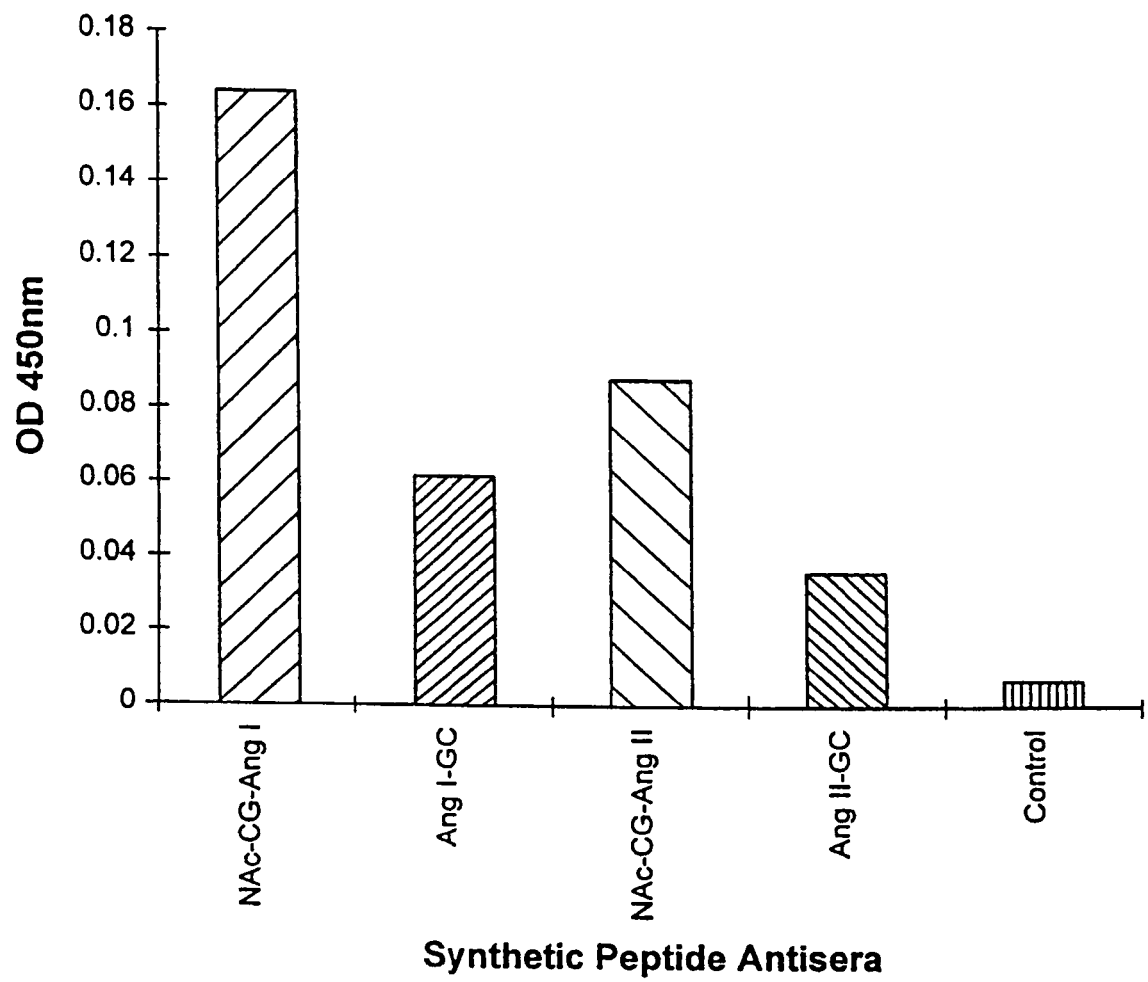
FIGS. 4, 5 and 6 are bar charts showing antibody titres measured in terms of $A^{450}$ in an ELISA assay using in the assay in FIG. 4 angiotensin I, in FIG. 5 angiotensin II and in FIG. 6 angiotensinogen, the ELISAs showing the binding of partially purified rat antisera raised against vaccines containing analogues of angiotensin hormones.
Figure 5:
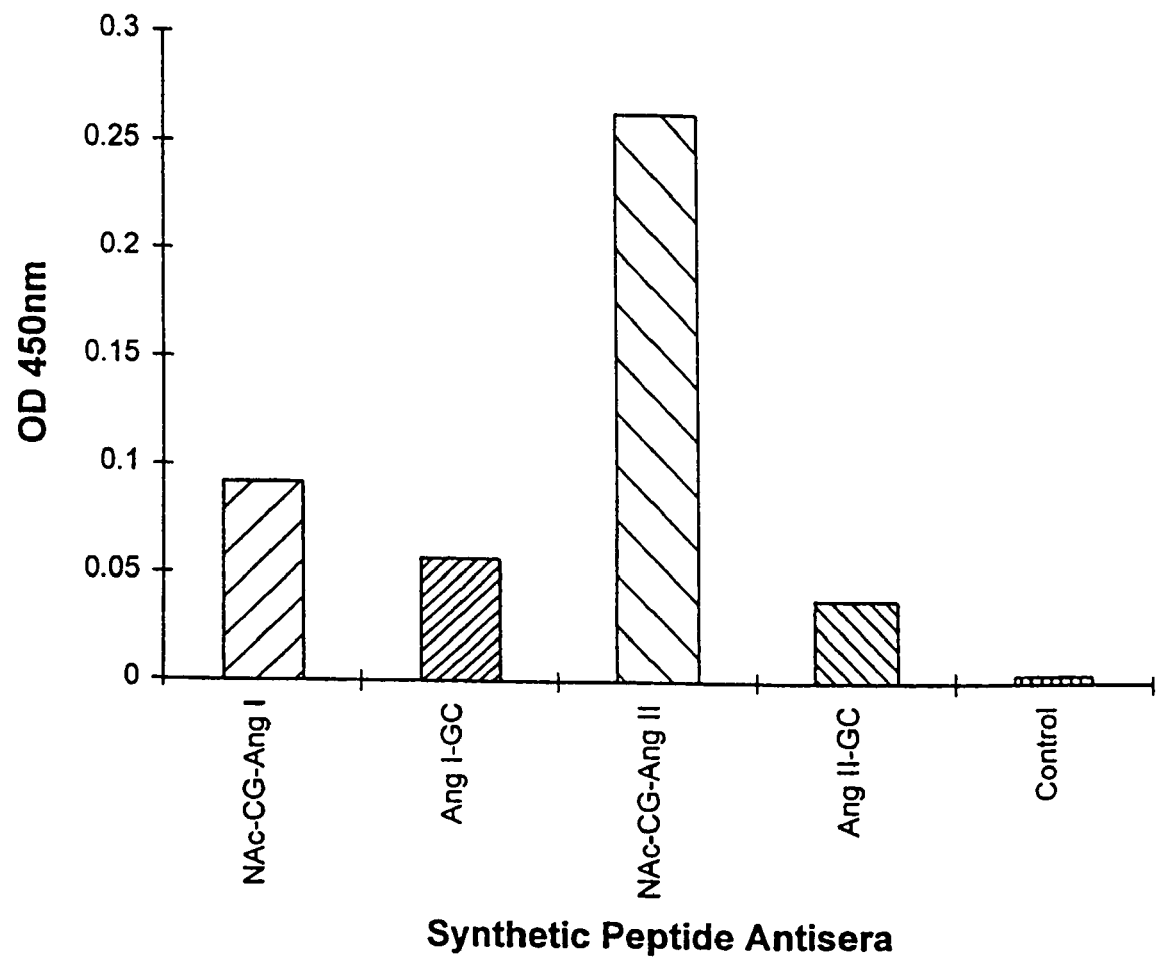
Figure 6:
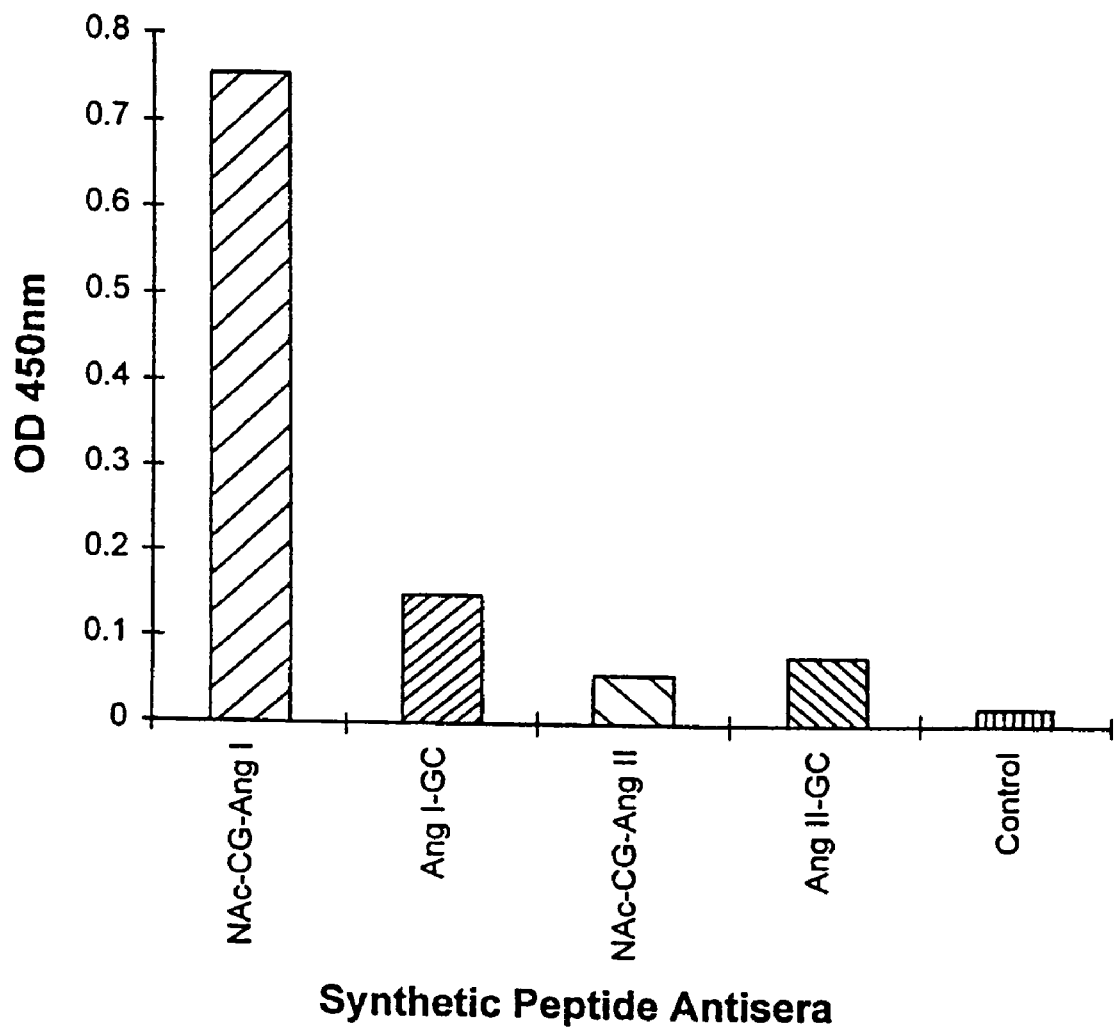

Results are shown in FIGS. 4, 5 and 6 which show absorbance read with ELISA plates coated with angiotensin I (FIG. 4), angiotensin II (FIG. 5) and angiotensinogen (FIG. 6) and shows that antibodies raised to each of the angiotensin derivatives conjugated to TT ie TT-NAc-CG-Ang I, Ang I-GC-TT, TT-NAc-CG-Ang II and Ang II-GC-TT recognised angiotensin I, angiotensin II and angiotensinogen.

EXAMPLE 6

Generation of Further Angiotensin Derivatives and Immunisation Studies

The following angiotensin derivative peptides 1-6 were synthesised according to the method of Example 1

| | |
|---|---|
| N-acetyl-Cys-Ala-Angiotensin I (SEQ ID NO: 21) | (1) |
| N-acetyl-Cys-(Ala)₄-Angiotensin I (SEQ ID NO: 24) | (2) |
| N-acetyl-Cys(Gly)₆-Angiotensin I (SEQ ID NO: 25) | (3) |
| N-acetyl-Cys-Gly-Ala-Gly-Ala-Angiotensin I (SEQ ID NO: 27) | (4) |
| Angiotensin I<br>                    Lys<br>Angiotensin I<br>Angiotensin I<br>                    Lys<br>Angiotensin I              Lys-Gly-Cys<br>Angiotensin I<br>                    Lys<br>Angiotensin I | (5)<br><br><br><br>(6) |

These peptides were conjugated to tetanus toxoid as described in Example 2, and formulated for immunisation studies using the protocol described in Example 3.

Antibody titres were measured using the ELISA technique described in Example 4 against the peptides used in the immunogen.

Figure 7:
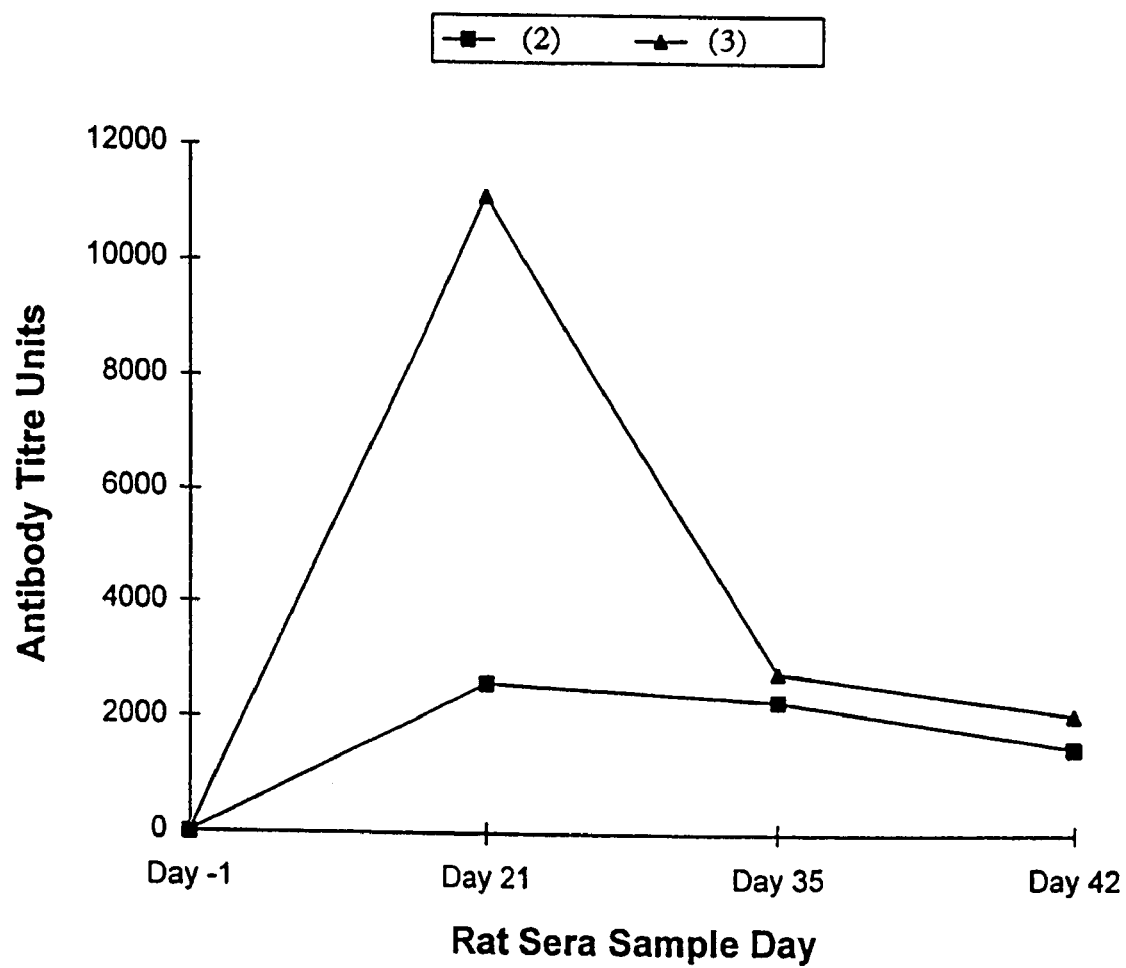
FIGS. 7 and 8 are graphs showing antibody titres against time (sample day) for the following derivatives
N-acetyl-Cys-(Ala)$_4$-Angiotensin I (SEQ ID No: 23)
N-acetyl-Cys(Gly)$_6$-Angiotensin I (SEQ ID NO: 25)
Figure 8:
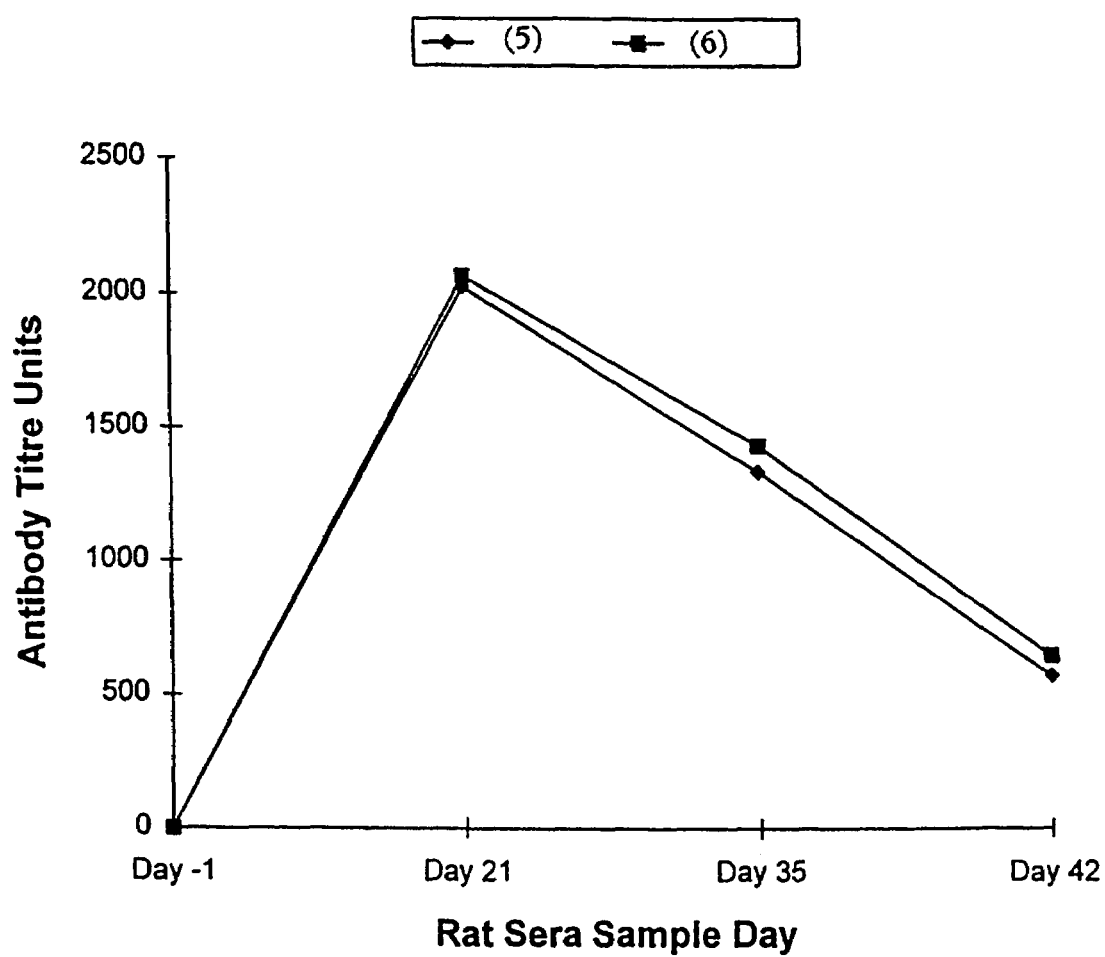

Results are shown in FIGS. 7 and 8 which are graphs showing, on the y axis the antibody titre, as the dilution factor to produce a SAS™ (Statistics Analysis System) designated 0.1 OD unit change, at various sample days. Each data point shown represents the mean of 5 serum samples from 5 different animals, each assayed in duplicate.

All peptides were shown to be effective in generating an anti-angiotensin I response. The responses varied in extent and duration.

The invention claimed is:

1. A polypeptide immunogen capable when conjugated to a carrier of inducing antibodies in an immunized subject, which antibodies recognize epitopes of angiotensin I, angiotensin II and/or angiotensinogen, said immunogen comprising an angiotensin derivative which is:

N-acetyl-Cys-Gly-(A) (SEQ ID NO: 29);

where A is angiotensin I (SEQ ID NO: 1).

2. An immunogen as claimed in claim 1 comprising said angiotensin derivative coupled to m-maleimidobenzoyl-N-hydroxysulphosuccinimide ester.

* * * * *

SEQUENCE LISTING

```
<160> NUMBER OF SEQ ID NOS: 331

<210> SEQ ID NO 1
<211> LENGTH: 10
<212> TYPE: PRT
<213> ORGANISM: Unknown
<220> FEATURE:
<223> OTHER INFORMATION: mammalian peptide hormone angiotensin I

<400> SEQUENCE: 1

Asp Arg Val Tyr Ile His Pro Phe His Leu
1               5                   10

<210> SEQ ID NO 2
<211> LENGTH: 8
<212> TYPE: PRT
<213> ORGANISM: Unknown
<220> FEATURE:
<223> OTHER INFORMATION: mammalian peptide hormone angiotensin II

<400> SEQUENCE: 2

Asp Arg Val Tyr Ile His Pro Phe
1               5

<210> SEQ ID NO 3
<211> LENGTH: 12
<212> TYPE: PRT
<213> ORGANISM: Unknown
<220> FEATURE:
<223> OTHER INFORMATION: Angiotensin I derivative

<400> SEQUENCE: 3

Asp Arg Val Tyr Ile His Pro Phe His Leu Gly Cys
1               5                   10

<210> SEQ ID NO 4
<211> LENGTH: 10
<212> TYPE: PRT
<213> ORGANISM: Unknown
<220> FEATURE:
<223> OTHER INFORMATION: Angiotensin II derivative

<400> SEQUENCE: 4

Asp Arg Val Tyr Ile His Pro Phe Gly Cys
1               5                   10

<210> SEQ ID NO 5
```

```
<211> LENGTH: 11
<212> TYPE: PRT
<213> ORGANISM: Unknown
<220> FEATURE:
<223> OTHER INFORMATION: Angiotensin I derivative

<400> SEQUENCE: 5

Asp Arg Val Tyr Ile His Pro Phe His Leu Cys
1               5                   10

<210> SEQ ID NO 6
<211> LENGTH: 11
<212> TYPE: PRT
<213> ORGANISM: Unknown
<220> FEATURE:
<223> OTHER INFORMATION: Angiotensin I derivative

<400> SEQUENCE: 6

Asp Arg Val Tyr Ile His Pro Phe His Leu Tyr
1               5                   10

<210> SEQ ID NO 7
<211> LENGTH: 11
<212> TYPE: PRT
<213> ORGANISM: Unknown
<220> FEATURE:
<223> OTHER INFORMATION: Angiotensin I derivative

<400> SEQUENCE: 7

Tyr Asp Arg Val Tyr Ile His Pro Phe His Leu
1               5                   10

<210> SEQ ID NO 8
<211> LENGTH: 11
<212> TYPE: PRT
<213> ORGANISM: Unknown
<220> FEATURE:
<223> OTHER INFORMATION: Angiotensin I derivative

<400> SEQUENCE: 8

Cys Asp Arg Val Tyr Ile His Pro Phe His Leu
1               5                   10

<210> SEQ ID NO 9
<211> LENGTH: 12
<212> TYPE: PRT
<213> ORGANISM: Unknown
<220> FEATURE:
<223> OTHER INFORMATION: Angiotensin I derivative

<400> SEQUENCE: 9

Asp Arg Val Tyr Ile His Pro Phe His Leu Gly Cys
1               5                   10

<210> SEQ ID NO 10
<211> LENGTH: 10
<212> TYPE: PRT
<213> ORGANISM: Unknown
<220> FEATURE:
<223> OTHER INFORMATION: Angiotensin II derivative

<400> SEQUENCE: 10

Asp Arg Val Tyr Ile His Pro Phe Gly Cys
1               5                   10

<210> SEQ ID NO 11
<211> LENGTH: 12
```

```
<212> TYPE: PRT
<213> ORGANISM: Unknown
<220> FEATURE:
<223> OTHER INFORMATION: Angiotensin I derivative

<400> SEQUENCE: 11

Cys Gly Asp Arg Val Tyr Ile His Pro Phe His Leu
1               5                   10

<210> SEQ ID NO 12
<211> LENGTH: 10
<212> TYPE: PRT
<213> ORGANISM: Unknown
<220> FEATURE:
<223> OTHER INFORMATION: Angiotensin II derivative

<400> SEQUENCE: 12

Cys Gly Asp Arg Val Tyr Ile His Pro Phe
1               5                   10

<210> SEQ ID NO 13
<211> LENGTH: 23
<212> TYPE: PRT
<213> ORGANISM: Unknown
<220> FEATURE:
<223> OTHER INFORMATION: Angiotensin derivative

<400> SEQUENCE: 13

Asp Arg Val Tyr Ile His Pro Phe His Leu Gly Cys Gly Asp Arg Val
1               5                   10                  15

Tyr Ile His Pro Phe His Leu
            20

<210> SEQ ID NO 14
<211> LENGTH: 21
<212> TYPE: PRT
<213> ORGANISM: Unknown
<220> FEATURE:
<223> OTHER INFORMATION: Angiotensin derivative

<400> SEQUENCE: 14

Asp Arg Val Tyr Ile His Pro Phe His Leu Gly Cys Gly Asp Arg Val
1               5                   10                  15

Tyr Ile His Pro Phe
            20

<210> SEQ ID NO 15
<211> LENGTH: 23
<212> TYPE: PRT
<213> ORGANISM: Unknown
<220> FEATURE:
<223> OTHER INFORMATION: Angiotensin derivative

<400> SEQUENCE: 15

Leu His Phe Pro His Ile Tyr Val Arg Asp Gly Cys Gly Asp Arg Val
1               5                   10                  15

Tyr Ile His Pro Phe His Leu
            20

<210> SEQ ID NO 16
<211> LENGTH: 21
<212> TYPE: PRT
<213> ORGANISM: Unknown
<220> FEATURE:
<223> OTHER INFORMATION: Angiotensin derivative
```

```
<400> SEQUENCE: 16

Leu His Phe Pro His Ile Tyr Val Arg Asp Gly Cys Gly Asp Arg Val
1               5                   10                  15

Tyr Ile His Pro Phe
            20

<210> SEQ ID NO 17
<211> LENGTH: 21
<212> TYPE: PRT
<213> ORGANISM: Unknown
<220> FEATURE:
<223> OTHER INFORMATION: Angiotensin derivative

<400> SEQUENCE: 17

Asp Arg Val Tyr Ile His Pro Phe Gly Cys Gly Asp Arg Val Tyr Ile
1               5                   10                  15

His Pro Phe His Leu
            20

<210> SEQ ID NO 18
<211> LENGTH: 19
<212> TYPE: PRT
<213> ORGANISM: Unknown
<220> FEATURE:
<223> OTHER INFORMATION: Angiotensin derivative

<400> SEQUENCE: 18

Asp Arg Val Tyr Ile His Pro Phe Gly Cys Gly Asp Arg Val Tyr Ile
1               5                   10                  15

His Pro Phe

<210> SEQ ID NO 19
<211> LENGTH: 21
<212> TYPE: PRT
<213> ORGANISM: Unknown
<220> FEATURE:
<223> OTHER INFORMATION: Angiotensin derivative

<400> SEQUENCE: 19

Phe Pro His Ile Tyr Val Arg Asp Gly Cys Gly Asp Arg Val Tyr Ile
1               5                   10                  15

His Pro Phe His Leu
            20

<210> SEQ ID NO 20
<211> LENGTH: 19
<212> TYPE: PRT
<213> ORGANISM: Unknown
<220> FEATURE:
<223> OTHER INFORMATION: Angiotensin derivative

<400> SEQUENCE: 20

Phe Pro His Ile Tyr Val Arg Asp Gly Cys Gly Asp Arg Val Tyr Ile
1               5                   10                  15

His Pro Phe

<210> SEQ ID NO 21
<211> LENGTH: 12
<212> TYPE: PRT
<213> ORGANISM: Unknown
<220> FEATURE:
<223> OTHER INFORMATION: Angiotensin I derivative

<400> SEQUENCE: 21
```

Cys Ala Asp Arg Val Tyr Ile His Pro Phe His Leu
1               5                   10

<210> SEQ ID NO 22
<211> LENGTH: 10
<212> TYPE: PRT
<213> ORGANISM: Unknown
<220> FEATURE:
<223> OTHER INFORMATION: Angiotensin II derivative

<400> SEQUENCE: 22

Cys Ala Asp Arg Val Tyr Ile His Pro Phe
1               5                   10

<210> SEQ ID NO 23
<211> LENGTH: 15
<212> TYPE: PRT
<213> ORGANISM: Unknown
<220> FEATURE:
<223> OTHER INFORMATION: Angiotensin I derivative

<400> SEQUENCE: 23

Cys Ala Ala Ala Ala Asp Arg Val Tyr Ile His Pro Phe His Leu
1               5                   10                  15

<210> SEQ ID NO 24
<211> LENGTH: 13
<212> TYPE: PRT
<213> ORGANISM: Unknown
<220> FEATURE:
<223> OTHER INFORMATION: Angiotensin II derivative

<400> SEQUENCE: 24

Cys Ala Ala Ala Ala Asp Arg Val Tyr Ile His Pro Phe
1               5                   10

<210> SEQ ID NO 25
<211> LENGTH: 17
<212> TYPE: PRT
<213> ORGANISM: Unknown
<220> FEATURE:
<223> OTHER INFORMATION: Angiotensin I derivative

<400> SEQUENCE: 25

Cys Gly Gly Gly Gly Gly Gly Asp Arg Val Tyr Ile His Pro Phe His
1               5                   10                  15

Leu

<210> SEQ ID NO 26
<211> LENGTH: 15
<212> TYPE: PRT
<213> ORGANISM: Unknown
<220> FEATURE:
<223> OTHER INFORMATION: Angiotensin II derivative

<400> SEQUENCE: 26

Cys Gly Gly Gly Gly Gly Gly Asp Arg Val Tyr Ile His Pro Phe
1               5                   10                  15

<210> SEQ ID NO 27
<211> LENGTH: 15
<212> TYPE: PRT
<213> ORGANISM: Unknown
<220> FEATURE:
<223> OTHER INFORMATION: Angiotensin I derivative

```
<400> SEQUENCE: 27

Cys Gly Ala Gly Ala Asp Arg Val Tyr Ile His Pro Phe His Leu
1               5                   10                  15

<210> SEQ ID NO 28
<211> LENGTH: 13
<212> TYPE: PRT
<213> ORGANISM: Unknown
<220> FEATURE:
<223> OTHER INFORMATION: Angiotensin II derivative

<400> SEQUENCE: 28

Cys Gly Ala Gly Ala Asp Arg Val Tyr Ile His Pro Phe
1               5                   10

<210> SEQ ID NO 29
<211> LENGTH: 12
<212> TYPE: PRT
<213> ORGANISM: Unknown
<220> FEATURE:
<223> OTHER INFORMATION: Angiotensin I derivative

<400> SEQUENCE: 29

Cys Gly Asp Arg Val Tyr Ile His Pro Phe His Leu
1               5                   10

<210> SEQ ID NO 30
<211> LENGTH: 10
<212> TYPE: PRT
<213> ORGANISM: Unknown
<220> FEATURE:
<223> OTHER INFORMATION: Angiotensin II derivative

<400> SEQUENCE: 30

Cys Gly Asp Arg Val Tyr Ile His Pro Phe
1               5                   10

<210> SEQ ID NO 31
<211> LENGTH: 11
<212> TYPE: PRT
<213> ORGANISM: Unknown
<220> FEATURE:
<223> OTHER INFORMATION: Angiotensin I derivative
<220> FEATURE:
<221> NAME/KEY: MISC_FEATURE
<222> LOCATION: (10)..(11)
<223> OTHER INFORMATION: N-acetyl binding residues 10 to 11

<400> SEQUENCE: 31

Asp Arg Val Tyr Ile His Pro Phe His Leu Cys
1               5                   10

<210> SEQ ID NO 32
<211> LENGTH: 13
<212> TYPE: PRT
<213> ORGANISM: Unknown
<220> FEATURE:
<223> OTHER INFORMATION: Angiotensin I derivative

<400> SEQUENCE: 32

Asp Arg Val Tyr Ile His Pro Phe His Leu Gly Gly Cys
1               5                   10

<210> SEQ ID NO 33
<211> LENGTH: 14
<212> TYPE: PRT
<213> ORGANISM: Unknown
```

```
<220> FEATURE:
<223> OTHER INFORMATION: Angiotensin I derivative

<400> SEQUENCE: 33

Asp Arg Val Tyr Ile His Pro Phe His Leu Gly Gly Gly Cys
1               5                   10

<210> SEQ ID NO 34
<211> LENGTH: 15
<212> TYPE: PRT
<213> ORGANISM: Unknown
<220> FEATURE:
<223> OTHER INFORMATION: Angiotensin I derivative

<400> SEQUENCE: 34

Asp Arg Val Tyr Ile His Pro Phe His Leu Gly Gly Gly Gly Cys
1               5                   10                  15

<210> SEQ ID NO 35
<211> LENGTH: 16
<212> TYPE: PRT
<213> ORGANISM: Unknown
<220> FEATURE:
<223> OTHER INFORMATION: Angiotensin I derivative

<400> SEQUENCE: 35

Asp Arg Val Tyr Ile His Pro Phe His Leu Gly Gly Gly Gly Gly Cys
1               5                   10                  15

<210> SEQ ID NO 36
<211> LENGTH: 17
<212> TYPE: PRT
<213> ORGANISM: Unknown
<220> FEATURE:
<223> OTHER INFORMATION: Angiotensin I derivative

<400> SEQUENCE: 36

Asp Arg Val Tyr Ile His Pro Phe His Leu Gly Gly Gly Gly Gly
1               5                   10                  15

Cys

<210> SEQ ID NO 37
<211> LENGTH: 11
<212> TYPE: PRT
<213> ORGANISM: Unknown
<220> FEATURE:
<223> OTHER INFORMATION: Angiotensin II derivative

<400> SEQUENCE: 37

Asp Arg Val Tyr Ile His Pro Phe Gly Gly Cys
1               5                   10

<210> SEQ ID NO 38
<211> LENGTH: 12
<212> TYPE: PRT
<213> ORGANISM: Unknown
<220> FEATURE:
<223> OTHER INFORMATION: Angiotensin II derivative

<400> SEQUENCE: 38

Asp Arg Val Tyr Ile His Pro Phe Gly Gly Gly Cys
1               5                   10

<210> SEQ ID NO 39
<211> LENGTH: 13
<212> TYPE: PRT
```

```
<213> ORGANISM: Unknown
<220> FEATURE:
<223> OTHER INFORMATION: Angiotensin II derivative

<400> SEQUENCE: 39

Asp Arg Val Tyr Ile His Pro Phe Gly Gly Gly Gly Cys
1               5                   10

<210> SEQ ID NO 40
<211> LENGTH: 14
<212> TYPE: PRT
<213> ORGANISM: Unknown
<220> FEATURE:
<223> OTHER INFORMATION: Angiotensin II derivative

<400> SEQUENCE: 40

Asp Arg Val Tyr Ile His Pro Phe Gly Gly Gly Gly Gly Cys
1               5                   10

<210> SEQ ID NO 41
<211> LENGTH: 15
<212> TYPE: PRT
<213> ORGANISM: Unknown
<220> FEATURE:
<223> OTHER INFORMATION: Angiotensin II derivative

<400> SEQUENCE: 41

Asp Arg Val Tyr Ile His Pro Phe Gly Gly Gly Gly Gly Gly Cys
1               5                   10                  15

<210> SEQ ID NO 42
<211> LENGTH: 13
<212> TYPE: PRT
<213> ORGANISM: Unknown
<220> FEATURE:
<223> OTHER INFORMATION: Angiotensin I derivative

<400> SEQUENCE: 42

Cys Gly Gly Asp Arg Val Tyr Ile His Pro Phe His Leu
1               5                   10

<210> SEQ ID NO 43
<211> LENGTH: 14
<212> TYPE: PRT
<213> ORGANISM: Unknown
<220> FEATURE:
<223> OTHER INFORMATION: Angiotensin I derivative

<400> SEQUENCE: 43

Cys Gly Gly Gly Asp Arg Val Tyr Ile His Pro Phe His Leu
1               5                   10

<210> SEQ ID NO 44
<211> LENGTH: 15
<212> TYPE: PRT
<213> ORGANISM: Unknown
<220> FEATURE:
<223> OTHER INFORMATION: Angiotensin I derivative

<400> SEQUENCE: 44

Cys Gly Gly Gly Gly Asp Arg Val Tyr Ile His Pro Phe His Leu
1               5                   10                  15

<210> SEQ ID NO 45
<211> LENGTH: 16
<212> TYPE: PRT
<213> ORGANISM: Unknown
```

```
<220> FEATURE:
<223> OTHER INFORMATION: Angiotensin I derivative

<400> SEQUENCE: 45

Cys Gly Gly Gly Gly Asp Arg Val Tyr Ile His Pro Phe His Leu
1               5                   10                  15

<210> SEQ ID NO 46
<211> LENGTH: 17
<212> TYPE: PRT
<213> ORGANISM: Unknown
<220> FEATURE:
<223> OTHER INFORMATION: Angiotensin I derivative

<400> SEQUENCE: 46

Cys Gly Gly Gly Gly Gly Asp Arg Val Tyr Ile His Pro Phe His
1               5                   10                  15

Leu

<210> SEQ ID NO 47
<211> LENGTH: 11
<212> TYPE: PRT
<213> ORGANISM: Unknown
<220> FEATURE:
<223> OTHER INFORMATION: Angiotensin II derivative

<400> SEQUENCE: 47

Cys Gly Gly Asp Arg Val Tyr Ile His Pro Phe
1               5                   10

<210> SEQ ID NO 48
<211> LENGTH: 12
<212> TYPE: PRT
<213> ORGANISM: Unknown
<220> FEATURE:
<223> OTHER INFORMATION: Angiotensin II derivative

<400> SEQUENCE: 48

Cys Gly Gly Gly Asp Arg Val Tyr Ile His Pro Phe
1               5                   10

<210> SEQ ID NO 49
<211> LENGTH: 13
<212> TYPE: PRT
<213> ORGANISM: Unknown
<220> FEATURE:
<223> OTHER INFORMATION: Angiotensin II derivative

<400> SEQUENCE: 49

Cys Gly Gly Gly Gly Asp Arg Val Tyr Ile His Pro Phe
1               5                   10

<210> SEQ ID NO 50
<211> LENGTH: 14
<212> TYPE: PRT
<213> ORGANISM: Unknown
<220> FEATURE:
<223> OTHER INFORMATION: Angiotensin II derivative

<400> SEQUENCE: 50

Cys Gly Gly Gly Gly Gly Asp Arg Val Tyr Ile His Pro Phe
1               5                   10

<210> SEQ ID NO 51
<211> LENGTH: 15
<212> TYPE: PRT
```

<213> ORGANISM: Unknown
<220> FEATURE:
<223> OTHER INFORMATION: Angiotensin II derivative

<400> SEQUENCE: 51

Cys Gly Gly Gly Gly Gly Asp Arg Val Tyr Ile His Pro Phe
1               5                   10                  15

<210> SEQ ID NO 52
<211> LENGTH: 24
<212> TYPE: PRT
<213> ORGANISM: Unknown
<220> FEATURE:
<223> OTHER INFORMATION: Angiotensin I derivatives

<400> SEQUENCE: 52

Asp Arg Val Tyr Ile His Pro Phe His Leu Gly Cys Gly Gly Asp Arg
1               5                   10                  15

Val Tyr Ile His Pro Phe His Leu
            20

<210> SEQ ID NO 53
<211> LENGTH: 25
<212> TYPE: PRT
<213> ORGANISM: Unknown
<220> FEATURE:
<223> OTHER INFORMATION: Angiotensin derivative

<400> SEQUENCE: 53

Asp Arg Val Tyr Ile His Pro Phe His Leu Gly Cys Gly Gly Gly Asp
1               5                   10                  15

Arg Val Tyr Ile His Pro Phe His Leu
            20                  25

<210> SEQ ID NO 54
<211> LENGTH: 26
<212> TYPE: PRT
<213> ORGANISM: Unknown
<220> FEATURE:
<223> OTHER INFORMATION: Angiotensin derivative

<400> SEQUENCE: 54

Asp Arg Val Tyr Ile His Pro Phe His Leu Gly Cys Gly Gly Gly Gly
1               5                   10                  15

Asp Arg Val Tyr Ile His Pro Phe His Leu
            20                  25

<210> SEQ ID NO 55
<211> LENGTH: 27
<212> TYPE: PRT
<213> ORGANISM: Unknown
<220> FEATURE:
<223> OTHER INFORMATION: Angiotensin derivative

<400> SEQUENCE: 55

Asp Arg Val Tyr Ile His Pro Phe His Leu Gly Cys Gly Gly Gly Gly
1               5                   10                  15

Gly Asp Arg Val Tyr Ile His Pro Phe His Leu
            20                  25

<210> SEQ ID NO 56
<211> LENGTH: 28
<212> TYPE: PRT
<213> ORGANISM: Unknown
<220> FEATURE:

-continued

```
<223> OTHER INFORMATION: Angiotensin derivative

<400> SEQUENCE: 56

Asp Arg Val Tyr Ile His Pro Phe His Leu Gly Cys Gly Gly Gly
1               5                   10                  15

Gly Gly Asp Arg Val Tyr Ile His Pro Phe His Leu
            20                  25

<210> SEQ ID NO 57
<211> LENGTH: 24
<212> TYPE: PRT
<213> ORGANISM: Unknown
<220> FEATURE:
<223> OTHER INFORMATION: Angiotensin derivative

<400> SEQUENCE: 57

Asp Arg Val Tyr Ile His Pro Phe His Leu Gly Gly Cys Gly Asp Arg
1               5                   10                  15

Val Tyr Ile His Pro Phe His Leu
            20

<210> SEQ ID NO 58
<211> LENGTH: 25
<212> TYPE: PRT
<213> ORGANISM: Unknown
<220> FEATURE:
<223> OTHER INFORMATION: Angiotensin derivative

<400> SEQUENCE: 58

Asp Arg Val Tyr Ile His Pro Phe His Leu Gly Gly Cys Gly Gly Asp
1               5                   10                  15

Arg Val Tyr Ile His Pro Phe His Leu
            20                  25

<210> SEQ ID NO 59
<211> LENGTH: 26
<212> TYPE: PRT
<213> ORGANISM: Unknown
<220> FEATURE:
<223> OTHER INFORMATION: Angiotensin derivative

<400> SEQUENCE: 59

Asp Arg Val Tyr Ile His Pro Phe His Leu Gly Gly Cys Gly Gly Gly
1               5                   10                  15

Asp Arg Val Tyr Ile His Pro Phe His Leu
            20                  25

<210> SEQ ID NO 60
<211> LENGTH: 27
<212> TYPE: PRT
<213> ORGANISM: Unknown
<220> FEATURE:
<223> OTHER INFORMATION: Angiotensin derivative

<400> SEQUENCE: 60

Asp Arg Val Tyr Ile His Pro Phe His Leu Gly Gly Cys Gly Gly Gly
1               5                   10                  15

Gly Asp Arg Val Tyr Ile His Pro Phe His Leu
            20                  25

<210> SEQ ID NO 61
<211> LENGTH: 28
<212> TYPE: PRT
<213> ORGANISM: Unknown
```

-continued

```
<220> FEATURE:
<223> OTHER INFORMATION: Angiotensin derivative

<400> SEQUENCE: 61

Asp Arg Val Tyr Ile His Pro Phe His Leu Gly Gly Cys Gly Gly
1               5                   10                  15

Gly Gly Asp Arg Val Tyr Ile His Pro Phe His Leu
            20                  25

<210> SEQ ID NO 62
<211> LENGTH: 29
<212> TYPE: PRT
<213> ORGANISM: Unknown
<220> FEATURE:
<223> OTHER INFORMATION: Angiotensin derivative

<400> SEQUENCE: 62

Asp Arg Val Tyr Ile His Pro Phe His Leu Gly Gly Cys Gly Gly
1               5                   10                  15

Gly Gly Gly Asp Arg Val Tyr Ile His Pro Phe His Leu
            20                  25

<210> SEQ ID NO 63
<211> LENGTH: 25
<212> TYPE: PRT
<213> ORGANISM: Unknown
<220> FEATURE:
<223> OTHER INFORMATION: Angiotensin derivative

<400> SEQUENCE: 63

Asp Arg Val Tyr Ile His Pro Phe His Leu Gly Gly Gly Cys Gly Asp
1               5                   10                  15

Arg Val Tyr Ile His Pro Phe His Leu
            20                  25

<210> SEQ ID NO 64
<211> LENGTH: 26
<212> TYPE: PRT
<213> ORGANISM: Unknown
<220> FEATURE:
<223> OTHER INFORMATION: Angiotensin derivative

<400> SEQUENCE: 64

Asp Arg Val Tyr Ile His Pro Phe His Leu Gly Gly Gly Cys Gly Gly
1               5                   10                  15

Asp Arg Val Tyr Ile His Pro Phe His Leu
            20                  25

<210> SEQ ID NO 65
<211> LENGTH: 27
<212> TYPE: PRT
<213> ORGANISM: Unknown
<220> FEATURE:
<223> OTHER INFORMATION: Angiotensin derivative

<400> SEQUENCE: 65

Asp Arg Val Tyr Ile His Pro Phe His Leu Gly Gly Gly Cys Gly Gly
1               5                   10                  15

Gly Asp Arg Val Tyr Ile His Pro Phe His Leu
            20                  25

<210> SEQ ID NO 66
<211> LENGTH: 28
<212> TYPE: PRT
```

```
<213> ORGANISM: Unknown
<220> FEATURE:
<223> OTHER INFORMATION: Angiotensin derivative

<400> SEQUENCE: 66

Asp Arg Val Tyr Ile His Pro Phe His Leu Gly Gly Gly Cys Gly Gly
1               5                   10                  15

Gly Gly Asp Arg Val Tyr Ile His Pro Phe His Leu
            20                  25

<210> SEQ ID NO 67
<211> LENGTH: 29
<212> TYPE: PRT
<213> ORGANISM: Unknown
<220> FEATURE:
<223> OTHER INFORMATION: Angiotensin derivative

<400> SEQUENCE: 67

Asp Arg Val Tyr Ile His Pro Phe His Leu Gly Gly Gly Cys Gly Gly
1               5                   10                  15

Gly Gly Gly Asp Arg Val Tyr Ile His Pro Phe His Leu
            20                  25

<210> SEQ ID NO 68
<211> LENGTH: 30
<212> TYPE: PRT
<213> ORGANISM: Unknown
<220> FEATURE:
<223> OTHER INFORMATION: Angiotensin derivative

<400> SEQUENCE: 68

Asp Arg Val Tyr Ile His Pro Phe His Leu Gly Gly Gly Cys Gly Gly
1               5                   10                  15

Gly Gly Gly Gly Asp Arg Val Tyr Ile His Pro Phe His Leu
            20                  25                  30

<210> SEQ ID NO 69
<211> LENGTH: 26
<212> TYPE: PRT
<213> ORGANISM: Unknown
<220> FEATURE:
<223> OTHER INFORMATION: Angiotensin derivative

<400> SEQUENCE: 69

Asp Arg Val Tyr Ile His Pro Phe His Leu Gly Gly Gly Gly Cys Gly
1               5                   10                  15

Asp Arg Val Tyr Ile His Pro Phe His Leu
            20                  25

<210> SEQ ID NO 70
<211> LENGTH: 27
<212> TYPE: PRT
<213> ORGANISM: Unknown
<220> FEATURE:
<223> OTHER INFORMATION: Angiotensin derivative

<400> SEQUENCE: 70

Asp Arg Val Tyr Ile His Pro Phe His Leu Gly Gly Gly Gly Cys Gly
1               5                   10                  15

Gly Asp Arg Val Tyr Ile His Pro Phe His Leu
            20                  25

<210> SEQ ID NO 71
<211> LENGTH: 28
```

```
<212> TYPE: PRT
<213> ORGANISM: Unknown
<220> FEATURE:
<223> OTHER INFORMATION: Angiotensin derivative

<400> SEQUENCE: 71

Asp Arg Val Tyr Ile His Pro Phe His Leu Gly Gly Gly Gly Cys Gly
1               5                   10                  15

Gly Gly Asp Arg Val Tyr Ile His Pro Phe His Leu
            20                  25

<210> SEQ ID NO 72
<211> LENGTH: 29
<212> TYPE: PRT
<213> ORGANISM: Unknown
<220> FEATURE:
<223> OTHER INFORMATION: Angiotensin derivative

<400> SEQUENCE: 72

Asp Arg Val Tyr Ile His Pro Phe His Leu Gly Gly Gly Gly Cys Gly
1               5                   10                  15

Gly Gly Gly Asp Arg Val Tyr Ile His Pro Phe His Leu
            20                  25

<210> SEQ ID NO 73
<211> LENGTH: 30
<212> TYPE: PRT
<213> ORGANISM: Unknown
<220> FEATURE:
<223> OTHER INFORMATION: Angiotensin derivative

<400> SEQUENCE: 73

Asp Arg Val Tyr Ile His Pro Phe His Leu Gly Gly Gly Gly Cys Gly
1               5                   10                  15

Gly Gly Gly Gly Asp Arg Val Tyr Ile His Pro Phe His Leu
            20                  25                  30

<210> SEQ ID NO 74
<211> LENGTH: 31
<212> TYPE: PRT
<213> ORGANISM: Unknown
<220> FEATURE:
<223> OTHER INFORMATION: Angiotensin derivative

<400> SEQUENCE: 74

Asp Arg Val Tyr Ile His Pro Phe His Leu Gly Gly Gly Gly Cys Gly
1               5                   10                  15

Gly Gly Gly Gly Gly Asp Arg Val Tyr Ile His Pro Phe His Leu
            20                  25                  30

<210> SEQ ID NO 75
<211> LENGTH: 27
<212> TYPE: PRT
<213> ORGANISM: Unknown
<220> FEATURE:
<223> OTHER INFORMATION: Angiotensin derivative

<400> SEQUENCE: 75

Asp Arg Val Tyr Ile His Pro Phe His Leu Gly Gly Gly Gly Gly Cys
1               5                   10                  15

Gly Asp Arg Val Tyr Ile His Pro Phe His Leu
            20                  25

<210> SEQ ID NO 76
```

-continued

<211> LENGTH: 28
<212> TYPE: PRT
<213> ORGANISM: Unknown
<220> FEATURE:
<223> OTHER INFORMATION: Angiotensin derivative

<400> SEQUENCE: 76

Asp Arg Val Tyr Ile His Pro Phe His Leu Gly Gly Gly Gly Gly Cys
1               5                   10                  15
Gly Gly Asp Arg Val Tyr Ile His Pro Phe His Leu
            20                  25

<210> SEQ ID NO 77
<211> LENGTH: 29
<212> TYPE: PRT
<213> ORGANISM: Unknown
<220> FEATURE:
<223> OTHER INFORMATION: Angiotensin derivative

<400> SEQUENCE: 77

Asp Arg Val Tyr Ile His Pro Phe His Leu Gly Gly Gly Gly Gly Cys
1               5                   10                  15
Gly Gly Gly Asp Arg Val Tyr Ile His Pro Phe His Leu
            20                  25

<210> SEQ ID NO 78
<211> LENGTH: 30
<212> TYPE: PRT
<213> ORGANISM: Unknown
<220> FEATURE:
<223> OTHER INFORMATION: Angiotensin derivative

<400> SEQUENCE: 78

Asp Arg Val Tyr Ile His Pro Phe His Leu Gly Gly Gly Gly Gly Cys
1               5                   10                  15
Gly Gly Gly Gly Asp Arg Val Tyr Ile His Pro Phe His Leu
            20                  25                  30

<210> SEQ ID NO 79
<211> LENGTH: 31
<212> TYPE: PRT
<213> ORGANISM: Unknown
<220> FEATURE:
<223> OTHER INFORMATION: Angiotensin derivative

<400> SEQUENCE: 79

Asp Arg Val Tyr Ile His Pro Phe His Leu Gly Gly Gly Gly Gly Cys
1               5                   10                  15
Gly Gly Gly Gly Gly Asp Arg Val Tyr Ile His Pro Phe His Leu
            20                  25                  30

<210> SEQ ID NO 80
<211> LENGTH: 32
<212> TYPE: PRT
<213> ORGANISM: Unknown
<220> FEATURE:
<223> OTHER INFORMATION: Angiotensin derivative

<400> SEQUENCE: 80

Asp Arg Val Tyr Ile His Pro Phe His Leu Gly Gly Gly Gly Gly Cys
1               5                   10                  15
Gly Gly Gly Gly Gly Gly Asp Arg Val Tyr Ile His Pro Phe His Leu
            20                  25                  30

```
<210> SEQ ID NO 81
<211> LENGTH: 28
<212> TYPE: PRT
<213> ORGANISM: Unknown
<220> FEATURE:
<223> OTHER INFORMATION: Angiotensin derivative

<400> SEQUENCE: 81

Asp Arg Val Tyr Ile His Pro Phe His Leu Gly Gly Gly Gly Gly
1               5                   10                  15

Cys Gly Asp Arg Val Tyr Ile His Pro Phe His Leu
            20                  25

<210> SEQ ID NO 82
<211> LENGTH: 29
<212> TYPE: PRT
<213> ORGANISM: Unknown
<220> FEATURE:
<223> OTHER INFORMATION: Angiotensin derivative

<400> SEQUENCE: 82

Asp Arg Val Tyr Ile His Pro Phe His Leu Gly Gly Gly Gly Gly
1               5                   10                  15

Cys Gly Gly Asp Arg Val Tyr Ile His Pro Phe His Leu
            20                  25

<210> SEQ ID NO 83
<211> LENGTH: 30
<212> TYPE: PRT
<213> ORGANISM: Unknown
<220> FEATURE:
<223> OTHER INFORMATION: Angiotensin derivative

<400> SEQUENCE: 83

Asp Arg Val Tyr Ile His Pro Phe His Leu Gly Gly Gly Gly Gly
1               5                   10                  15

Cys Gly Gly Gly Asp Arg Val Tyr Ile His Pro Phe His Leu
            20                  25                  30

<210> SEQ ID NO 84
<211> LENGTH: 31
<212> TYPE: PRT
<213> ORGANISM: Unknown
<220> FEATURE:
<223> OTHER INFORMATION: Angiotensin derivative

<400> SEQUENCE: 84

Asp Arg Val Tyr Ile His Pro Phe His Leu Gly Gly Gly Gly Gly
1               5                   10                  15

Cys Gly Gly Gly Gly Asp Arg Val Tyr Ile His Pro Phe His Leu
            20                  25                  30

<210> SEQ ID NO 85
<211> LENGTH: 32
<212> TYPE: PRT
<213> ORGANISM: Unknown
<220> FEATURE:
<223> OTHER INFORMATION: Angiotensin derivative

<400> SEQUENCE: 85

Asp Arg Val Tyr Ile His Pro Phe His Leu Gly Gly Gly Gly Gly
1               5                   10                  15

Cys Gly Gly Gly Gly Gly Asp Arg Val Tyr Ile His Pro Phe His Leu
            20                  25                  30
```

```
<210> SEQ ID NO 86
<211> LENGTH: 33
<212> TYPE: PRT
<213> ORGANISM: Unknown
<220> FEATURE:
<223> OTHER INFORMATION: Angiotensin derivative

<400> SEQUENCE: 86

Asp Arg Val Tyr Ile His Pro Phe His Leu Gly Gly Gly Gly Gly
1               5                   10                  15

Cys Gly Gly Gly Gly Gly Gly Asp Arg Val Tyr Ile His Pro Phe His
            20                  25                  30

Leu

<210> SEQ ID NO 87
<211> LENGTH: 22
<212> TYPE: PRT
<213> ORGANISM: Unknown
<220> FEATURE:
<223> OTHER INFORMATION: Angiotensin derivative

<400> SEQUENCE: 87

Asp Arg Val Tyr Ile His Pro Phe His Leu Gly Gly Cys Gly Asp Arg
1               5                   10                  15

Val Tyr Ile His Pro Phe
            20

<210> SEQ ID NO 88
<211> LENGTH: 23
<212> TYPE: PRT
<213> ORGANISM: Unknown
<220> FEATURE:
<223> OTHER INFORMATION: Angiotensin derivative

<400> SEQUENCE: 88

Asp Arg Val Tyr Ile His Pro Phe His Leu Gly Gly Gly Cys Gly Asp
1               5                   10                  15

Arg Val Tyr Ile His Pro Phe
            20

<210> SEQ ID NO 89
<211> LENGTH: 24
<212> TYPE: PRT
<213> ORGANISM: Unknown
<220> FEATURE:
<223> OTHER INFORMATION: Angiotensin derivative

<400> SEQUENCE: 89

Asp Arg Val Tyr Ile His Pro Phe His Leu Gly Gly Gly Gly Cys Gly
1               5                   10                  15

Asp Arg Val Tyr Ile His Pro Phe
            20

<210> SEQ ID NO 90
<211> LENGTH: 25
<212> TYPE: PRT
<213> ORGANISM: Unknown
<220> FEATURE:
<223> OTHER INFORMATION: Angiotensin derivative

<400> SEQUENCE: 90

Asp Arg Val Tyr Ile His Pro Phe His Leu Gly Gly Gly Gly Gly Cys
1               5                   10                  15
```

-continued

Gly Asp Arg Val Tyr Ile His Pro Phe
            20                  25

<210> SEQ ID NO 91
<211> LENGTH: 26
<212> TYPE: PRT
<213> ORGANISM: Unknown
<220> FEATURE:
<223> OTHER INFORMATION: Angiotensin derivative

<400> SEQUENCE: 91

Asp Arg Val Tyr Ile His Pro Phe His Leu Gly Gly Gly Gly Gly Gly
1               5                   10                  15

Cys Gly Asp Arg Val Tyr Ile His Pro Phe
            20                  25

<210> SEQ ID NO 92
<211> LENGTH: 22
<212> TYPE: PRT
<213> ORGANISM: Unknown
<220> FEATURE:
<223> OTHER INFORMATION: Angiotensin derivative

<400> SEQUENCE: 92

Asp Arg Val Tyr Ile His Pro Phe His Leu Gly Cys Gly Gly Asp Arg
1               5                   10                  15

Val Tyr Ile His Pro Phe
            20

<210> SEQ ID NO 93
<211> LENGTH: 23
<212> TYPE: PRT
<213> ORGANISM: Unknown
<220> FEATURE:
<223> OTHER INFORMATION: Angiotensin derivative

<400> SEQUENCE: 93

Asp Arg Val Tyr Ile His Pro Phe His Leu Gly Gly Cys Gly Gly Asp
1               5                   10                  15

Arg Val Tyr Ile His Pro Phe
            20

<210> SEQ ID NO 94
<211> LENGTH: 24
<212> TYPE: PRT
<213> ORGANISM: Unknown
<220> FEATURE:
<223> OTHER INFORMATION: Angiotensin derivative

<400> SEQUENCE: 94

Asp Arg Val Tyr Ile His Pro Phe His Leu Gly Gly Gly Cys Gly Gly
1               5                   10                  15

Asp Arg Val Tyr Ile His Pro Phe
            20

<210> SEQ ID NO 95
<211> LENGTH: 25
<212> TYPE: PRT
<213> ORGANISM: Unknown
<220> FEATURE:
<223> OTHER INFORMATION: Angiotensin derivative

<400> SEQUENCE: 95

Asp Arg Val Tyr Ile His Pro Phe His Leu Gly Gly Gly Gly Cys Gly
1               5                   10                  15

Gly Asp Arg Val Tyr Ile His Pro Phe
            20                  25

<210> SEQ ID NO 96
<211> LENGTH: 26
<212> TYPE: PRT
<213> ORGANISM: Unknown
<220> FEATURE:
<223> OTHER INFORMATION: Angiotensin derivative

<400> SEQUENCE: 96

Asp Arg Val Tyr Ile His Pro Phe His Leu Gly Gly Gly Gly Gly Cys
1               5                   10                  15

Gly Gly Asp Arg Val Tyr Ile His Pro Phe
            20                  25

<210> SEQ ID NO 97
<211> LENGTH: 27
<212> TYPE: PRT
<213> ORGANISM: Unknown
<220> FEATURE:
<223> OTHER INFORMATION: Angiotensin derivative

<400> SEQUENCE: 97

Asp Arg Val Tyr Ile His Pro Phe His Leu Gly Gly Gly Gly Gly Gly
1               5                   10                  15

Cys Gly Gly Asp Arg Val Tyr Ile His Pro Phe
            20                  25

<210> SEQ ID NO 98
<211> LENGTH: 23
<212> TYPE: PRT
<213> ORGANISM: Unknown
<220> FEATURE:
<223> OTHER INFORMATION: Angiotensin derivative

<400> SEQUENCE: 98

Asp Arg Val Tyr Ile His Pro Phe His Leu Gly Cys Gly Gly Gly Asp
1               5                   10                  15

Arg Val Tyr Ile His Pro Phe
            20

<210> SEQ ID NO 99
<211> LENGTH: 24
<212> TYPE: PRT
<213> ORGANISM: Unknown
<220> FEATURE:
<223> OTHER INFORMATION: Angiotensin derivative

<400> SEQUENCE: 99

Asp Arg Val Tyr Ile His Pro Phe His Leu Gly Gly Cys Gly Gly Gly
1               5                   10                  15

Asp Arg Val Tyr Ile His Pro Phe
            20

<210> SEQ ID NO 100
<211> LENGTH: 25
<212> TYPE: PRT
<213> ORGANISM: Unknown
<220> FEATURE:
<223> OTHER INFORMATION: Angiotensin derivative

<400> SEQUENCE: 100

Asp Arg Val Tyr Ile His Pro Phe His Leu Gly Gly Gly Cys Gly Gly

Gly Asp Arg Val Tyr Ile His Pro Phe
            20                  25

<210> SEQ ID NO 101
<211> LENGTH: 26
<212> TYPE: PRT
<213> ORGANISM: Unknown
<220> FEATURE:
<223> OTHER INFORMATION: Angiotensin derivative

<400> SEQUENCE: 101

Asp Arg Val Tyr Ile His Pro Phe His Leu Gly Gly Gly Gly Cys Gly
1               5                   10                  15

Gly Gly Asp Arg Val Tyr Ile His Pro Phe
            20                  25

<210> SEQ ID NO 102
<211> LENGTH: 27
<212> TYPE: PRT
<213> ORGANISM: Unknown
<220> FEATURE:
<223> OTHER INFORMATION: Angiotensin derivative

<400> SEQUENCE: 102

Asp Arg Val Tyr Ile His Pro Phe His Leu Gly Gly Gly Gly Gly Cys
1               5                   10                  15

Gly Gly Gly Asp Arg Val Tyr Ile His Pro Phe
            20                  25

<210> SEQ ID NO 103
<211> LENGTH: 28
<212> TYPE: PRT
<213> ORGANISM: Unknown
<220> FEATURE:
<223> OTHER INFORMATION: Angiotensin derivative

<400> SEQUENCE: 103

Asp Arg Val Tyr Ile His Pro Phe His Leu Gly Gly Gly Gly Gly Gly
1               5                   10                  15

Cys Gly Gly Gly Asp Arg Val Tyr Ile His Pro Phe
            20                  25

<210> SEQ ID NO 104
<211> LENGTH: 24
<212> TYPE: PRT
<213> ORGANISM: Unknown
<220> FEATURE:
<223> OTHER INFORMATION: Angiotensin derivative

<400> SEQUENCE: 104

Asp Arg Val Tyr Ile His Pro Phe His Leu Gly Cys Gly Gly Gly Gly
1               5                   10                  15

Asp Arg Val Tyr Ile His Pro Phe
            20

<210> SEQ ID NO 105
<211> LENGTH: 25
<212> TYPE: PRT
<213> ORGANISM: Unknown
<220> FEATURE:
<223> OTHER INFORMATION: Angiotensin derivative

<400> SEQUENCE: 105

```
Asp Arg Val Tyr Ile His Pro Phe His Leu Gly Gly Cys Gly Gly
1               5                   10                  15

Gly Asp Arg Val Tyr Ile His Pro Phe
            20                  25

<210> SEQ ID NO 106
<211> LENGTH: 26
<212> TYPE: PRT
<213> ORGANISM: Unknown
<220> FEATURE:
<223> OTHER INFORMATION: Angiotensin derivative

<400> SEQUENCE: 106

Asp Arg Val Tyr Ile His Pro Phe His Leu Gly Gly Gly Cys Gly
1               5                   10                  15

Gly Gly Asp Arg Val Tyr Ile His Pro Phe
            20                  25

<210> SEQ ID NO 107
<211> LENGTH: 27
<212> TYPE: PRT
<213> ORGANISM: Unknown
<220> FEATURE:
<223> OTHER INFORMATION: Angiotensin derivative

<400> SEQUENCE: 107

Asp Arg Val Tyr Ile His Pro Phe His Leu Gly Gly Gly Gly Cys Gly
1               5                   10                  15

Gly Gly Gly Asp Arg Val Tyr Ile His Pro Phe
            20                  25

<210> SEQ ID NO 108
<211> LENGTH: 28
<212> TYPE: PRT
<213> ORGANISM: Unknown
<220> FEATURE:
<223> OTHER INFORMATION: Angiotensin derivative

<400> SEQUENCE: 108

Asp Arg Val Tyr Ile His Pro Phe His Leu Gly Gly Gly Gly Gly Cys
1               5                   10                  15

Gly Gly Gly Gly Asp Arg Val Tyr Ile His Pro Phe
            20                  25

<210> SEQ ID NO 109
<211> LENGTH: 29
<212> TYPE: PRT
<213> ORGANISM: Unknown
<220> FEATURE:
<223> OTHER INFORMATION: Angiotensin derivative

<400> SEQUENCE: 109

Asp Arg Val Tyr Ile His Pro Phe His Leu Gly Gly Gly Gly Gly Gly
1               5                   10                  15

Cys Gly Gly Gly Gly Asp Arg Val Tyr Ile His Pro Phe
            20                  25

<210> SEQ ID NO 110
<211> LENGTH: 25
<212> TYPE: PRT
<213> ORGANISM: Unknown
<220> FEATURE:
<223> OTHER INFORMATION: Angiotensin derivative

<400> SEQUENCE: 110
```

Asp Arg Val Tyr Ile His Pro Phe His Leu Gly Cys Gly Gly Gly
1               5                   10                  15

Gly Asp Arg Val Tyr Ile His Pro Phe
            20                  25

<210> SEQ ID NO 111
<211> LENGTH: 26
<212> TYPE: PRT
<213> ORGANISM: Unknown
<220> FEATURE:
<223> OTHER INFORMATION: Angiotensin derivative

<400> SEQUENCE: 111

Asp Arg Val Tyr Ile His Pro Phe His Leu Gly Gly Cys Gly Gly
1               5                   10                  15

Gly Gly Asp Arg Val Tyr Ile His Pro Phe
            20                  25

<210> SEQ ID NO 112
<211> LENGTH: 27
<212> TYPE: PRT
<213> ORGANISM: Unknown
<220> FEATURE:
<223> OTHER INFORMATION: Angiotensin derivative

<400> SEQUENCE: 112

Asp Arg Val Tyr Ile His Pro Phe His Leu Gly Gly Gly Cys Gly
1               5                   10                  15

Gly Gly Gly Asp Arg Val Tyr Ile His Pro Phe
            20                  25

<210> SEQ ID NO 113
<211> LENGTH: 28
<212> TYPE: PRT
<213> ORGANISM: Unknown
<220> FEATURE:
<223> OTHER INFORMATION: Angiotensin derivative

<400> SEQUENCE: 113

Asp Arg Val Tyr Ile His Pro Phe His Leu Gly Gly Gly Gly Cys Gly
1               5                   10                  15

Gly Gly Gly Gly Asp Arg Val Tyr Ile His Pro Phe
            20                  25

<210> SEQ ID NO 114
<211> LENGTH: 29
<212> TYPE: PRT
<213> ORGANISM: Unknown
<220> FEATURE:
<223> OTHER INFORMATION: Angiotensin derivative

<400> SEQUENCE: 114

Asp Arg Val Tyr Ile His Pro Phe His Leu Gly Gly Gly Gly Gly Cys
1               5                   10                  15

Gly Gly Gly Gly Gly Asp Arg Val Tyr Ile His Pro Phe
            20                  25

<210> SEQ ID NO 115
<211> LENGTH: 30
<212> TYPE: PRT
<213> ORGANISM: Unknown
<220> FEATURE:
<223> OTHER INFORMATION: Angiotensin derivative

```
<400> SEQUENCE: 115

Asp Arg Val Tyr Ile His Pro Phe His Leu Gly Gly Gly Gly Gly
1               5                   10                  15

Cys Gly Gly Gly Gly Gly Asp Arg Val Tyr Ile His Pro Phe
            20                  25                  30

<210> SEQ ID NO 116
<211> LENGTH: 26
<212> TYPE: PRT
<213> ORGANISM: Unknown
<220> FEATURE:
<223> OTHER INFORMATION: Angiotensin derivative

<400> SEQUENCE: 116

Asp Arg Val Tyr Ile His Pro Phe His Leu Gly Cys Gly Gly Gly
1               5                   10                  15

Gly Gly Asp Arg Val Tyr Ile His Pro Phe
            20                  25

<210> SEQ ID NO 117
<211> LENGTH: 27
<212> TYPE: PRT
<213> ORGANISM: Unknown
<220> FEATURE:
<223> OTHER INFORMATION: Angiotensin derivative

<400> SEQUENCE: 117

Asp Arg Val Tyr Ile His Pro Phe His Leu Gly Gly Cys Gly Gly
1               5                   10                  15

Gly Gly Gly Asp Arg Val Tyr Ile His Pro Phe
            20                  25

<210> SEQ ID NO 118
<211> LENGTH: 28
<212> TYPE: PRT
<213> ORGANISM: Unknown
<220> FEATURE:
<223> OTHER INFORMATION: Angiotensin derivative

<400> SEQUENCE: 118

Asp Arg Val Tyr Ile His Pro Phe His Leu Gly Gly Gly Cys Gly
1               5                   10                  15

Gly Gly Gly Gly Asp Arg Val Tyr Ile His Pro Phe
            20                  25

<210> SEQ ID NO 119
<211> LENGTH: 29
<212> TYPE: PRT
<213> ORGANISM: Unknown
<220> FEATURE:
<223> OTHER INFORMATION: Angiotensin derivative

<400> SEQUENCE: 119

Asp Arg Val Tyr Ile His Pro Phe His Leu Gly Gly Gly Gly Cys Gly
1               5                   10                  15

Gly Gly Gly Gly Gly Asp Arg Val Tyr Ile His Pro Phe
            20                  25

<210> SEQ ID NO 120
<211> LENGTH: 30
<212> TYPE: PRT
<213> ORGANISM: Unknown
<220> FEATURE:
<223> OTHER INFORMATION: Angiotensin derivative
```

-continued

```
<400> SEQUENCE: 120

Asp Arg Val Tyr Ile His Pro Phe His Leu Gly Gly Gly Gly Gly Cys
1               5                   10                  15

Gly Gly Gly Gly Gly Gly Asp Arg Val Tyr Ile His Pro Phe
            20                  25                  30

<210> SEQ ID NO 121
<211> LENGTH: 31
<212> TYPE: PRT
<213> ORGANISM: Unknown
<220> FEATURE:
<223> OTHER INFORMATION: Angiotensin derivative

<400> SEQUENCE: 121

Asp Arg Val Tyr Ile His Pro Phe His Leu Gly Gly Gly Gly Gly Gly
1               5                   10                  15

Cys Gly Gly Gly Gly Gly Asp Arg Val Tyr Ile His Pro Phe
            20                  25                  30

<210> SEQ ID NO 122
<211> LENGTH: 24
<212> TYPE: PRT
<213> ORGANISM: Unknown
<220> FEATURE:
<223> OTHER INFORMATION: Angiotensin derivative

<400> SEQUENCE: 122

Leu His Phe Pro His Ile Tyr Val Arg Asp Gly Gly Cys Gly Asp Arg
1               5                   10                  15

Val Tyr Ile His Pro Phe His Leu
            20

<210> SEQ ID NO 123
<211> LENGTH: 25
<212> TYPE: PRT
<213> ORGANISM: Unknown
<220> FEATURE:
<223> OTHER INFORMATION: Angiotensin derivative

<400> SEQUENCE: 123

Leu His Phe Pro His Ile Tyr Val Arg Asp Gly Gly Gly Cys Gly Asp
1               5                   10                  15

Arg Val Tyr Ile His Pro Phe His Leu
            20                  25

<210> SEQ ID NO 124
<211> LENGTH: 26
<212> TYPE: PRT
<213> ORGANISM: Unknown
<220> FEATURE:
<223> OTHER INFORMATION: Angiotensin derivative

<400> SEQUENCE: 124

Leu His Phe Pro His Ile Tyr Val Arg Asp Gly Gly Gly Gly Cys Gly
1               5                   10                  15

Asp Arg Val Tyr Ile His Pro Phe His Leu
            20                  25

<210> SEQ ID NO 125
<211> LENGTH: 27
<212> TYPE: PRT
<213> ORGANISM: Unknown
<220> FEATURE:
```

-continued

```
<223> OTHER INFORMATION: Angiotensin derivative

<400> SEQUENCE: 125

Leu His Phe Pro His Ile Tyr Val Arg Asp Gly Gly Gly Gly Cys
1               5                  10                  15

Gly Asp Arg Val Tyr Ile His Pro Phe His Leu
            20                  25

<210> SEQ ID NO 126
<211> LENGTH: 28
<212> TYPE: PRT
<213> ORGANISM: Unknown
<220> FEATURE:
<223> OTHER INFORMATION: Angiotensin derivative

<400> SEQUENCE: 126

Leu His Phe Pro His Ile Tyr Val Arg Asp Gly Gly Gly Gly Gly
1               5                  10                  15

Cys Gly Asp Arg Val Tyr Ile His Pro Phe His Leu
            20                  25

<210> SEQ ID NO 127
<211> LENGTH: 24
<212> TYPE: PRT
<213> ORGANISM: Unknown
<220> FEATURE:
<223> OTHER INFORMATION: Angiotensin derivative

<400> SEQUENCE: 127

Leu His Phe Pro His Ile Tyr Val Arg Asp Gly Cys Gly Gly Asp Arg
1               5                  10                  15

Val Tyr Ile His Pro Phe His Leu
            20

<210> SEQ ID NO 128
<211> LENGTH: 25
<212> TYPE: PRT
<213> ORGANISM: Unknown
<220> FEATURE:
<223> OTHER INFORMATION: Angiotensin derivative

<400> SEQUENCE: 128

Leu His Phe Pro His Ile Tyr Val Arg Asp Gly Gly Cys Gly Gly Asp
1               5                  10                  15

Arg Val Tyr Ile His Pro Phe His Leu
            20                  25

<210> SEQ ID NO 129
<211> LENGTH: 26
<212> TYPE: PRT
<213> ORGANISM: Unknown
<220> FEATURE:
<223> OTHER INFORMATION: Angiotensin derivative

<400> SEQUENCE: 129

Leu His Phe Pro His Ile Tyr Val Arg Asp Gly Gly Gly Cys Gly Gly
1               5                  10                  15

Asp Arg Val Tyr Ile His Pro Phe His Leu
            20                  25

<210> SEQ ID NO 130
<211> LENGTH: 27
<212> TYPE: PRT
<213> ORGANISM: Unknown
```

```
<220> FEATURE:
<223> OTHER INFORMATION: Angiotensin derivative

<400> SEQUENCE: 130

Leu His Phe Pro His Ile Tyr Val Arg Asp Gly Gly Gly Gly Cys Gly
1               5                   10                  15

Gly Asp Arg Val Tyr Ile His Pro Phe His Leu
            20                  25

<210> SEQ ID NO 131
<211> LENGTH: 28
<212> TYPE: PRT
<213> ORGANISM: Unknown
<220> FEATURE:
<223> OTHER INFORMATION: Angiotensin derivative

<400> SEQUENCE: 131

Leu His Phe Pro His Ile Tyr Val Arg Asp Gly Gly Gly Gly Gly Cys
1               5                   10                  15

Gly Gly Asp Arg Val Tyr Ile His Pro Phe His Leu
            20                  25

<210> SEQ ID NO 132
<211> LENGTH: 29
<212> TYPE: PRT
<213> ORGANISM: Unknown
<220> FEATURE:
<223> OTHER INFORMATION: Angiotensin derivative

<400> SEQUENCE: 132

Leu His Phe Pro His Ile Tyr Val Arg Asp Gly Gly Gly Gly Gly Gly
1               5                   10                  15

Cys Gly Gly Asp Arg Val Tyr Ile His Pro Phe His Leu
            20                  25

<210> SEQ ID NO 133
<211> LENGTH: 25
<212> TYPE: PRT
<213> ORGANISM: Unknown
<220> FEATURE:
<223> OTHER INFORMATION: Angiotensin derivative

<400> SEQUENCE: 133

Leu His Phe Pro His Ile Tyr Val Arg Asp Gly Cys Gly Gly Gly Asp
1               5                   10                  15

Arg Val Tyr Ile His Pro Phe His Leu
            20                  25

<210> SEQ ID NO 134
<211> LENGTH: 26
<212> TYPE: PRT
<213> ORGANISM: Unknown
<220> FEATURE:
<223> OTHER INFORMATION: Angiotensin derivative

<400> SEQUENCE: 134

Leu His Phe Pro His Ile Tyr Val Arg Asp Gly Gly Cys Gly Gly Gly
1               5                   10                  15

Asp Arg Val Tyr Ile His Pro Phe His Leu
            20                  25

<210> SEQ ID NO 135
<211> LENGTH: 27
<212> TYPE: PRT
```

```
<213> ORGANISM: Unknown
<220> FEATURE:
<223> OTHER INFORMATION: Angiotensin derivative

<400> SEQUENCE: 135

Leu His Phe Pro His Ile Tyr Val Arg Asp Gly Gly Gly Cys Gly Gly
1               5                   10                  15

Gly Asp Arg Val Tyr Ile His Pro Phe His Leu
            20                  25

<210> SEQ ID NO 136
<211> LENGTH: 28
<212> TYPE: PRT
<213> ORGANISM: Unknown
<220> FEATURE:
<223> OTHER INFORMATION: Angiotensin derivative

<400> SEQUENCE: 136

Leu His Phe Pro His Ile Tyr Val Arg Asp Gly Gly Gly Gly Cys Gly
1               5                   10                  15

Gly Gly Asp Arg Val Tyr Ile His Pro Phe His Leu
            20                  25

<210> SEQ ID NO 137
<211> LENGTH: 29
<212> TYPE: PRT
<213> ORGANISM: Unknown
<220> FEATURE:
<223> OTHER INFORMATION: Angiotensin derivative

<400> SEQUENCE: 137

Leu His Phe Pro His Ile Tyr Val Arg Asp Gly Gly Gly Gly Gly Cys
1               5                   10                  15

Gly Gly Gly Asp Arg Val Tyr Ile His Pro Phe His Leu
            20                  25

<210> SEQ ID NO 138
<211> LENGTH: 30
<212> TYPE: PRT
<213> ORGANISM: Unknown
<220> FEATURE:
<223> OTHER INFORMATION: Angiotensin derivative

<400> SEQUENCE: 138

Leu His Phe Pro His Ile Tyr Val Arg Asp Gly Gly Gly Gly Gly Gly
1               5                   10                  15

Cys Gly Gly Gly Asp Arg Val Tyr Ile His Pro Phe His Leu
            20                  25                  30

<210> SEQ ID NO 139
<211> LENGTH: 26
<212> TYPE: PRT
<213> ORGANISM: Unknown
<220> FEATURE:
<223> OTHER INFORMATION: Angiotensin derivative

<400> SEQUENCE: 139

Leu His Phe Pro His Ile Tyr Val Arg Asp Gly Cys Gly Gly Gly
1               5                   10                  15

Asp Arg Val Tyr Ile His Pro Phe His Leu
            20                  25

<210> SEQ ID NO 140
<211> LENGTH: 27
```

```
<212> TYPE: PRT
<213> ORGANISM: Unknown
<220> FEATURE:
<223> OTHER INFORMATION: Angiotensin derivative

<400> SEQUENCE: 140

Leu His Phe Pro His Ile Tyr Val Arg Asp Gly Gly Cys Gly Gly
1               5                   10                  15

Gly Asp Arg Val Tyr Ile His Pro Phe His Leu
            20                  25

<210> SEQ ID NO 141
<211> LENGTH: 28
<212> TYPE: PRT
<213> ORGANISM: Unknown
<220> FEATURE:
<223> OTHER INFORMATION: Angiotensin derivative

<400> SEQUENCE: 141

Leu His Phe Pro His Ile Tyr Val Arg Asp Gly Gly Gly Cys Gly
1               5                   10                  15

Gly Gly Asp Arg Val Tyr Ile His Pro Phe His Leu
            20                  25

<210> SEQ ID NO 142
<211> LENGTH: 29
<212> TYPE: PRT
<213> ORGANISM: Unknown
<220> FEATURE:
<223> OTHER INFORMATION: Angiotensin derivative

<400> SEQUENCE: 142

Leu His Phe Pro His Ile Tyr Val Arg Asp Gly Gly Gly Gly Cys
1               5                   10                  15

Gly Gly Gly Asp Arg Val Tyr Ile His Pro Phe His Leu
            20                  25

<210> SEQ ID NO 143
<211> LENGTH: 30
<212> TYPE: PRT
<213> ORGANISM: Unknown
<220> FEATURE:
<223> OTHER INFORMATION: Angiotensin derivative

<400> SEQUENCE: 143

Leu His Phe Pro His Ile Tyr Val Arg Asp Gly Gly Gly Gly Cys
1               5                   10                  15

Gly Gly Gly Gly Asp Arg Val Tyr Ile His Pro Phe His Leu
            20                  25                  30

<210> SEQ ID NO 144
<211> LENGTH: 31
<212> TYPE: PRT
<213> ORGANISM: Unknown
<220> FEATURE:
<223> OTHER INFORMATION: Angiotensin derivative

<400> SEQUENCE: 144

Leu His Phe Pro His Ile Tyr Val Arg Asp Gly Gly Gly Gly Gly
1               5                   10                  15

Cys Gly Gly Gly Gly Asp Arg Val Tyr Ile His Pro Phe His Leu
            20                  25                  30

<210> SEQ ID NO 145
```

```
<211> LENGTH: 27
<212> TYPE: PRT
<213> ORGANISM: Unknown
<220> FEATURE:
<223> OTHER INFORMATION: Angiotensin derivative

<400> SEQUENCE: 145

Leu His Phe Pro His Ile Tyr Val Arg Asp Gly Cys Gly Gly Gly
1               5                   10                  15

Gly Asp Arg Val Tyr Ile His Pro Phe His Leu
            20                  25

<210> SEQ ID NO 146
<211> LENGTH: 28
<212> TYPE: PRT
<213> ORGANISM: Unknown
<220> FEATURE:
<223> OTHER INFORMATION: Angiotensin derivative

<400> SEQUENCE: 146

Leu His Phe Pro His Ile Tyr Val Arg Asp Gly Gly Cys Gly Gly
1               5                   10                  15

Gly Gly Asp Arg Val Tyr Ile His Pro Phe His Leu
            20                  25

<210> SEQ ID NO 147
<211> LENGTH: 29
<212> TYPE: PRT
<213> ORGANISM: Unknown
<220> FEATURE:
<223> OTHER INFORMATION: Angiotensin derivative

<400> SEQUENCE: 147

Leu His Phe Pro His Ile Tyr Val Arg Asp Gly Gly Cys Gly Gly
1               5                   10                  15

Gly Gly Gly Asp Arg Val Tyr Ile His Pro Phe His Leu
            20                  25

<210> SEQ ID NO 148
<211> LENGTH: 30
<212> TYPE: PRT
<213> ORGANISM: Unknown
<220> FEATURE:
<223> OTHER INFORMATION: Angiotensin derivative

<400> SEQUENCE: 148

Leu His Phe Pro His Ile Tyr Val Arg Asp Gly Gly Gly Cys Gly
1               5                   10                  15

Gly Gly Gly Gly Asp Arg Val Tyr Ile His Pro Phe His Leu
            20                  25                  30

<210> SEQ ID NO 149
<211> LENGTH: 31
<212> TYPE: PRT
<213> ORGANISM: Unknown
<220> FEATURE:
<223> OTHER INFORMATION: Angiotensin derivative

<400> SEQUENCE: 149

Leu His Phe Pro His Ile Tyr Val Arg Asp Gly Gly Gly Gly Cys
1               5                   10                  15

Gly Gly Gly Gly Gly Asp Arg Val Tyr Ile His Pro Phe His Leu
            20                  25                  30
```

```
<210> SEQ ID NO 150
<211> LENGTH: 32
<212> TYPE: PRT
<213> ORGANISM: Unknown
<220> FEATURE:
<223> OTHER INFORMATION: Angiotensin derivative

<400> SEQUENCE: 150

Leu His Phe Pro His Ile Tyr Val Arg Asp Gly Gly Gly Gly Gly
1               5                   10                  15

Cys Gly Gly Gly Gly Gly Asp Arg Val Tyr Ile His Pro Phe His Leu
                20                  25                  30

<210> SEQ ID NO 151
<211> LENGTH: 28
<212> TYPE: PRT
<213> ORGANISM: Unknown
<220> FEATURE:
<223> OTHER INFORMATION: Angiotensin derivative

<400> SEQUENCE: 151

Leu His Phe Pro His Ile Tyr Val Arg Asp Gly Cys Gly Gly Gly
1               5                   10                  15

Gly Gly Asp Arg Val Tyr Ile His Pro Phe His Leu
                20                  25

<210> SEQ ID NO 152
<211> LENGTH: 29
<212> TYPE: PRT
<213> ORGANISM: Unknown
<220> FEATURE:
<223> OTHER INFORMATION: Angiotensin derivative

<400> SEQUENCE: 152

Leu His Phe Pro His Ile Tyr Val Arg Asp Gly Gly Cys Gly Gly
1               5                   10                  15

Gly Gly Gly Asp Arg Val Tyr Ile His Pro Phe His Leu
                20                  25

<210> SEQ ID NO 153
<211> LENGTH: 30
<212> TYPE: PRT
<213> ORGANISM: Unknown
<220> FEATURE:
<223> OTHER INFORMATION: Angiotensin derivative

<400> SEQUENCE: 153

Leu His Phe Pro His Ile Tyr Val Arg Asp Gly Gly Gly Cys Gly
1               5                   10                  15

Gly Gly Gly Gly Asp Arg Val Tyr Ile His Pro Phe His Leu
                20                  25                  30

<210> SEQ ID NO 154
<211> LENGTH: 31
<212> TYPE: PRT
<213> ORGANISM: Unknown
<220> FEATURE:
<223> OTHER INFORMATION: Angiotensin derivative

<400> SEQUENCE: 154

Leu His Phe Pro His Ile Tyr Val Arg Asp Gly Gly Gly Gly Cys Gly
1               5                   10                  15

Gly Gly Gly Gly Gly Asp Arg Val Tyr Ile His Pro Phe His Leu
                20                  25                  30
```

```
<210> SEQ ID NO 155
<211> LENGTH: 32
<212> TYPE: PRT
<213> ORGANISM: Unknown
<220> FEATURE:
<223> OTHER INFORMATION: Angiotensin derivative

<400> SEQUENCE: 155

Leu His Phe Pro His Ile Tyr Val Arg Asp Gly Gly Gly Gly Cys
1               5                   10                  15

Gly Gly Gly Gly Gly Gly Asp Arg Val Tyr Ile His Pro Phe His Leu
            20                  25                  30

<210> SEQ ID NO 156
<211> LENGTH: 33
<212> TYPE: PRT
<213> ORGANISM: Unknown
<220> FEATURE:
<223> OTHER INFORMATION: Angiotensin derivative

<400> SEQUENCE: 156

Leu His Phe Pro His Ile Tyr Val Arg Asp Gly Gly Gly Gly Gly
1               5                   10                  15

Cys Gly Gly Gly Gly Gly Gly Asp Arg Val Tyr Ile His Pro Phe His
            20                  25                  30

Leu

<210> SEQ ID NO 157
<211> LENGTH: 22
<212> TYPE: PRT
<213> ORGANISM: Unknown
<220> FEATURE:
<223> OTHER INFORMATION: Angiotensin derivative

<400> SEQUENCE: 157

Leu His Phe Pro His Ile Tyr Val Arg Asp Gly Gly Cys Gly Asp Arg
1               5                   10                  15

Val Tyr Ile His Pro Phe
            20

<210> SEQ ID NO 158
<211> LENGTH: 23
<212> TYPE: PRT
<213> ORGANISM: Unknown
<220> FEATURE:
<223> OTHER INFORMATION: Angiotensin derivative

<400> SEQUENCE: 158

Leu His Phe Pro His Ile Tyr Val Arg Asp Gly Gly Gly Cys Gly Asp
1               5                   10                  15

Arg Val Tyr Ile His Pro Phe
            20

<210> SEQ ID NO 159
<211> LENGTH: 24
<212> TYPE: PRT
<213> ORGANISM: Unknown
<220> FEATURE:
<223> OTHER INFORMATION: Angiotensin derivative

<400> SEQUENCE: 159

Leu His Phe Pro His Ile Tyr Val Arg Asp Gly Gly Gly Gly Cys Gly
1               5                   10                  15
```

-continued

Asp Arg Val Tyr Ile His Pro Phe
            20

<210> SEQ ID NO 160
<211> LENGTH: 25
<212> TYPE: PRT
<213> ORGANISM: Unknown
<220> FEATURE:
<223> OTHER INFORMATION: Angiotensin derivative

<400> SEQUENCE: 160

Leu His Phe Pro His Ile Tyr Val Arg Asp Gly Gly Gly Gly Gly Cys
1               5                   10                  15

Gly Asp Arg Val Tyr Ile His Pro Phe
            20                  25

<210> SEQ ID NO 161
<211> LENGTH: 26
<212> TYPE: PRT
<213> ORGANISM: Unknown
<220> FEATURE:
<223> OTHER INFORMATION: Angiotensin derivative

<400> SEQUENCE: 161

Leu His Phe Pro His Ile Tyr Val Arg Asp Gly Gly Gly Gly Gly Gly
1               5                   10                  15

Cys Gly Asp Arg Val Tyr Ile His Pro Phe
            20                  25

<210> SEQ ID NO 162
<211> LENGTH: 22
<212> TYPE: PRT
<213> ORGANISM: Unknown
<220> FEATURE:
<223> OTHER INFORMATION: Angiotensin derivative

<400> SEQUENCE: 162

Leu His Phe Pro His Ile Tyr Val Arg Asp Gly Cys Gly Gly Asp Arg
1               5                   10                  15

Val Tyr Ile His Pro Phe
            20

<210> SEQ ID NO 163
<211> LENGTH: 23
<212> TYPE: PRT
<213> ORGANISM: Unknown
<220> FEATURE:
<223> OTHER INFORMATION: Angiotensin derivative

<400> SEQUENCE: 163

Leu His Phe Pro His Ile Tyr Val Arg Asp Gly Gly Cys Gly Gly Asp
1               5                   10                  15

Arg Val Tyr Ile His Pro Phe
            20

<210> SEQ ID NO 164
<211> LENGTH: 24
<212> TYPE: PRT
<213> ORGANISM: Unknown
<220> FEATURE:
<223> OTHER INFORMATION: Angiotensin derivative

<400> SEQUENCE: 164

Leu His Phe Pro His Ile Tyr Val Arg Asp Gly Gly Gly Cys Gly Gly
1               5                   10                  15

Asp Arg Val Tyr Ile His Pro Phe
            20

<210> SEQ ID NO 165
<211> LENGTH: 25
<212> TYPE: PRT
<213> ORGANISM: Unknown
<220> FEATURE:
<223> OTHER INFORMATION: Angiotensin derivative

<400> SEQUENCE: 165

Leu His Phe Pro His Ile Tyr Val Arg Asp Gly Gly Gly Gly Cys Gly
1               5                   10                  15

Gly Asp Arg Val Tyr Ile His Pro Phe
            20                  25

<210> SEQ ID NO 166
<211> LENGTH: 26
<212> TYPE: PRT
<213> ORGANISM: Unknown
<220> FEATURE:
<223> OTHER INFORMATION: Angiotensin derivative

<400> SEQUENCE: 166

Leu His Phe Pro His Ile Tyr Val Arg Asp Gly Gly Gly Gly Gly Cys
1               5                   10                  15

Gly Gly Asp Arg Val Tyr Ile His Pro Phe
            20                  25

<210> SEQ ID NO 167
<211> LENGTH: 27
<212> TYPE: PRT
<213> ORGANISM: Unknown
<220> FEATURE:
<223> OTHER INFORMATION: Angiotensin derivative

<400> SEQUENCE: 167

Leu His Phe Pro His Ile Tyr Val Arg Asp Gly Gly Gly Gly Gly Gly
1               5                   10                  15

Cys Gly Gly Asp Arg Val Tyr Ile His Pro Phe
            20                  25

<210> SEQ ID NO 168
<211> LENGTH: 23
<212> TYPE: PRT
<213> ORGANISM: Unknown
<220> FEATURE:
<223> OTHER INFORMATION: Angiotensin derivative

<400> SEQUENCE: 168

Leu His Phe Pro His Ile Tyr Val Arg Asp Gly Cys Gly Gly Gly Asp
1               5                   10                  15

Arg Val Tyr Ile His Pro Phe
            20

<210> SEQ ID NO 169
<211> LENGTH: 24
<212> TYPE: PRT
<213> ORGANISM: Unknown
<220> FEATURE:
<223> OTHER INFORMATION: Angiotensin derivative

<400> SEQUENCE: 169

Leu His Phe Pro His Ile Tyr Val Arg Asp Gly Gly Cys Gly Gly Gly

```
                1               5                  10                  15
Asp Arg Val Tyr Ile His Pro Phe
            20

<210> SEQ ID NO 170
<211> LENGTH: 25
<212> TYPE: PRT
<213> ORGANISM: Unknown
<220> FEATURE:
<223> OTHER INFORMATION: Angiotensin derivative

<400> SEQUENCE: 170

Leu His Phe Pro His Ile Tyr Val Arg Asp Gly Gly Gly Cys Gly Gly
1               5                   10                  15

Gly Asp Arg Val Tyr Ile His Pro Phe
            20                  25

<210> SEQ ID NO 171
<211> LENGTH: 26
<212> TYPE: PRT
<213> ORGANISM: Unknown
<220> FEATURE:
<223> OTHER INFORMATION: Angiotensin derivative

<400> SEQUENCE: 171

Leu His Phe Pro His Ile Tyr Val Arg Asp Gly Gly Gly Gly Cys Gly
1               5                   10                  15

Gly Gly Asp Arg Val Tyr Ile His Pro Phe
            20                  25

<210> SEQ ID NO 172
<211> LENGTH: 27
<212> TYPE: PRT
<213> ORGANISM: Unknown
<220> FEATURE:
<223> OTHER INFORMATION: Angiotensin derivative

<400> SEQUENCE: 172

Leu His Phe Pro His Ile Tyr Val Arg Asp Gly Gly Gly Gly Gly Cys
1               5                   10                  15

Gly Gly Gly Asp Arg Val Tyr Ile His Pro Phe
            20                  25

<210> SEQ ID NO 173
<211> LENGTH: 28
<212> TYPE: PRT
<213> ORGANISM: Unknown
<220> FEATURE:
<223> OTHER INFORMATION: Angiotensin derivative

<400> SEQUENCE: 173

Leu His Phe Pro His Ile Tyr Val Arg Asp Gly Gly Gly Gly Gly Gly
1               5                   10                  15

Cys Gly Gly Gly Asp Arg Val Tyr Ile His Pro Phe
            20                  25

<210> SEQ ID NO 174
<211> LENGTH: 24
<212> TYPE: PRT
<213> ORGANISM: Unknown
<220> FEATURE:
<223> OTHER INFORMATION: Angiotensin derivative

<400> SEQUENCE: 174
```

Leu His Phe Pro His Ile Tyr Val Arg Asp Gly Cys Gly Gly Gly Gly
1               5                   10                  15

Asp Arg Val Tyr Ile His Pro Phe
            20

<210> SEQ ID NO 175
<211> LENGTH: 25
<212> TYPE: PRT
<213> ORGANISM: Unknown
<220> FEATURE:
<223> OTHER INFORMATION: Angiotensin derivative

<400> SEQUENCE: 175

Leu His Phe Pro His Ile Tyr Val Arg Asp Gly Gly Cys Gly Gly Gly
1               5                   10                  15

Gly Asp Arg Val Tyr Ile His Pro Phe
            20                  25

<210> SEQ ID NO 176
<211> LENGTH: 26
<212> TYPE: PRT
<213> ORGANISM: Unknown
<220> FEATURE:
<223> OTHER INFORMATION: Angiotensin derivative

<400> SEQUENCE: 176

Leu His Phe Pro His Ile Tyr Val Arg Asp Gly Gly Gly Cys Gly Gly
1               5                   10                  15

Gly Gly Asp Arg Val Tyr Ile His Pro Phe
            20                  25

<210> SEQ ID NO 177
<211> LENGTH: 27
<212> TYPE: PRT
<213> ORGANISM: Unknown
<220> FEATURE:
<223> OTHER INFORMATION: Angiotensin derivative

<400> SEQUENCE: 177

Leu His Phe Pro His Ile Tyr Val Arg Asp Gly Gly Gly Gly Cys Gly
1               5                   10                  15

Gly Gly Gly Asp Arg Val Tyr Ile His Pro Phe
            20                  25

<210> SEQ ID NO 178
<211> LENGTH: 28
<212> TYPE: PRT
<213> ORGANISM: Unknown
<220> FEATURE:
<223> OTHER INFORMATION: Angiotensin derivative

<400> SEQUENCE: 178

Leu His Phe Pro His Ile Tyr Val Arg Asp Gly Gly Gly Gly Gly Cys
1               5                   10                  15

Gly Gly Gly Gly Asp Arg Val Tyr Ile His Pro Phe
            20                  25

<210> SEQ ID NO 179
<211> LENGTH: 29
<212> TYPE: PRT
<213> ORGANISM: Unknown
<220> FEATURE:
<223> OTHER INFORMATION: Angiotensin derivative

<400> SEQUENCE: 179

Leu His Phe Pro His Ile Tyr Val Arg Asp Gly Gly Gly Gly Gly
1               5                   10                  15

Cys Gly Gly Gly Gly Asp Arg Val Tyr Ile His Pro Phe
                20                  25

<210> SEQ ID NO 180
<211> LENGTH: 25
<212> TYPE: PRT
<213> ORGANISM: Unknown
<220> FEATURE:
<223> OTHER INFORMATION: Angiotensin derivative

<400> SEQUENCE: 180

Leu His Phe Pro His Ile Tyr Val Arg Asp Gly Cys Gly Gly Gly
1               5                   10                  15

Gly Asp Arg Val Tyr Ile His Pro Phe
                20                  25

<210> SEQ ID NO 181
<211> LENGTH: 26
<212> TYPE: PRT
<213> ORGANISM: Unknown
<220> FEATURE:
<223> OTHER INFORMATION: Angiotensin derivative

<400> SEQUENCE: 181

Leu His Phe Pro His Ile Tyr Val Arg Asp Gly Gly Cys Gly Gly
1               5                   10                  15

Gly Gly Asp Arg Val Tyr Ile His Pro Phe
                20                  25

<210> SEQ ID NO 182
<211> LENGTH: 27
<212> TYPE: PRT
<213> ORGANISM: Unknown
<220> FEATURE:
<223> OTHER INFORMATION: Angiotensin derivative

<400> SEQUENCE: 182

Leu His Phe Pro His Ile Tyr Val Arg Asp Gly Gly Gly Cys Gly
1               5                   10                  15

Gly Gly Gly Asp Arg Val Tyr Ile His Pro Phe
                20                  25

<210> SEQ ID NO 183
<211> LENGTH: 28
<212> TYPE: PRT
<213> ORGANISM: Unknown
<220> FEATURE:
<223> OTHER INFORMATION: Angiotensin derivative

<400> SEQUENCE: 183

Leu His Phe Pro His Ile Tyr Val Arg Asp Gly Gly Gly Gly Cys Gly
1               5                   10                  15

Gly Gly Gly Gly Asp Arg Val Tyr Ile His Pro Phe
                20                  25

<210> SEQ ID NO 184
<211> LENGTH: 29
<212> TYPE: PRT
<213> ORGANISM: Unknown
<220> FEATURE:
<223> OTHER INFORMATION: Angiotensin derivative

<400> SEQUENCE: 184

Leu His Phe Pro His Ile Tyr Val Arg Asp Gly Gly Gly Gly Cys
1               5                  10                  15

Gly Gly Gly Gly Gly Asp Arg Val Tyr Ile His Pro Phe
            20                  25

<210> SEQ ID NO 185
<211> LENGTH: 30
<212> TYPE: PRT
<213> ORGANISM: Unknown
<220> FEATURE:
<223> OTHER INFORMATION: Angiotensin derivative

<400> SEQUENCE: 185

Leu His Phe Pro His Ile Tyr Val Arg Asp Gly Gly Gly Gly Gly
1               5                  10                  15

Cys Gly Gly Gly Gly Gly Asp Arg Val Tyr Ile His Pro Phe
            20                  25                  30

<210> SEQ ID NO 186
<211> LENGTH: 26
<212> TYPE: PRT
<213> ORGANISM: Unknown
<220> FEATURE:
<223> OTHER INFORMATION: Angiotensin derivative

<400> SEQUENCE: 186

Leu His Phe Pro His Ile Tyr Val Arg Asp Gly Cys Gly Gly Gly
1               5                  10                  15

Gly Gly Asp Arg Val Tyr Ile His Pro Phe
            20                  25

<210> SEQ ID NO 187
<211> LENGTH: 27
<212> TYPE: PRT
<213> ORGANISM: Unknown
<220> FEATURE:
<223> OTHER INFORMATION: Angiotensin derivative

<400> SEQUENCE: 187

Leu His Phe Pro His Ile Tyr Val Arg Asp Gly Gly Cys Gly Gly
1               5                  10                  15

Gly Gly Gly Asp Arg Val Tyr Ile His Pro Phe
            20                  25

<210> SEQ ID NO 188
<211> LENGTH: 28
<212> TYPE: PRT
<213> ORGANISM: Unknown
<220> FEATURE:
<223> OTHER INFORMATION: Angiotensin derivative

<400> SEQUENCE: 188

Leu His Phe Pro His Ile Tyr Val Arg Asp Gly Gly Gly Cys Gly
1               5                  10                  15

Gly Gly Gly Gly Asp Arg Val Tyr Ile His Pro Phe
            20                  25

<210> SEQ ID NO 189
<211> LENGTH: 29
<212> TYPE: PRT
<213> ORGANISM: Unknown
<220> FEATURE:
<223> OTHER INFORMATION: Angiotensin derivative

```
<400> SEQUENCE: 189

Leu His Phe Pro His Ile Tyr Val Arg Asp Gly Gly Gly Cys Gly
1               5                   10                  15

Gly Gly Gly Gly Gly Asp Arg Val Tyr Ile His Pro Phe
            20                  25

<210> SEQ ID NO 190
<211> LENGTH: 30
<212> TYPE: PRT
<213> ORGANISM: Unknown
<220> FEATURE:
<223> OTHER INFORMATION: Angiotensin derivative

<400> SEQUENCE: 190

Leu His Phe Pro His Ile Tyr Val Arg Asp Gly Gly Gly Gly Cys
1               5                   10                  15

Gly Gly Gly Gly Gly Gly Asp Arg Val Tyr Ile His Pro Phe
            20                  25                  30

<210> SEQ ID NO 191
<211> LENGTH: 31
<212> TYPE: PRT
<213> ORGANISM: Unknown
<220> FEATURE:
<223> OTHER INFORMATION: Angiotensin derivative

<400> SEQUENCE: 191

Leu His Phe Pro His Ile Tyr Val Arg Asp Gly Gly Gly Gly Gly
1               5                   10                  15

Cys Gly Gly Gly Gly Gly Gly Asp Arg Val Tyr Ile His Pro Phe
            20                  25                  30

<210> SEQ ID NO 192
<211> LENGTH: 22
<212> TYPE: PRT
<213> ORGANISM: Unknown
<220> FEATURE:
<223> OTHER INFORMATION: Angiotensin derivative

<400> SEQUENCE: 192

Asp Arg Val Tyr Ile His Pro Phe Gly Gly Cys Gly Asp Arg Val Tyr
1               5                   10                  15

Ile His Pro Phe His Leu
            20

<210> SEQ ID NO 193
<211> LENGTH: 23
<212> TYPE: PRT
<213> ORGANISM: Unknown
<220> FEATURE:
<223> OTHER INFORMATION: Angiotensin derivative

<400> SEQUENCE: 193

Asp Arg Val Tyr Ile His Pro Phe Gly Gly Gly Cys Gly Asp Arg Val
1               5                   10                  15

Tyr Ile His Pro Phe His Leu
            20

<210> SEQ ID NO 194
<211> LENGTH: 24
<212> TYPE: PRT
<213> ORGANISM: Unknown
<220> FEATURE:
```

<223> OTHER INFORMATION: Angiotensin derivative

<400> SEQUENCE: 194

Asp Arg Val Tyr Ile His Pro Phe Gly Gly Gly Gly Cys Gly Asp Arg
1               5                   10                  15

Val Tyr Ile His Pro Phe His Leu
            20

<210> SEQ ID NO 195
<211> LENGTH: 25
<212> TYPE: PRT
<213> ORGANISM: Unknown
<220> FEATURE:
<223> OTHER INFORMATION: Angiotensin derivative

<400> SEQUENCE: 195

Asp Arg Val Tyr Ile His Pro Phe Gly Gly Gly Gly Gly Cys Gly Asp
1               5                   10                  15

Arg Val Tyr Ile His Pro Phe His Leu
            20                  25

<210> SEQ ID NO 196
<211> LENGTH: 26
<212> TYPE: PRT
<213> ORGANISM: Unknown
<220> FEATURE:
<223> OTHER INFORMATION: Angiotensin derivative

<400> SEQUENCE: 196

Asp Arg Val Tyr Ile His Pro Phe Gly Gly Gly Gly Gly Gly Cys Gly
1               5                   10                  15

Asp Arg Val Tyr Ile His Pro Phe His Leu
            20                  25

<210> SEQ ID NO 197
<211> LENGTH: 22
<212> TYPE: PRT
<213> ORGANISM: Unknown
<220> FEATURE:
<223> OTHER INFORMATION: Angiotensin derivative

<400> SEQUENCE: 197

Asp Arg Val Tyr Ile His Pro Phe Gly Cys Gly Gly Asp Arg Val Tyr
1               5                   10                  15

Ile His Pro Phe His Leu
            20

<210> SEQ ID NO 198
<211> LENGTH: 23
<212> TYPE: PRT
<213> ORGANISM: Unknown
<220> FEATURE:
<223> OTHER INFORMATION: Angiotensin derivative

<400> SEQUENCE: 198

Asp Arg Val Tyr Ile His Pro Phe Gly Gly Cys Gly Gly Asp Arg Val
1               5                   10                  15

Tyr Ile His Pro Phe His Leu
            20

<210> SEQ ID NO 199
<211> LENGTH: 24
<212> TYPE: PRT
<213> ORGANISM: Unknown

```
<220> FEATURE:
<223> OTHER INFORMATION: Angiotensin derivative

<400> SEQUENCE: 199

Asp Arg Val Tyr Ile His Pro Phe Gly Gly Gly Cys Gly Gly Asp Arg
1               5                   10                  15

Val Tyr Ile His Pro Phe His Leu
            20

<210> SEQ ID NO 200
<211> LENGTH: 25
<212> TYPE: PRT
<213> ORGANISM: Unknown
<220> FEATURE:
<223> OTHER INFORMATION: Angiotensin derivative

<400> SEQUENCE: 200

Asp Arg Val Tyr Ile His Pro Phe Gly Gly Gly Gly Cys Gly Gly Asp
1               5                   10                  15

Arg Val Tyr Ile His Pro Phe His Leu
            20                  25

<210> SEQ ID NO 201
<211> LENGTH: 26
<212> TYPE: PRT
<213> ORGANISM: Unknown
<220> FEATURE:
<223> OTHER INFORMATION: Angiotensin derivative

<400> SEQUENCE: 201

Asp Arg Val Tyr Ile His Pro Phe Gly Gly Gly Gly Gly Cys Gly Gly
1               5                   10                  15

Asp Arg Val Tyr Ile His Pro Phe His Leu
            20                  25

<210> SEQ ID NO 202
<211> LENGTH: 27
<212> TYPE: PRT
<213> ORGANISM: Unknown
<220> FEATURE:
<223> OTHER INFORMATION: Angiotensin derivative

<400> SEQUENCE: 202

Asp Arg Val Tyr Ile His Pro Phe Gly Gly Gly Gly Gly Gly Cys Gly
1               5                   10                  15

Gly Asp Arg Val Tyr Ile His Pro Phe His Leu
            20                  25

<210> SEQ ID NO 203
<211> LENGTH: 23
<212> TYPE: PRT
<213> ORGANISM: Unknown
<220> FEATURE:
<223> OTHER INFORMATION: Angiotensin derivative

<400> SEQUENCE: 203

Asp Arg Val Tyr Ile His Pro Phe Gly Cys Gly Gly Gly Asp Arg Val
1               5                   10                  15

Tyr Ile His Pro Phe His Leu
            20

<210> SEQ ID NO 204
<211> LENGTH: 24
<212> TYPE: PRT
```

```
<213> ORGANISM: Unknown
<220> FEATURE:
<223> OTHER INFORMATION: Angiotensin derivative

<400> SEQUENCE: 204

Asp Arg Val Tyr Ile His Pro Phe Gly Gly Cys Gly Gly Gly Asp Arg
1               5                   10                  15

Val Tyr Ile His Pro Phe His Leu
            20

<210> SEQ ID NO 205
<211> LENGTH: 25
<212> TYPE: PRT
<213> ORGANISM: Unknown
<220> FEATURE:
<223> OTHER INFORMATION: Angiotensin derivative

<400> SEQUENCE: 205

Asp Arg Val Tyr Ile His Pro Phe Gly Gly Gly Cys Gly Gly Gly Asp
1               5                   10                  15

Arg Val Tyr Ile His Pro Phe His Leu
            20                  25

<210> SEQ ID NO 206
<211> LENGTH: 26
<212> TYPE: PRT
<213> ORGANISM: Unknown
<220> FEATURE:
<223> OTHER INFORMATION: Angiotensin derivative

<400> SEQUENCE: 206

Asp Arg Val Tyr Ile His Pro Phe Gly Gly Gly Gly Cys Gly Gly Gly
1               5                   10                  15

Asp Arg Val Tyr Ile His Pro Phe His Leu
            20                  25

<210> SEQ ID NO 207
<211> LENGTH: 27
<212> TYPE: PRT
<213> ORGANISM: Unknown
<220> FEATURE:
<223> OTHER INFORMATION: Angiotensin derivative

<400> SEQUENCE: 207

Asp Arg Val Tyr Ile His Pro Phe Gly Gly Gly Gly Gly Cys Gly Gly
1               5                   10                  15

Gly Asp Arg Val Tyr Ile His Pro Phe His Leu
            20                  25

<210> SEQ ID NO 208
<211> LENGTH: 28
<212> TYPE: PRT
<213> ORGANISM: Unknown
<220> FEATURE:
<223> OTHER INFORMATION: Angiotensin derivative

<400> SEQUENCE: 208

Asp Arg Val Tyr Ile His Pro Phe Gly Gly Gly Gly Gly Gly Cys Gly
1               5                   10                  15

Gly Gly Asp Arg Val Tyr Ile His Pro Phe His Leu
            20                  25

<210> SEQ ID NO 209
<211> LENGTH: 24
```

-continued

<212> TYPE: PRT
<213> ORGANISM: Unknown
<220> FEATURE:
<223> OTHER INFORMATION: Angiotensin derivative

<400> SEQUENCE: 209

Asp Arg Val Tyr Ile His Pro Phe Gly Cys Gly Gly Gly Gly Asp Arg
1               5                   10                  15

Val Tyr Ile His Pro Phe His Leu
            20

<210> SEQ ID NO 210
<211> LENGTH: 25
<212> TYPE: PRT
<213> ORGANISM: Unknown
<220> FEATURE:
<223> OTHER INFORMATION: Angiotensin derivative

<400> SEQUENCE: 210

Asp Arg Val Tyr Ile His Pro Phe Gly Gly Cys Gly Gly Gly Gly Asp
1               5                   10                  15

Arg Val Tyr Ile His Pro Phe His Leu
            20                  25

<210> SEQ ID NO 211
<211> LENGTH: 26
<212> TYPE: PRT
<213> ORGANISM: Unknown
<220> FEATURE:
<223> OTHER INFORMATION: Angiotensin derivative

<400> SEQUENCE: 211

Asp Arg Val Tyr Ile His Pro Phe Gly Gly Gly Cys Gly Gly Gly Gly
1               5                   10                  15

Asp Arg Val Tyr Ile His Pro Phe His Leu
            20                  25

<210> SEQ ID NO 212
<211> LENGTH: 27
<212> TYPE: PRT
<213> ORGANISM: Unknown
<220> FEATURE:
<223> OTHER INFORMATION: Angiotensin derivative

<400> SEQUENCE: 212

Asp Arg Val Tyr Ile His Pro Phe Gly Gly Gly Gly Cys Gly Gly Gly
1               5                   10                  15

Gly Asp Arg Val Tyr Ile His Pro Phe His Leu
            20                  25

<210> SEQ ID NO 213
<211> LENGTH: 28
<212> TYPE: PRT
<213> ORGANISM: Unknown
<220> FEATURE:
<223> OTHER INFORMATION: Angiotensin derivative

<400> SEQUENCE: 213

Asp Arg Val Tyr Ile His Pro Phe Gly Gly Gly Gly Gly Cys Gly Gly
1               5                   10                  15

Gly Gly Asp Arg Val Tyr Ile His Pro Phe His Leu
            20                  25

<210> SEQ ID NO 214

```
<211> LENGTH: 29
<212> TYPE: PRT
<213> ORGANISM: Unknown
<220> FEATURE:
<223> OTHER INFORMATION: Angiotensin derivative

<400> SEQUENCE: 214

Asp Arg Val Tyr Ile His Pro Phe Gly Gly Gly Gly Gly Cys Gly
1               5                   10                  15

Gly Gly Gly Asp Arg Val Tyr Ile His Pro Phe His Leu
            20                  25

<210> SEQ ID NO 215
<211> LENGTH: 25
<212> TYPE: PRT
<213> ORGANISM: Unknown
<220> FEATURE:
<223> OTHER INFORMATION: Angiotensin derivative

<400> SEQUENCE: 215

Asp Arg Val Tyr Ile His Pro Phe Gly Cys Gly Gly Gly Gly Asp
1               5                   10                  15

Arg Val Tyr Ile His Pro Phe His Leu
            20                  25

<210> SEQ ID NO 216
<211> LENGTH: 26
<212> TYPE: PRT
<213> ORGANISM: Unknown
<220> FEATURE:
<223> OTHER INFORMATION: Angiotensin derivative

<400> SEQUENCE: 216

Asp Arg Val Tyr Ile His Pro Phe Gly Gly Cys Gly Gly Gly Gly
1               5                   10                  15

Asp Arg Val Tyr Ile His Pro Phe His Leu
            20                  25

<210> SEQ ID NO 217
<211> LENGTH: 27
<212> TYPE: PRT
<213> ORGANISM: Unknown
<220> FEATURE:
<223> OTHER INFORMATION: Angiotensin derivative

<400> SEQUENCE: 217

Asp Arg Val Tyr Ile His Pro Phe Gly Gly Gly Cys Gly Gly Gly
1               5                   10                  15

Gly Asp Arg Val Tyr Ile His Pro Phe His Leu
            20                  25

<210> SEQ ID NO 218
<211> LENGTH: 28
<212> TYPE: PRT
<213> ORGANISM: Unknown
<220> FEATURE:
<223> OTHER INFORMATION: Angiotensin derivative

<400> SEQUENCE: 218

Asp Arg Val Tyr Ile His Pro Phe Gly Gly Gly Gly Cys Gly Gly
1               5                   10                  15

Gly Gly Asp Arg Val Tyr Ile His Pro Phe His Leu
            20                  25
```

```
<210> SEQ ID NO 219
<211> LENGTH: 29
<212> TYPE: PRT
<213> ORGANISM: Unknown
<220> FEATURE:
<223> OTHER INFORMATION: Angiotensin derivative

<400> SEQUENCE: 219

Asp Arg Val Tyr Ile His Pro Phe Gly Gly Gly Gly Cys Gly Gly
1               5                   10                  15

Gly Gly Gly Asp Arg Val Tyr Ile His Pro Phe His Leu
            20                  25

<210> SEQ ID NO 220
<211> LENGTH: 30
<212> TYPE: PRT
<213> ORGANISM: Unknown
<220> FEATURE:
<223> OTHER INFORMATION: Angiotensin derivative

<400> SEQUENCE: 220

Asp Arg Val Tyr Ile His Pro Phe Gly Gly Gly Gly Gly Cys Gly
1               5                   10                  15

Gly Gly Gly Gly Asp Arg Val Tyr Ile His Pro Phe His Leu
            20                  25                  30

<210> SEQ ID NO 221
<211> LENGTH: 26
<212> TYPE: PRT
<213> ORGANISM: Unknown
<220> FEATURE:
<223> OTHER INFORMATION: Angiotensin derivative

<400> SEQUENCE: 221

Asp Arg Val Tyr Ile His Pro Phe Gly Cys Gly Gly Gly Gly Gly
1               5                   10                  15

Asp Arg Val Tyr Ile His Pro Phe His Leu
            20                  25

<210> SEQ ID NO 222
<211> LENGTH: 27
<212> TYPE: PRT
<213> ORGANISM: Unknown
<220> FEATURE:
<223> OTHER INFORMATION: Angiotensin derivative

<400> SEQUENCE: 222

Asp Arg Val Tyr Ile His Pro Phe Gly Gly Cys Gly Gly Gly Gly
1               5                   10                  15

Gly Asp Arg Val Tyr Ile His Pro Phe His Leu
            20                  25

<210> SEQ ID NO 223
<211> LENGTH: 28
<212> TYPE: PRT
<213> ORGANISM: Unknown
<220> FEATURE:
<223> OTHER INFORMATION: Angiotensin derivative

<400> SEQUENCE: 223

Asp Arg Val Tyr Ile His Pro Phe Gly Gly Gly Cys Gly Gly Gly
1               5                   10                  15

Gly Gly Asp Arg Val Tyr Ile His Pro Phe His Leu
            20                  25
```

```
<210> SEQ ID NO 224
<211> LENGTH: 29
<212> TYPE: PRT
<213> ORGANISM: Unknown
<220> FEATURE:
<223> OTHER INFORMATION: Angiotensin derivative

<400> SEQUENCE: 224

Asp Arg Val Tyr Ile His Pro Phe Gly Gly Gly Cys Gly Gly
1               5                   10                  15

Gly Gly Gly Asp Arg Val Tyr Ile His Pro Phe His Leu
            20                  25

<210> SEQ ID NO 225
<211> LENGTH: 30
<212> TYPE: PRT
<213> ORGANISM: Unknown
<220> FEATURE:
<223> OTHER INFORMATION: Angiotensin derivative

<400> SEQUENCE: 225

Asp Arg Val Tyr Ile His Pro Phe Gly Gly Gly Gly Cys Gly Gly
1               5                   10                  15

Gly Gly Gly Gly Asp Arg Val Tyr Ile His Pro Phe His Leu
            20                  25                  30

<210> SEQ ID NO 226
<211> LENGTH: 31
<212> TYPE: PRT
<213> ORGANISM: Unknown
<220> FEATURE:
<223> OTHER INFORMATION: Angiotensin derivative

<400> SEQUENCE: 226

Asp Arg Val Tyr Ile His Pro Phe Gly Gly Gly Gly Gly Cys Gly
1               5                   10                  15

Gly Gly Gly Gly Gly Asp Arg Val Tyr Ile His Pro Phe His Leu
            20                  25                  30

<210> SEQ ID NO 227
<211> LENGTH: 20
<212> TYPE: PRT
<213> ORGANISM: Unknown
<220> FEATURE:
<223> OTHER INFORMATION: Angiotensin derivative

<400> SEQUENCE: 227

Asp Arg Val Tyr Ile His Pro Phe Gly Gly Cys Gly Asp Arg Val Tyr
1               5                   10                  15

Ile His Pro Phe
            20

<210> SEQ ID NO 228
<211> LENGTH: 21
<212> TYPE: PRT
<213> ORGANISM: Unknown
<220> FEATURE:
<223> OTHER INFORMATION: Angiotensin derivative

<400> SEQUENCE: 228

Asp Arg Val Tyr Ile His Pro Phe Gly Gly Gly Cys Gly Asp Arg Val
1               5                   10                  15

Tyr Ile His Pro Phe
            20
```

```
<210> SEQ ID NO 229
<211> LENGTH: 22
<212> TYPE: PRT
<213> ORGANISM: Unknown
<220> FEATURE:
<223> OTHER INFORMATION: Angiotensin derivative

<400> SEQUENCE: 229

Asp Arg Val Tyr Ile His Pro Phe Gly Gly Gly Gly Cys Gly Asp Arg
1               5                   10                  15

Val Tyr Ile His Pro Phe
            20

<210> SEQ ID NO 230
<211> LENGTH: 23
<212> TYPE: PRT
<213> ORGANISM: Unknown
<220> FEATURE:
<223> OTHER INFORMATION: Angiotensin derivative

<400> SEQUENCE: 230

Asp Arg Val Tyr Ile His Pro Phe Gly Gly Gly Gly Gly Cys Gly Asp
1               5                   10                  15

Arg Val Tyr Ile His Pro Phe
            20

<210> SEQ ID NO 231
<211> LENGTH: 24
<212> TYPE: PRT
<213> ORGANISM: Unknown
<220> FEATURE:
<223> OTHER INFORMATION: Angiotensin derivative

<400> SEQUENCE: 231

Asp Arg Val Tyr Ile His Pro Phe Gly Gly Gly Gly Gly Gly Cys Gly
1               5                   10                  15

Asp Arg Val Tyr Ile His Pro Phe
            20

<210> SEQ ID NO 232
<211> LENGTH: 20
<212> TYPE: PRT
<213> ORGANISM: Unknown
<220> FEATURE:
<223> OTHER INFORMATION: Angiotensin derivative

<400> SEQUENCE: 232

Asp Arg Val Tyr Ile His Pro Phe Gly Cys Gly Gly Asp Arg Val Tyr
1               5                   10                  15

Ile His Pro Phe
            20

<210> SEQ ID NO 233
<211> LENGTH: 21
<212> TYPE: PRT
<213> ORGANISM: Unknown
<220> FEATURE:
<223> OTHER INFORMATION: Angiotensin derivative

<400> SEQUENCE: 233

Asp Arg Val Tyr Ile His Pro Phe Gly Gly Cys Gly Gly Asp Arg Val
1               5                   10                  15

Tyr Ile His Pro Phe
```

-continued

```
            20

<210> SEQ ID NO 234
<211> LENGTH: 22
<212> TYPE: PRT
<213> ORGANISM: Unknown
<220> FEATURE:
<223> OTHER INFORMATION: Angiotensin derivative

<400> SEQUENCE: 234

Asp Arg Val Tyr Ile His Pro Phe Gly Gly Gly Cys Gly Gly Asp Arg
1               5                   10                  15

Val Tyr Ile His Pro Phe
            20

<210> SEQ ID NO 235
<211> LENGTH: 23
<212> TYPE: PRT
<213> ORGANISM: Unknown
<220> FEATURE:
<223> OTHER INFORMATION: Angiotensin derivative

<400> SEQUENCE: 235

Asp Arg Val Tyr Ile His Pro Phe Gly Gly Gly Gly Cys Gly Gly Asp
1               5                   10                  15

Arg Val Tyr Ile His Pro Phe
            20

<210> SEQ ID NO 236
<211> LENGTH: 24
<212> TYPE: PRT
<213> ORGANISM: Unknown
<220> FEATURE:
<223> OTHER INFORMATION: Angiotensin derivative

<400> SEQUENCE: 236

Asp Arg Val Tyr Ile His Pro Phe Gly Gly Gly Gly Cys Gly Gly
1               5                   10                  15

Asp Arg Val Tyr Ile His Pro Phe
            20

<210> SEQ ID NO 237
<211> LENGTH: 25
<212> TYPE: PRT
<213> ORGANISM: Unknown
<220> FEATURE:
<223> OTHER INFORMATION: Angiotensin derivative

<400> SEQUENCE: 237

Asp Arg Val Tyr Ile His Pro Phe Gly Gly Gly Gly Gly Cys Gly
1               5                   10                  15

Gly Asp Arg Val Tyr Ile His Pro Phe
            20                  25

<210> SEQ ID NO 238
<211> LENGTH: 21
<212> TYPE: PRT
<213> ORGANISM: Unknown
<220> FEATURE:
<223> OTHER INFORMATION: Angiotensin derivative

<400> SEQUENCE: 238

Asp Arg Val Tyr Ile His Pro Phe Gly Cys Gly Gly Gly Asp Arg Val
1               5                   10                  15
```

```
Tyr Ile His Pro Phe
            20

<210> SEQ ID NO 239
<211> LENGTH: 22
<212> TYPE: PRT
<213> ORGANISM: Unknown
<220> FEATURE:
<223> OTHER INFORMATION: Angiotensin derivative

<400> SEQUENCE: 239

Asp Arg Val Tyr Ile His Pro Phe Gly Gly Cys Gly Gly Gly Asp Arg
1               5                   10                  15

Val Tyr Ile His Pro Phe
            20

<210> SEQ ID NO 240
<211> LENGTH: 23
<212> TYPE: PRT
<213> ORGANISM: Unknown
<220> FEATURE:
<223> OTHER INFORMATION: Angiotensin derivative

<400> SEQUENCE: 240

Asp Arg Val Tyr Ile His Pro Phe Gly Gly Gly Cys Gly Gly Gly Asp
1               5                   10                  15

Arg Val Tyr Ile His Pro Phe
            20

<210> SEQ ID NO 241
<211> LENGTH: 24
<212> TYPE: PRT
<213> ORGANISM: Unknown
<220> FEATURE:
<223> OTHER INFORMATION: Angiotensin derivative

<400> SEQUENCE: 241

Asp Arg Val Tyr Ile His Pro Phe Gly Gly Gly Gly Cys Gly Gly Gly
1               5                   10                  15

Asp Arg Val Tyr Ile His Pro Phe
            20

<210> SEQ ID NO 242
<211> LENGTH: 25
<212> TYPE: PRT
<213> ORGANISM: Unknown
<220> FEATURE:
<223> OTHER INFORMATION: Angiotensin derivative

<400> SEQUENCE: 242

Asp Arg Val Tyr Ile His Pro Phe Gly Gly Gly Gly Gly Cys Gly Gly
1               5                   10                  15

Gly Asp Arg Val Tyr Ile His Pro Phe
            20                  25

<210> SEQ ID NO 243
<211> LENGTH: 26
<212> TYPE: PRT
<213> ORGANISM: Unknown
<220> FEATURE:
<223> OTHER INFORMATION: Angiotensin derivative

<400> SEQUENCE: 243

Asp Arg Val Tyr Ile His Pro Phe Gly Gly Gly Gly Gly Gly Cys Gly
1               5                   10                  15
```

```
Gly Gly Asp Arg Val Tyr Ile His Pro Phe
        20                  25

<210> SEQ ID NO 244
<211> LENGTH: 22
<212> TYPE: PRT
<213> ORGANISM: Unknown
<220> FEATURE:
<223> OTHER INFORMATION: Angiotensin derivative

<400> SEQUENCE: 244

Asp Arg Val Tyr Ile His Pro Phe Gly Cys Gly Gly Gly Gly Asp Arg
1               5                   10                  15

Val Tyr Ile His Pro Phe
        20

<210> SEQ ID NO 245
<211> LENGTH: 23
<212> TYPE: PRT
<213> ORGANISM: Unknown
<220> FEATURE:
<223> OTHER INFORMATION: Angiotensin derivative

<400> SEQUENCE: 245

Asp Arg Val Tyr Ile His Pro Phe Gly Gly Cys Gly Gly Gly Gly Asp
1               5                   10                  15

Arg Val Tyr Ile His Pro Phe
        20

<210> SEQ ID NO 246
<211> LENGTH: 24
<212> TYPE: PRT
<213> ORGANISM: Unknown
<220> FEATURE:
<223> OTHER INFORMATION: Angiotensin derivative

<400> SEQUENCE: 246

Asp Arg Val Tyr Ile His Pro Phe Gly Gly Gly Cys Gly Gly Gly Gly
1               5                   10                  15

Asp Arg Val Tyr Ile His Pro Phe
        20

<210> SEQ ID NO 247
<211> LENGTH: 25
<212> TYPE: PRT
<213> ORGANISM: Unknown
<220> FEATURE:
<223> OTHER INFORMATION: Angiotensin derivative

<400> SEQUENCE: 247

Asp Arg Val Tyr Ile His Pro Phe Gly Gly Gly Gly Cys Gly Gly Gly
1               5                   10                  15

Gly Asp Arg Val Tyr Ile His Pro Phe
        20                  25

<210> SEQ ID NO 248
<211> LENGTH: 26
<212> TYPE: PRT
<213> ORGANISM: Unknown
<220> FEATURE:
<223> OTHER INFORMATION: Angiotensin derivative

<400> SEQUENCE: 248

Asp Arg Val Tyr Ile His Pro Phe Gly Gly Gly Gly Gly Cys Gly Gly
```

```
                1               5                  10                  15
Gly Gly Asp Arg Val Tyr Ile His Pro Phe
            20                  25

<210> SEQ ID NO 249
<211> LENGTH: 27
<212> TYPE: PRT
<213> ORGANISM: Unknown
<220> FEATURE:
<223> OTHER INFORMATION: Angiotensin derivative

<400> SEQUENCE: 249

Asp Arg Val Tyr Ile His Pro Phe Gly Gly Gly Gly Gly Cys Gly
1               5                  10                  15

Gly Gly Gly Asp Arg Val Tyr Ile His Pro Phe
            20                  25

<210> SEQ ID NO 250
<211> LENGTH: 23
<212> TYPE: PRT
<213> ORGANISM: Unknown
<220> FEATURE:
<223> OTHER INFORMATION: Angiotensin derivative

<400> SEQUENCE: 250

Asp Arg Val Tyr Ile His Pro Phe Gly Cys Gly Gly Gly Gly Asp
1               5                  10                  15

Arg Val Tyr Ile His Pro Phe
            20

<210> SEQ ID NO 251
<211> LENGTH: 24
<212> TYPE: PRT
<213> ORGANISM: Unknown
<220> FEATURE:
<223> OTHER INFORMATION: Angiotensin derivative

<400> SEQUENCE: 251

Asp Arg Val Tyr Ile His Pro Phe Gly Gly Cys Gly Gly Gly Gly
1               5                  10                  15

Asp Arg Val Tyr Ile His Pro Phe
            20

<210> SEQ ID NO 252
<211> LENGTH: 25
<212> TYPE: PRT
<213> ORGANISM: Unknown
<220> FEATURE:
<223> OTHER INFORMATION: Angiotensin derivative

<400> SEQUENCE: 252

Asp Arg Val Tyr Ile His Pro Phe Gly Gly Gly Cys Gly Gly Gly
1               5                  10                  15

Gly Asp Arg Val Tyr Ile His Pro Phe
            20                  25

<210> SEQ ID NO 253
<211> LENGTH: 26
<212> TYPE: PRT
<213> ORGANISM: Unknown
<220> FEATURE:
<223> OTHER INFORMATION: Angiotensin derivative

<400> SEQUENCE: 253
```

```
Asp Arg Val Tyr Ile His Pro Phe Gly Gly Gly Gly Cys Gly Gly Gly
1               5                   10                  15

Gly Gly Asp Arg Val Tyr Ile His Pro Phe
            20                  25
```

<210> SEQ ID NO 254
<211> LENGTH: 27
<212> TYPE: PRT
<213> ORGANISM: Unknown
<220> FEATURE:
<223> OTHER INFORMATION: Angiotensin derivative

<400> SEQUENCE: 254

```
Asp Arg Val Tyr Ile His Pro Phe Gly Gly Gly Gly Cys Gly Gly
1               5                   10                  15

Gly Gly Gly Asp Arg Val Tyr Ile His Pro Phe
            20                  25
```

<210> SEQ ID NO 255
<211> LENGTH: 28
<212> TYPE: PRT
<213> ORGANISM: Unknown
<220> FEATURE:
<223> OTHER INFORMATION: Angiotensin derivative

<400> SEQUENCE: 255

```
Asp Arg Val Tyr Ile His Pro Phe Gly Gly Gly Gly Gly Cys Gly
1               5                   10                  15

Gly Gly Gly Gly Asp Arg Val Tyr Ile His Pro Phe
            20                  25
```

<210> SEQ ID NO 256
<211> LENGTH: 24
<212> TYPE: PRT
<213> ORGANISM: Unknown
<220> FEATURE:
<223> OTHER INFORMATION: Angiotensin derivative

<400> SEQUENCE: 256

```
Asp Arg Val Tyr Ile His Pro Phe Gly Cys Gly Gly Gly Gly Gly
1               5                   10                  15

Asp Arg Val Tyr Ile His Pro Phe
            20
```

<210> SEQ ID NO 257
<211> LENGTH: 25
<212> TYPE: PRT
<213> ORGANISM: Unknown
<220> FEATURE:
<223> OTHER INFORMATION: Angiotensin derivative

<400> SEQUENCE: 257

```
Asp Arg Val Tyr Ile His Pro Phe Gly Gly Cys Gly Gly Gly Gly
1               5                   10                  15

Gly Asp Arg Val Tyr Ile His Pro Phe
            20                  25
```

<210> SEQ ID NO 258
<211> LENGTH: 26
<212> TYPE: PRT
<213> ORGANISM: Unknown
<220> FEATURE:
<223> OTHER INFORMATION: Angiotensin derivative

<400> SEQUENCE: 258

Asp Arg Val Tyr Ile His Pro Phe Gly Gly Cys Gly Gly Gly Gly
1               5                   10                  15

Gly Gly Asp Arg Val Tyr Ile His Pro Phe
            20                  25

<210> SEQ ID NO 259
<211> LENGTH: 27
<212> TYPE: PRT
<213> ORGANISM: Unknown
<220> FEATURE:
<223> OTHER INFORMATION: Angiotensin derivative

<400> SEQUENCE: 259

Asp Arg Val Tyr Ile His Pro Phe Gly Gly Gly Cys Gly Gly Gly
1               5                   10                  15

Gly Gly Gly Asp Arg Val Tyr Ile His Pro Phe
            20                  25

<210> SEQ ID NO 260
<211> LENGTH: 28
<212> TYPE: PRT
<213> ORGANISM: Unknown
<220> FEATURE:
<223> OTHER INFORMATION: Angiotensin derivative

<400> SEQUENCE: 260

Asp Arg Val Tyr Ile His Pro Phe Gly Gly Gly Gly Cys Gly Gly
1               5                   10                  15

Gly Gly Gly Gly Asp Arg Val Tyr Ile His Pro Phe
            20                  25

<210> SEQ ID NO 261
<211> LENGTH: 29
<212> TYPE: PRT
<213> ORGANISM: Unknown
<220> FEATURE:
<223> OTHER INFORMATION: Angiotensin derivative

<400> SEQUENCE: 261

Asp Arg Val Tyr Ile His Pro Phe Gly Gly Gly Gly Gly Cys Gly
1               5                   10                  15

Gly Gly Gly Gly Gly Asp Arg Val Tyr Ile His Pro Phe
            20                  25

<210> SEQ ID NO 262
<211> LENGTH: 22
<212> TYPE: PRT
<213> ORGANISM: Unknown
<220> FEATURE:
<223> OTHER INFORMATION: Angiotensin derivative

<400> SEQUENCE: 262

Phe Pro His Ile Tyr Val Arg Asp Gly Gly Cys Gly Asp Arg Val Tyr
1               5                   10                  15

Ile His Pro Phe His Leu
            20

<210> SEQ ID NO 263
<211> LENGTH: 23
<212> TYPE: PRT
<213> ORGANISM: Unknown
<220> FEATURE:
<223> OTHER INFORMATION: Angiotensin derivative -continued

```
<400> SEQUENCE: 263

Phe Pro His Ile Tyr Val Arg Asp Gly Gly Cys Gly Asp Arg Val
1               5                   10                  15

Tyr Ile His Pro Phe His Leu
            20

<210> SEQ ID NO 264
<211> LENGTH: 24
<212> TYPE: PRT
<213> ORGANISM: Unknown
<220> FEATURE:
<223> OTHER INFORMATION: Angiotensin derivative

<400> SEQUENCE: 264

Phe Pro His Ile Tyr Val Arg Asp Gly Gly Gly Cys Gly Asp Arg
1               5                   10                  15

Val Tyr Ile His Pro Phe His Leu
            20

<210> SEQ ID NO 265
<211> LENGTH: 25
<212> TYPE: PRT
<213> ORGANISM: Unknown
<220> FEATURE:
<223> OTHER INFORMATION: Angiotensin derivative

<400> SEQUENCE: 265

Phe Pro His Ile Tyr Val Arg Asp Gly Gly Gly Gly Cys Gly Asp
1               5                   10                  15

Arg Val Tyr Ile His Pro Phe His Leu
            20                  25

<210> SEQ ID NO 266
<211> LENGTH: 26
<212> TYPE: PRT
<213> ORGANISM: Unknown
<220> FEATURE:
<223> OTHER INFORMATION: Angiotensin derivative

<400> SEQUENCE: 266

Phe Pro His Ile Tyr Val Arg Asp Gly Gly Gly Gly Gly Cys Gly
1               5                   10                  15

Asp Arg Val Tyr Ile His Pro Phe His Leu
            20                  25

<210> SEQ ID NO 267
<211> LENGTH: 22
<212> TYPE: PRT
<213> ORGANISM: Unknown
<220> FEATURE:
<223> OTHER INFORMATION: Angiotensin derivative

<400> SEQUENCE: 267

Phe Pro His Ile Tyr Val Arg Asp Gly Cys Gly Gly Asp Arg Val Tyr
1               5                   10                  15

Ile His Pro Phe His Leu
            20

<210> SEQ ID NO 268
<211> LENGTH: 23
<212> TYPE: PRT
<213> ORGANISM: Unknown
<220> FEATURE:
<223> OTHER INFORMATION: Angiotensin derivative
```

-continued

```
<400> SEQUENCE: 268

Phe Pro His Ile Tyr Val Arg Asp Gly Gly Cys Gly Gly Asp Arg Val
1               5                   10                  15

Tyr Ile His Pro Phe His Leu
            20

<210> SEQ ID NO 269
<211> LENGTH: 24
<212> TYPE: PRT
<213> ORGANISM: Unknown
<220> FEATURE:
<223> OTHER INFORMATION: Angiotensin derivative

<400> SEQUENCE: 269

Phe Pro His Ile Tyr Val Arg Asp Gly Gly Gly Cys Gly Gly Asp Arg
1               5                   10                  15

Val Tyr Ile His Pro Phe His Leu
            20

<210> SEQ ID NO 270
<211> LENGTH: 25
<212> TYPE: PRT
<213> ORGANISM: Unknown
<220> FEATURE:
<223> OTHER INFORMATION: Angiotensin derivative

<400> SEQUENCE: 270

Phe Pro His Ile Tyr Val Arg Asp Gly Gly Gly Cys Gly Gly Asp
1               5                   10                  15

Arg Val Tyr Ile His Pro Phe His Leu
            20                  25

<210> SEQ ID NO 271
<211> LENGTH: 26
<212> TYPE: PRT
<213> ORGANISM: Unknown
<220> FEATURE:
<223> OTHER INFORMATION: Angiotensin derivative

<400> SEQUENCE: 271

Phe Pro His Ile Tyr Val Arg Asp Gly Gly Gly Gly Cys Gly Gly
1               5                   10                  15

Asp Arg Val Tyr Ile His Pro Phe His Leu
            20                  25

<210> SEQ ID NO 272
<211> LENGTH: 27
<212> TYPE: PRT
<213> ORGANISM: Unknown
<220> FEATURE:
<223> OTHER INFORMATION: Angiotensin derivative

<400> SEQUENCE: 272

Phe Pro His Ile Tyr Val Arg Asp Gly Gly Gly Gly Gly Cys Gly
1               5                   10                  15

Gly Asp Arg Val Tyr Ile His Pro Phe His Leu
            20                  25

<210> SEQ ID NO 273
<211> LENGTH: 23
<212> TYPE: PRT
<213> ORGANISM: Unknown
<220> FEATURE:
```

<223> OTHER INFORMATION: Angiotensin derivative

<400> SEQUENCE: 273

Phe Pro His Ile Tyr Val Arg Asp Gly Cys Gly Gly Gly Asp Arg Val
1               5                   10                  15

Tyr Ile His Pro Phe His Leu
            20

<210> SEQ ID NO 274
<211> LENGTH: 24
<212> TYPE: PRT
<213> ORGANISM: Unknown
<220> FEATURE:
<223> OTHER INFORMATION: Angiotensin derivative

<400> SEQUENCE: 274

Phe Pro His Ile Tyr Val Arg Asp Gly Gly Cys Gly Gly Gly Asp Arg
1               5                   10                  15

Val Tyr Ile His Pro Phe His Leu
            20

<210> SEQ ID NO 275
<211> LENGTH: 25
<212> TYPE: PRT
<213> ORGANISM: Unknown
<220> FEATURE:
<223> OTHER INFORMATION: Angiotensin derivative

<400> SEQUENCE: 275

Phe Pro His Ile Tyr Val Arg Asp Gly Gly Gly Cys Gly Gly Gly Asp
1               5                   10                  15

Arg Val Tyr Ile His Pro Phe His Leu
            20                  25

<210> SEQ ID NO 276
<211> LENGTH: 26
<212> TYPE: PRT
<213> ORGANISM: Unknown
<220> FEATURE:
<223> OTHER INFORMATION: Angiotensin derivative

<400> SEQUENCE: 276

Phe Pro His Ile Tyr Val Arg Asp Gly Gly Gly Gly Cys Gly Gly Gly
1               5                   10                  15

Asp Arg Val Tyr Ile His Pro Phe His Leu
            20                  25

<210> SEQ ID NO 277
<211> LENGTH: 27
<212> TYPE: PRT
<213> ORGANISM: Unknown
<220> FEATURE:
<223> OTHER INFORMATION: Angiotensin derivative

<400> SEQUENCE: 277

Phe Pro His Ile Tyr Val Arg Asp Gly Gly Gly Gly Gly Cys Gly Gly
1               5                   10                  15

Gly Asp Arg Val Tyr Ile His Pro Phe His Leu
            20                  25

<210> SEQ ID NO 278
<211> LENGTH: 28
<212> TYPE: PRT
<213> ORGANISM: Unknown

```
<220> FEATURE:
<223> OTHER INFORMATION: Angiotensin derivative

<400> SEQUENCE: 278

Phe Pro His Ile Tyr Val Arg Asp Gly Gly Gly Gly Gly Cys Gly
1               5                   10                  15

Gly Gly Asp Arg Val Tyr Ile His Pro Phe His Leu
            20                  25

<210> SEQ ID NO 279
<211> LENGTH: 24
<212> TYPE: PRT
<213> ORGANISM: Unknown
<220> FEATURE:
<223> OTHER INFORMATION: Angiotensin derivative

<400> SEQUENCE: 279

Phe Pro His Ile Tyr Val Arg Asp Gly Cys Gly Gly Gly Gly Asp Arg
1               5                   10                  15

Val Tyr Ile His Pro Phe His Leu
            20

<210> SEQ ID NO 280
<211> LENGTH: 25
<212> TYPE: PRT
<213> ORGANISM: Unknown
<220> FEATURE:
<223> OTHER INFORMATION: Angiotensin derivative

<400> SEQUENCE: 280

Phe Pro His Ile Tyr Val Arg Asp Gly Gly Cys Gly Gly Gly Asp
1               5                   10                  15

Arg Val Tyr Ile His Pro Phe His Leu
            20                  25

<210> SEQ ID NO 281
<211> LENGTH: 26
<212> TYPE: PRT
<213> ORGANISM: Unknown
<220> FEATURE:
<223> OTHER INFORMATION: Angiotensin derivative

<400> SEQUENCE: 281

Phe Pro His Ile Tyr Val Arg Asp Gly Gly Gly Cys Gly Gly Gly
1               5                   10                  15

Asp Arg Val Tyr Ile His Pro Phe His Leu
            20                  25

<210> SEQ ID NO 282
<211> LENGTH: 27
<212> TYPE: PRT
<213> ORGANISM: Unknown
<220> FEATURE:
<223> OTHER INFORMATION: Angiotensin derivative

<400> SEQUENCE: 282

Phe Pro His Ile Tyr Val Arg Asp Gly Gly Gly Gly Cys Gly Gly
1               5                   10                  15

Gly Asp Arg Val Tyr Ile His Pro Phe His Leu
            20                  25

<210> SEQ ID NO 283
<211> LENGTH: 28
<212> TYPE: PRT
```

```
<213> ORGANISM: Unknown
<220> FEATURE:
<223> OTHER INFORMATION: Angiotensin derivative

<400> SEQUENCE: 283

Phe Pro His Ile Tyr Val Arg Asp Gly Gly Gly Gly Cys Gly Gly
1               5                   10                  15

Gly Gly Asp Arg Val Tyr Ile His Pro Phe His Leu
            20                  25

<210> SEQ ID NO 284
<211> LENGTH: 29
<212> TYPE: PRT
<213> ORGANISM: Unknown
<220> FEATURE:
<223> OTHER INFORMATION: Angiotensin derivative

<400> SEQUENCE: 284

Phe Pro His Ile Tyr Val Arg Asp Gly Gly Gly Gly Gly Cys Gly
1               5                   10                  15

Gly Gly Gly Asp Arg Val Tyr Ile His Pro Phe His Leu
            20                  25

<210> SEQ ID NO 285
<211> LENGTH: 25
<212> TYPE: PRT
<213> ORGANISM: Unknown
<220> FEATURE:
<223> OTHER INFORMATION: Angiotensin derivative

<400> SEQUENCE: 285

Phe Pro His Ile Tyr Val Arg Asp Gly Cys Gly Gly Gly Gly Asp
1               5                   10                  15

Arg Val Tyr Ile His Pro Phe His Leu
            20                  25

<210> SEQ ID NO 286
<211> LENGTH: 26
<212> TYPE: PRT
<213> ORGANISM: Unknown
<220> FEATURE:
<223> OTHER INFORMATION: Angiotensin derivative

<400> SEQUENCE: 286

Phe Pro His Ile Tyr Val Arg Asp Gly Gly Cys Gly Gly Gly Gly
1               5                   10                  15

Asp Arg Val Tyr Ile His Pro Phe His Leu
            20                  25

<210> SEQ ID NO 287
<211> LENGTH: 27
<212> TYPE: PRT
<213> ORGANISM: Unknown
<220> FEATURE:
<223> OTHER INFORMATION: Angiotensin derivative

<400> SEQUENCE: 287

Phe Pro His Ile Tyr Val Arg Asp Gly Gly Gly Cys Gly Gly Gly
1               5                   10                  15

Gly Asp Arg Val Tyr Ile His Pro Phe His Leu
            20                  25

<210> SEQ ID NO 288
<211> LENGTH: 28
```

```
<212> TYPE: PRT
<213> ORGANISM: Unknown
<220> FEATURE:
<223> OTHER INFORMATION: Angiotensin derivative

<400> SEQUENCE: 288

Phe Pro His Ile Tyr Val Arg Asp Gly Gly Gly Cys Gly Gly Gly
1               5                   10                  15

Gly Gly Asp Arg Val Tyr Ile His Pro Phe His Leu
            20                  25

<210> SEQ ID NO 289
<211> LENGTH: 29
<212> TYPE: PRT
<213> ORGANISM: Unknown
<220> FEATURE:
<223> OTHER INFORMATION: Angiotensin derivative

<400> SEQUENCE: 289

Phe Pro His Ile Tyr Val Arg Asp Gly Gly Gly Gly Cys Gly Gly
1               5                   10                  15

Gly Gly Gly Asp Arg Val Tyr Ile His Pro Phe His Leu
            20                  25

<210> SEQ ID NO 290
<211> LENGTH: 30
<212> TYPE: PRT
<213> ORGANISM: Unknown
<220> FEATURE:
<223> OTHER INFORMATION: Angiotensin derivative

<400> SEQUENCE: 290

Phe Pro His Ile Tyr Val Arg Asp Gly Gly Gly Gly Gly Cys Gly
1               5                   10                  15

Gly Gly Gly Gly Asp Arg Val Tyr Ile His Pro Phe His Leu
            20                  25                  30

<210> SEQ ID NO 291
<211> LENGTH: 26
<212> TYPE: PRT
<213> ORGANISM: Unknown
<220> FEATURE:
<223> OTHER INFORMATION: Angiotensin derivative

<400> SEQUENCE: 291

Phe Pro His Ile Tyr Val Arg Asp Gly Cys Gly Gly Gly Gly Gly
1               5                   10                  15

Asp Arg Val Tyr Ile His Pro Phe His Leu
            20                  25

<210> SEQ ID NO 292
<211> LENGTH: 27
<212> TYPE: PRT
<213> ORGANISM: Unknown
<220> FEATURE:
<223> OTHER INFORMATION: Angiotensin derivative

<400> SEQUENCE: 292

Phe Pro His Ile Tyr Val Arg Asp Gly Gly Cys Gly Gly Gly Gly
1               5                   10                  15

Gly Asp Arg Val Tyr Ile His Pro Phe His Leu
            20                  25

<210> SEQ ID NO 293
```

```
<211> LENGTH: 28
<212> TYPE: PRT
<213> ORGANISM: Unknown
<220> FEATURE:
<223> OTHER INFORMATION: Angiotensin derivative

<400> SEQUENCE: 293

Phe Pro His Ile Tyr Val Arg Asp Gly Gly Gly Cys Gly Gly Gly Gly
1               5                   10                  15

Gly Gly Asp Arg Val Tyr Ile His Pro Phe His Leu
            20                  25

<210> SEQ ID NO 294
<211> LENGTH: 29
<212> TYPE: PRT
<213> ORGANISM: Unknown
<220> FEATURE:
<223> OTHER INFORMATION: Angiotensin derivative

<400> SEQUENCE: 294

Phe Pro His Ile Tyr Val Arg Asp Gly Gly Gly Gly Cys Gly Gly Gly
1               5                   10                  15

Gly Gly Gly Asp Arg Val Tyr Ile His Pro Phe His Leu
            20                  25

<210> SEQ ID NO 295
<211> LENGTH: 30
<212> TYPE: PRT
<213> ORGANISM: Unknown
<220> FEATURE:
<223> OTHER INFORMATION: Angiotensin derivative

<400> SEQUENCE: 295

Phe Pro His Ile Tyr Val Arg Asp Gly Gly Gly Gly Gly Cys Gly Gly
1               5                   10                  15

Gly Gly Gly Gly Asp Arg Val Tyr Ile His Pro Phe His Leu
            20                  25                  30

<210> SEQ ID NO 296
<211> LENGTH: 31
<212> TYPE: PRT
<213> ORGANISM: Unknown
<220> FEATURE:
<223> OTHER INFORMATION: Angiotensin derivative

<400> SEQUENCE: 296

Phe Pro His Ile Tyr Val Arg Asp Gly Gly Gly Gly Gly Gly Cys Gly
1               5                   10                  15

Gly Gly Gly Gly Gly Asp Arg Val Tyr Ile His Pro Phe His Leu
            20                  25                  30

<210> SEQ ID NO 297
<211> LENGTH: 20
<212> TYPE: PRT
<213> ORGANISM: Unknown
<220> FEATURE:
<223> OTHER INFORMATION: Angiotensin derivative

<400> SEQUENCE: 297

Phe Pro His Ile Tyr Val Arg Asp Gly Gly Cys Gly Asp Arg Val Tyr
1               5                   10                  15

Ile His Pro Phe
            20
```

```
<210> SEQ ID NO 298
<211> LENGTH: 21
<212> TYPE: PRT
<213> ORGANISM: Unknown
<220> FEATURE:
<223> OTHER INFORMATION: Angiotensin derivative

<400> SEQUENCE: 298

Phe Pro His Ile Tyr Val Arg Asp Gly Gly Gly Cys Gly Asp Arg Val
1               5                   10                  15

Tyr Ile His Pro Phe
            20

<210> SEQ ID NO 299
<211> LENGTH: 22
<212> TYPE: PRT
<213> ORGANISM: Unknown
<220> FEATURE:
<223> OTHER INFORMATION: Angiotensin derivative

<400> SEQUENCE: 299

Phe Pro His Ile Tyr Val Arg Asp Gly Gly Gly Gly Cys Gly Asp Arg
1               5                   10                  15

Val Tyr Ile His Pro Phe
            20

<210> SEQ ID NO 300
<211> LENGTH: 23
<212> TYPE: PRT
<213> ORGANISM: Unknown
<220> FEATURE:
<223> OTHER INFORMATION: Angiotensin derivative

<400> SEQUENCE: 300

Phe Pro His Ile Tyr Val Arg Asp Gly Gly Gly Gly Gly Cys Gly Asp
1               5                   10                  15

Arg Val Tyr Ile His Pro Phe
            20

<210> SEQ ID NO 301
<211> LENGTH: 24
<212> TYPE: PRT
<213> ORGANISM: Unknown
<220> FEATURE:
<223> OTHER INFORMATION: Angiotensin derivative

<400> SEQUENCE: 301

Phe Pro His Ile Tyr Val Arg Asp Gly Gly Gly Gly Gly Gly Cys Gly
1               5                   10                  15

Asp Arg Val Tyr Ile His Pro Phe
            20

<210> SEQ ID NO 302
<211> LENGTH: 20
<212> TYPE: PRT
<213> ORGANISM: Unknown
<220> FEATURE:
<223> OTHER INFORMATION: Angiotensin derivative

<400> SEQUENCE: 302

Phe Pro His Ile Tyr Val Arg Asp Gly Cys Gly Gly Asp Arg Val Tyr
1               5                   10                  15

Ile His Pro Phe
            20
```

<210> SEQ ID NO 303
<211> LENGTH: 21
<212> TYPE: PRT
<213> ORGANISM: Unknown
<220> FEATURE:
<223> OTHER INFORMATION: Angiotensin derivative

<400> SEQUENCE: 303

Phe Pro His Ile Tyr Val Arg Asp Gly Gly Cys Gly Gly Asp Arg Val
1               5                   10                  15

Tyr Ile His Pro Phe
            20

<210> SEQ ID NO 304
<211> LENGTH: 22
<212> TYPE: PRT
<213> ORGANISM: Unknown
<220> FEATURE:
<223> OTHER INFORMATION: Angiotensin derivative

<400> SEQUENCE: 304

Phe Pro His Ile Tyr Val Arg Asp Gly Gly Gly Cys Gly Gly Asp Arg
1               5                   10                  15

Val Tyr Ile His Pro Phe
            20

<210> SEQ ID NO 305
<211> LENGTH: 23
<212> TYPE: PRT
<213> ORGANISM: Unknown
<220> FEATURE:
<223> OTHER INFORMATION: Angiotensin derivative

<400> SEQUENCE: 305

Phe Pro His Ile Tyr Val Arg Asp Gly Gly Gly Gly Cys Gly Gly Asp
1               5                   10                  15

Arg Val Tyr Ile His Pro Phe
            20

<210> SEQ ID NO 306
<211> LENGTH: 24
<212> TYPE: PRT
<213> ORGANISM: Unknown
<220> FEATURE:
<223> OTHER INFORMATION: Angiotensin derivative

<400> SEQUENCE: 306

Phe Pro His Ile Tyr Val Arg Asp Gly Gly Gly Gly Gly Cys Gly Gly
1               5                   10                  15

Asp Arg Val Tyr Ile His Pro Phe
            20

<210> SEQ ID NO 307
<211> LENGTH: 25
<212> TYPE: PRT
<213> ORGANISM: Unknown
<220> FEATURE:
<223> OTHER INFORMATION: Angiotensin derivative

<400> SEQUENCE: 307

Phe Pro His Ile Tyr Val Arg Asp Gly Gly Gly Gly Gly Gly Cys Gly
1               5                   10                  15

Gly Asp Arg Val Tyr Ile His Pro Phe
            20                  25

```
<210> SEQ ID NO 308
<211> LENGTH: 21
<212> TYPE: PRT
<213> ORGANISM: Unknown
<220> FEATURE:
<223> OTHER INFORMATION: Angiotensin derivative

<400> SEQUENCE: 308

Phe Pro His Ile Tyr Val Arg Asp Gly Cys Gly Gly Gly Asp Arg Val
1               5                   10                  15

Tyr Ile His Pro Phe
            20

<210> SEQ ID NO 309
<211> LENGTH: 22
<212> TYPE: PRT
<213> ORGANISM: Unknown
<220> FEATURE:
<223> OTHER INFORMATION: Angiotensin derivative

<400> SEQUENCE: 309

Phe Pro His Ile Tyr Val Arg Asp Gly Gly Cys Gly Gly Gly Asp Arg
1               5                   10                  15

Val Tyr Ile His Pro Phe
            20

<210> SEQ ID NO 310
<211> LENGTH: 23
<212> TYPE: PRT
<213> ORGANISM: Unknown
<220> FEATURE:
<223> OTHER INFORMATION: Angiotensin derivative

<400> SEQUENCE: 310

Phe Pro His Ile Tyr Val Arg Asp Gly Gly Gly Cys Gly Gly Gly Asp
1               5                   10                  15

Arg Val Tyr Ile His Pro Phe
            20

<210> SEQ ID NO 311
<211> LENGTH: 24
<212> TYPE: PRT
<213> ORGANISM: Unknown
<220> FEATURE:
<223> OTHER INFORMATION: Angiotensin derivative

<400> SEQUENCE: 311

Phe Pro His Ile Tyr Val Arg Asp Gly Gly Gly Gly Cys Gly Gly Gly
1               5                   10                  15

Asp Arg Val Tyr Ile His Pro Phe
            20

<210> SEQ ID NO 312
<211> LENGTH: 25
<212> TYPE: PRT
<213> ORGANISM: Unknown
<220> FEATURE:
<223> OTHER INFORMATION: Angiotensin derivative

<400> SEQUENCE: 312

Phe Pro His Ile Tyr Val Arg Asp Gly Gly Gly Gly Gly Cys Gly Gly
1               5                   10                  15

Gly Asp Arg Val Tyr Ile His Pro Phe
```

-continued

```
             20                  25

<210> SEQ ID NO 313
<211> LENGTH: 26
<212> TYPE: PRT
<213> ORGANISM: Unknown
<220> FEATURE:
<223> OTHER INFORMATION: Angiotensin derivative

<400> SEQUENCE: 313

Phe Pro His Ile Tyr Val Arg Asp Gly Gly Gly Gly Gly Cys Gly
1               5                  10                  15

Gly Gly Asp Arg Val Tyr Ile His Pro Phe
            20                  25

<210> SEQ ID NO 314
<211> LENGTH: 22
<212> TYPE: PRT
<213> ORGANISM: Unknown
<220> FEATURE:
<223> OTHER INFORMATION: Angiotensin derivative

<400> SEQUENCE: 314

Phe Pro His Ile Tyr Val Arg Asp Gly Cys Gly Gly Gly Asp Arg
1               5                  10                  15

Val Tyr Ile His Pro Phe
            20

<210> SEQ ID NO 315
<211> LENGTH: 23
<212> TYPE: PRT
<213> ORGANISM: Unknown
<220> FEATURE:
<223> OTHER INFORMATION: Angiotensin derivative

<400> SEQUENCE: 315

Phe Pro His Ile Tyr Val Arg Asp Gly Gly Cys Gly Gly Gly Asp
1               5                  10                  15

Arg Val Tyr Ile His Pro Phe
            20

<210> SEQ ID NO 316
<211> LENGTH: 24
<212> TYPE: PRT
<213> ORGANISM: Unknown
<220> FEATURE:
<223> OTHER INFORMATION: Angiotensin derivative

<400> SEQUENCE: 316

Phe Pro His Ile Tyr Val Arg Asp Gly Gly Gly Cys Gly Gly Gly
1               5                  10                  15

Asp Arg Val Tyr Ile His Pro Phe
            20

<210> SEQ ID NO 317
<211> LENGTH: 25
<212> TYPE: PRT
<213> ORGANISM: Unknown
<220> FEATURE:
<223> OTHER INFORMATION: Angiotensin derivative

<400> SEQUENCE: 317

Phe Pro His Ile Tyr Val Arg Asp Gly Gly Gly Gly Cys Gly Gly
1               5                  10                  15
```

```
Gly Asp Arg Val Tyr Ile His Pro Phe
            20                  25

<210> SEQ ID NO 318
<211> LENGTH: 26
<212> TYPE: PRT
<213> ORGANISM: Unknown
<220> FEATURE:
<223> OTHER INFORMATION: Angiotensin derivative

<400> SEQUENCE: 318

Phe Pro His Ile Tyr Val Arg Asp Gly Gly Gly Gly Cys Gly Gly
1               5                   10                  15

Gly Gly Asp Arg Val Tyr Ile His Pro Phe
            20                  25

<210> SEQ ID NO 319
<211> LENGTH: 27
<212> TYPE: PRT
<213> ORGANISM: Unknown
<220> FEATURE:
<223> OTHER INFORMATION: Angiotensin derivative

<400> SEQUENCE: 319

Phe Pro His Ile Tyr Val Arg Asp Gly Gly Gly Gly Gly Cys Gly
1               5                   10                  15

Gly Gly Gly Asp Arg Val Tyr Ile His Pro Phe
            20                  25

<210> SEQ ID NO 320
<211> LENGTH: 23
<212> TYPE: PRT
<213> ORGANISM: Unknown
<220> FEATURE:
<223> OTHER INFORMATION: Angiotensin derivative

<400> SEQUENCE: 320

Phe Pro His Ile Tyr Val Arg Asp Gly Cys Gly Gly Gly Gly Asp
1               5                   10                  15

Arg Val Tyr Ile His Pro Phe
            20

<210> SEQ ID NO 321
<211> LENGTH: 24
<212> TYPE: PRT
<213> ORGANISM: Unknown
<220> FEATURE:
<223> OTHER INFORMATION: Angiotensin derivative

<400> SEQUENCE: 321

Phe Pro His Ile Tyr Val Arg Asp Gly Gly Cys Gly Gly Gly Gly
1               5                   10                  15

Asp Arg Val Tyr Ile His Pro Phe
            20

<210> SEQ ID NO 322
<211> LENGTH: 25
<212> TYPE: PRT
<213> ORGANISM: Unknown
<220> FEATURE:
<223> OTHER INFORMATION: Angiotensin derivative

<400> SEQUENCE: 322

Phe Pro His Ile Tyr Val Arg Asp Gly Gly Gly Cys Gly Gly Gly
1               5                   10                  15
```

Gly Asp Arg Val Tyr Ile His Pro Phe
            20                  25

<210> SEQ ID NO 323
<211> LENGTH: 26
<212> TYPE: PRT
<213> ORGANISM: Unknown
<220> FEATURE:
<223> OTHER INFORMATION: Angiotensin derivative

<400> SEQUENCE: 323

Phe Pro His Ile Tyr Val Arg Asp Gly Gly Gly Cys Gly Gly
1               5                   10                  15

Gly Gly Asp Arg Val Tyr Ile His Pro Phe
            20                  25

<210> SEQ ID NO 324
<211> LENGTH: 27
<212> TYPE: PRT
<213> ORGANISM: Unknown
<220> FEATURE:
<223> OTHER INFORMATION: Angiotensin derivative

<400> SEQUENCE: 324

Phe Pro His Ile Tyr Val Arg Asp Gly Gly Gly Gly Cys Gly
1               5                   10                  15

Gly Gly Gly Asp Arg Val Tyr Ile His Pro Phe
            20                  25

<210> SEQ ID NO 325
<211> LENGTH: 28
<212> TYPE: PRT
<213> ORGANISM: Unknown
<220> FEATURE:
<223> OTHER INFORMATION: Angiotensin derivative

<400> SEQUENCE: 325

Phe Pro His Ile Tyr Val Arg Asp Gly Gly Gly Gly Gly Cys Gly
1               5                   10                  15

Gly Gly Gly Gly Asp Arg Val Tyr Ile His Pro Phe
            20                  25

<210> SEQ ID NO 326
<211> LENGTH: 24
<212> TYPE: PRT
<213> ORGANISM: Unknown
<220> FEATURE:
<223> OTHER INFORMATION: Angiotensin derivative

<400> SEQUENCE: 326

Phe Pro His Ile Tyr Val Arg Asp Gly Cys Gly Gly Gly Gly Gly
1               5                   10                  15

Asp Arg Val Tyr Ile His Pro Phe
            20

<210> SEQ ID NO 327
<211> LENGTH: 25
<212> TYPE: PRT
<213> ORGANISM: Unknown
<220> FEATURE:
<223> OTHER INFORMATION: Angiotensin derivative

<400> SEQUENCE: 327

Phe Pro His Ile Tyr Val Arg Asp Gly Gly Cys Gly Gly Gly Gly Gly

```
                1               5                   10                  15
Gly Asp Arg Val Tyr Ile His Pro Phe
                20                  25

<210> SEQ ID NO 328
<211> LENGTH: 26
<212> TYPE: PRT
<213> ORGANISM: Unknown
<220> FEATURE:
<223> OTHER INFORMATION: Angiotensin derivative

<400> SEQUENCE: 328

Phe Pro His Ile Tyr Val Arg Asp Gly Gly Gly Cys Gly Gly Gly
1               5                   10                  15

Gly Gly Asp Arg Val Tyr Ile His Pro Phe
                20                  25

<210> SEQ ID NO 329
<211> LENGTH: 27
<212> TYPE: PRT
<213> ORGANISM: Unknown
<220> FEATURE:
<223> OTHER INFORMATION: Angiotensin derivative

<400> SEQUENCE: 329

Phe Pro His Ile Tyr Val Arg Asp Gly Gly Gly Gly Cys Gly Gly
1               5                   10                  15

Gly Gly Gly Asp Arg Val Tyr Ile His Pro Phe
                20                  25

<210> SEQ ID NO 330
<211> LENGTH: 28
<212> TYPE: PRT
<213> ORGANISM: Unknown
<220> FEATURE:
<223> OTHER INFORMATION: Angiotensin derivative

<400> SEQUENCE: 330

Phe Pro His Ile Tyr Val Arg Asp Gly Gly Gly Gly Gly Cys Gly Gly
1               5                   10                  15

Gly Gly Gly Gly Asp Arg Val Tyr Ile His Pro Phe
                20                  25

<210> SEQ ID NO 331
<211> LENGTH: 29
<212> TYPE: PRT
<213> ORGANISM: Unknown
<220> FEATURE:
<223> OTHER INFORMATION: Angiotensin derivative

<400> SEQUENCE: 331

Phe Pro His Ile Tyr Val Arg Asp Gly Gly Gly Gly Gly Gly Cys Gly
1               5                   10                  15

Gly Gly Gly Gly Gly Asp Arg Val Tyr Ile His Pro Phe
                20                  25
```